(12) United States Patent
Fridman et al.

(10) Patent No.: US 11,854,664 B2
(45) Date of Patent: Dec. 26, 2023

(54) COMPLEX MOLECULE SUBSTRUCTURE IDENTIFICATION SYSTEMS, APPARATUSES AND METHODS

(71) Applicant: Merck Sharp & Dohme Corp., Rahway, NJ (US)

(72) Inventors: Arthur Fridman, Brooklyn, NY (US); Ansuman Bagchi, Plainsboro, NY (US); Xiang Yu, North Wales, PA (US); Mark Cancilla, Philadelphia, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 551 days.

(21) Appl. No.: 16/973,175

(22) PCT Filed: Jun. 11, 2019

(86) PCT No.: PCT/US2019/036449
§ 371 (c)(1),
(2) Date: Dec. 8, 2020

(87) PCT Pub. No.: WO2019/241178
PCT Pub. Date: Dec. 19, 2019

(65) Prior Publication Data
US 2021/0265024 A1    Aug. 26, 2021

Related U.S. Application Data

(60) Provisional application No. 62/770,252, filed on Nov. 21, 2018, provisional application No. 62/752,152, (Continued)

(51) Int. Cl.
*G16B 15/00* (2019.01)
*G06F 16/2455* (2019.01)
(Continued)

(52) U.S. Cl.
CPC ......... *G16B 15/00* (2019.02); *G06F 16/2455* (2019.01); *G06F 16/9024* (2019.01);
(Continued)

(58) Field of Classification Search
CPC ............. G06F 16/2246; G06F 16/2282; G06F 16/2428; G06F 16/2456; G06F 16/248;
(Continued)

(56) References Cited

U.S. PATENT DOCUMENTS 9,700,359 B2 * 7/2017 Hatch .................... A61B 17/80
10,392,443 B2 * 8/2019 Chakraborty ...... A61K 31/7105
(Continued)

FOREIGN PATENT DOCUMENTS

CN    104765984 A    7/2015
CN    107077592 A    8/2017
(Continued)

OTHER PUBLICATIONS

Adai et al., "Creating a Map of Protein Function with an Algorithm for Visualizing Very Large Biological Networks," J. Mol. Biol., vol. 340, pp. 179-190, Jun. 2004.
(Continued)

*Primary Examiner* — Mohammad K Islam
(74) *Attorney, Agent, or Firm* — Grady L. White; Potomac Law Group, PLLC

(57) ABSTRACT

Embodiments of the present invention provide a computer-implemented system and method for generating and searching a database containing all of the potential substructures (e.g., metabolites) of a chosen complex molecule based on minimum cleavable units (MCUs) of the chosen complex molecule, wherein each record in the generated database suitably defines the molecular weight and physical arrangement of each substructure. Embodiments of the invention also provide a user interface and a search engine for searching
(Continued)

ing the database based on a query molecular weight (or query molecular weight range) to identify all of the substructures having a total molecular weight matching the query molecular weight or range. Embodiments of the invention are also capable of transmitting to a display device operated by an end user a description and/or a graphical representation of every identified substructure of the chosen complex molecule.

27 Claims, 47 Drawing Sheets

Related U.S. Application Data filed on Oct. 29, 2018, provisional application No. 62/683,582, filed on Jun. 11, 2018.

(51) Int. Cl.
*G16C 20/20* (2019.01)
*G16C 20/80* (2019.01)
*G16C 20/40* (2019.01)
*G06F 16/901* (2019.01)
*G16C 20/90* (2019.01)

(52) U.S. Cl.
CPC ............ *G16C 20/20* (2019.02); *G16C 20/40* (2019.02); *G16C 20/80* (2019.02); *G16C 20/90* (2019.02)

(58) Field of Classification Search
CPC ............ G06F 16/2455; G06F 16/9024; G01N 2400/02; G01N 2400/14; G01N 27/623; G01N 33/54353; G01N 33/56972; G01N 33/56988; G01N 33/57415; G16B 15/00; G16B 20/00; G16B 40/00; G16B 99/00; G16B 45/00; G16B 50/00; G16C 20/20; G16C 20/40; G16C 20/90; G16C 99/00; G16C 20/80
See application file for complete search history.

(56) References Cited

U.S. PATENT DOCUMENTS

| | | | |
|---|---|---|---|
| 10,620,217 B2* | 4/2020 | Bieniarz | G01N 33/542 |
| 2006/0085142 A1 | 4/2006 | Mistrik | |
| 2007/0213297 A1 | 9/2007 | Wong | |
| 2013/0337456 A1 | 12/2013 | Honisch et al. | |
| 2014/0045273 A1 | 2/2014 | Cerda et al. | |
| 2016/0153060 A1 | 6/2016 | Ling et al. | |
| 2018/0011899 A1 | 1/2018 | Dean et al. | |
| 2018/0318388 A1* | 11/2018 | Pandurangi | A61K 31/355 |

FOREIGN PATENT DOCUMENTS

| | | |
|---|---|---|
| JP | 2007508637 A | 4/2007 |
| JP | 2007312776 A | 12/2007 |
| KR | 20070045141 A | 5/2007 |
| KR | 20140145753 A | 12/2014 |
| WO | 0221139 A2 | 3/2002 |

OTHER PUBLICATIONS

Bader et al., "An automated method for finding molecular complexes in large protein interaction networks," BMC Bioinformatics, vol. 4, p. 2, Jan. 2003.
Engler et al., "Enumerating common molecular substructures," PeerJ Preprints, pp. 1-10, Sep. 2017.
Fontaine et al., "Results Towards a m/z unlimited algorithm for peptide and protein structure elucidation," 65th ASMS Conference on Mass Spectrometry and Allied Topics, Jun. 2017.
Plomley et al., "The Application of Research Grade MetabolitePilot Softward for the Determination of Exenatide Catabolites using HRAM with SWATH Acquistion," 65th ASMS Conference on Mass Spectrometry and Allied Topics, Jun. 2017.
Radchenko et al., "Software-aided approach to investigate peptide structure and metabolic susceptibility of amide bonds in peptide drugs based on high resolution mass spectrometry," PLoS One, vol. 12, No. 11, e0186461, Nov. 2017.
Siegel et al., "Disulfide Linked Linear Peptides ANP, Insulin, ShK Toxin: Automatic Assignment of Exact-Mass ESI-MS/Ms Fragment Ion Structures Using the MASSPEC Algorithm," 64th ASMA Conference on Mass Spectrometry and Allied Topics, Jun. 2016.
Siegel et al., "MASSPEC: a graphics-based data system for correlating a mass spectrum with a proposed structure," Analytica Chimica Acta., vol. 237, pp. 459-472, 1990.
Siegel et al., "MASSPEC: A Powerful Computer Program for Correlating/Elucidating Molecular Structures Using Tandem Mass Spectral Data," 64th Annual ASMS Conference, 2016.
Trexler et al., "Utilization of Mass-MetaSite for in vitro and in vivo Metabolite Identification of Complex Therapeutic Peptides," American Society for Mass Spectrometry, St. Louis, Missouri, US, Jun. 1, 2015.
Wu et al., "Recognizing Protein Substructure Similarity Using Segmental Threading," Structure, vol. 18, No. 7, pp. 858-867, Jul. 2010.
Yu et al., "Unambiguous Metabolite Identification of Peptide and Protein Therapeutics by Top-Down Protein/Peptide MetID Platform," The Delaware Valley Drug Metabolism Discussion Group, Sep. 2016.
Yu et al., "Understanding the Metabolism of Peptide and Protein Therapeutics by Developing a Top-Down Metabolite Identification Program," 64th ASMS Conference on Mass Spectrometry and Allied Topics, Jun. 2016.
Yu et al., "Understanding the Metabolism of Protein and Peptide Therapeutics by Developing a Top Down Protein Metabolite Identification Platform," 2016 APA Conference Abstract, Jun. 2016.
Yu et al., "Understanding the Metabolism of Protein and Peptide Therapeutics by Developing a Top-Down Protein Metabolite Identification Platform," 2016 ASMS Conference Abstract, Jun. 2016.
Yu et al., "Understanding the Metabolism of Protein and Peptide Therapeutics by Developing a Top-Down Protein Metabolite Identification Platform," 12th Annual APA Meeting, Sep. 2016.
Zhang et al., "HELM: A Hierarchical Notation Language for Complex Biomolecule Structure Representation," Journal of Chemical Information and Modeling, vol. 52, pp. 2796-2806, Sep. 2012.
Ezan et al., "Assessment of the metabolism of therapeutic proteins and antibodies," Expert Opinion on Drug Metabolism & Toxicology, vol. 10, No. 8, pp. 1079-0191, 2014.
Yu et al., "Metabolite Identification of Therapeutic Peptides and Proteins by Top-down Differential Mass Spectrometry and Metabolite Database Matching," Analytical Chemistry, vol. 92, pp. 8298-8305, 2020.

* cited by examiner

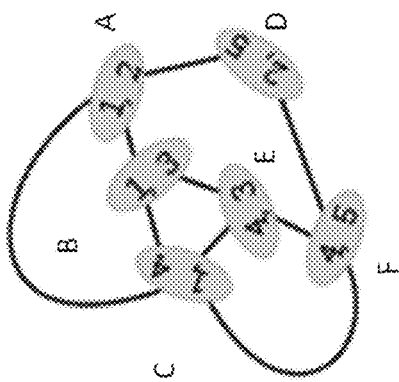
FIG. 9C
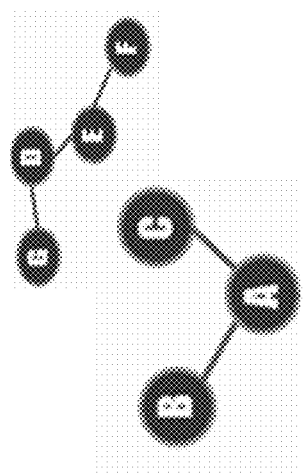
FIG. 9E
FIG. 9B
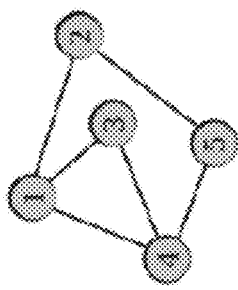
FIG. 9A
FIG. 9D

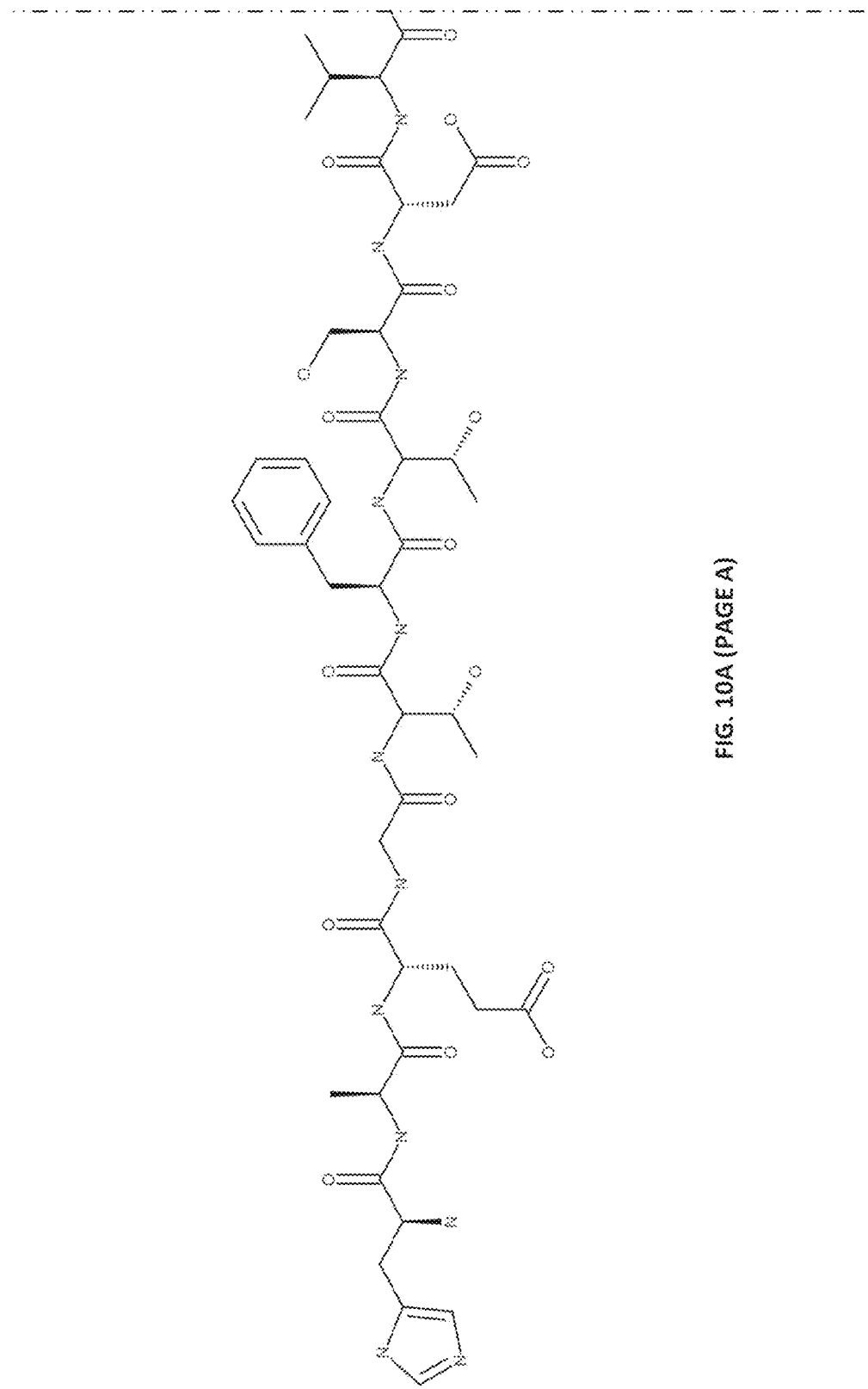
FIG. 10A (PAGE A)

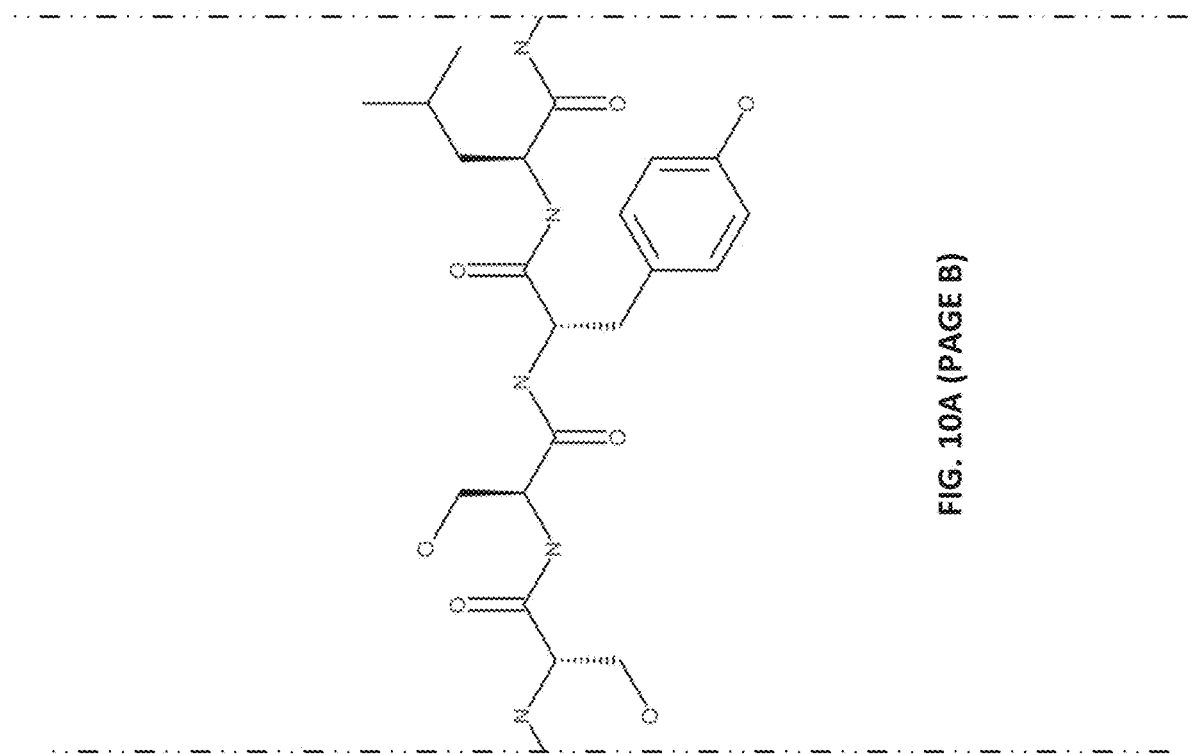
FIG. 10A (PAGE B)

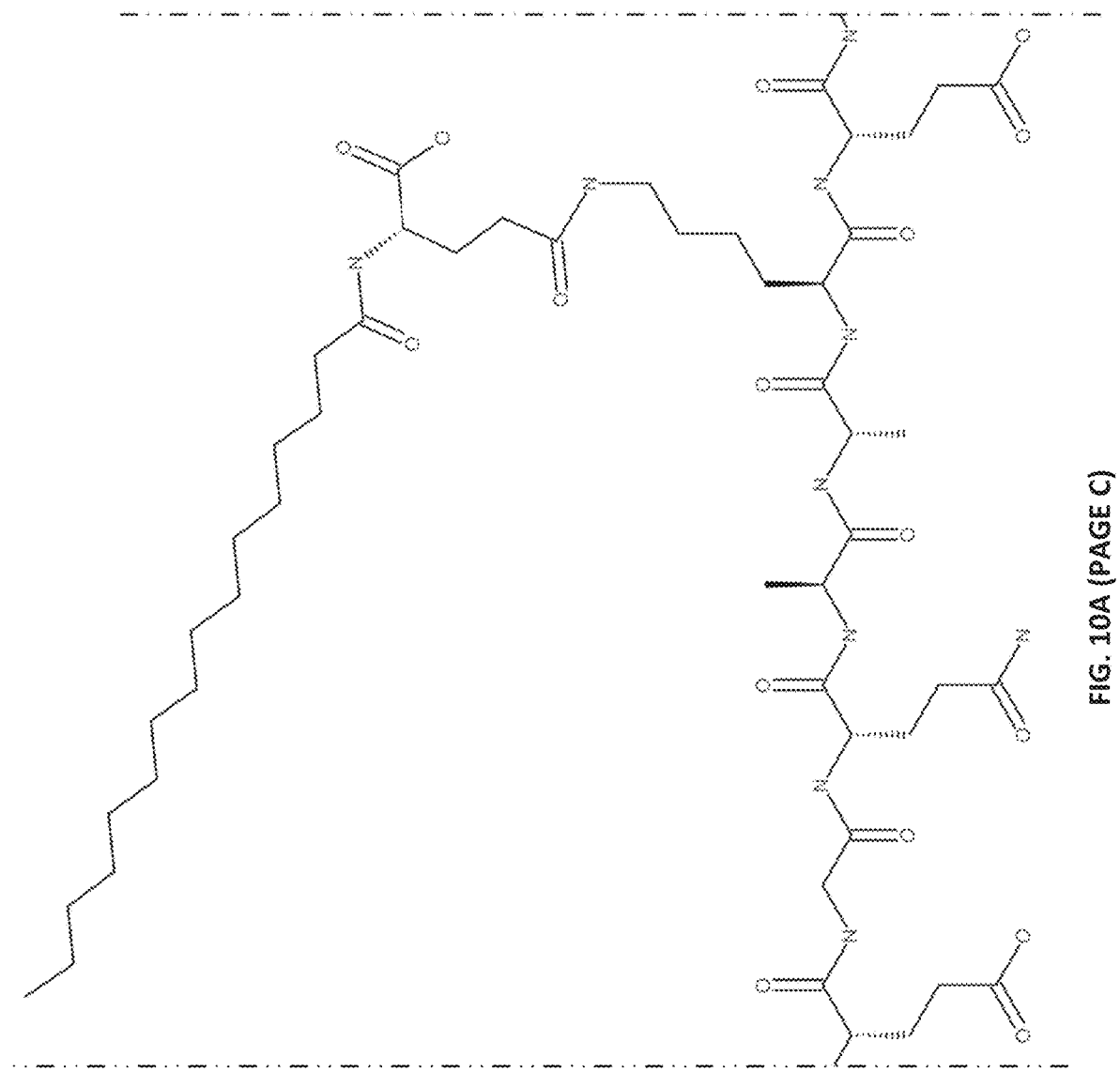
FIG. 10A (PAGE C)

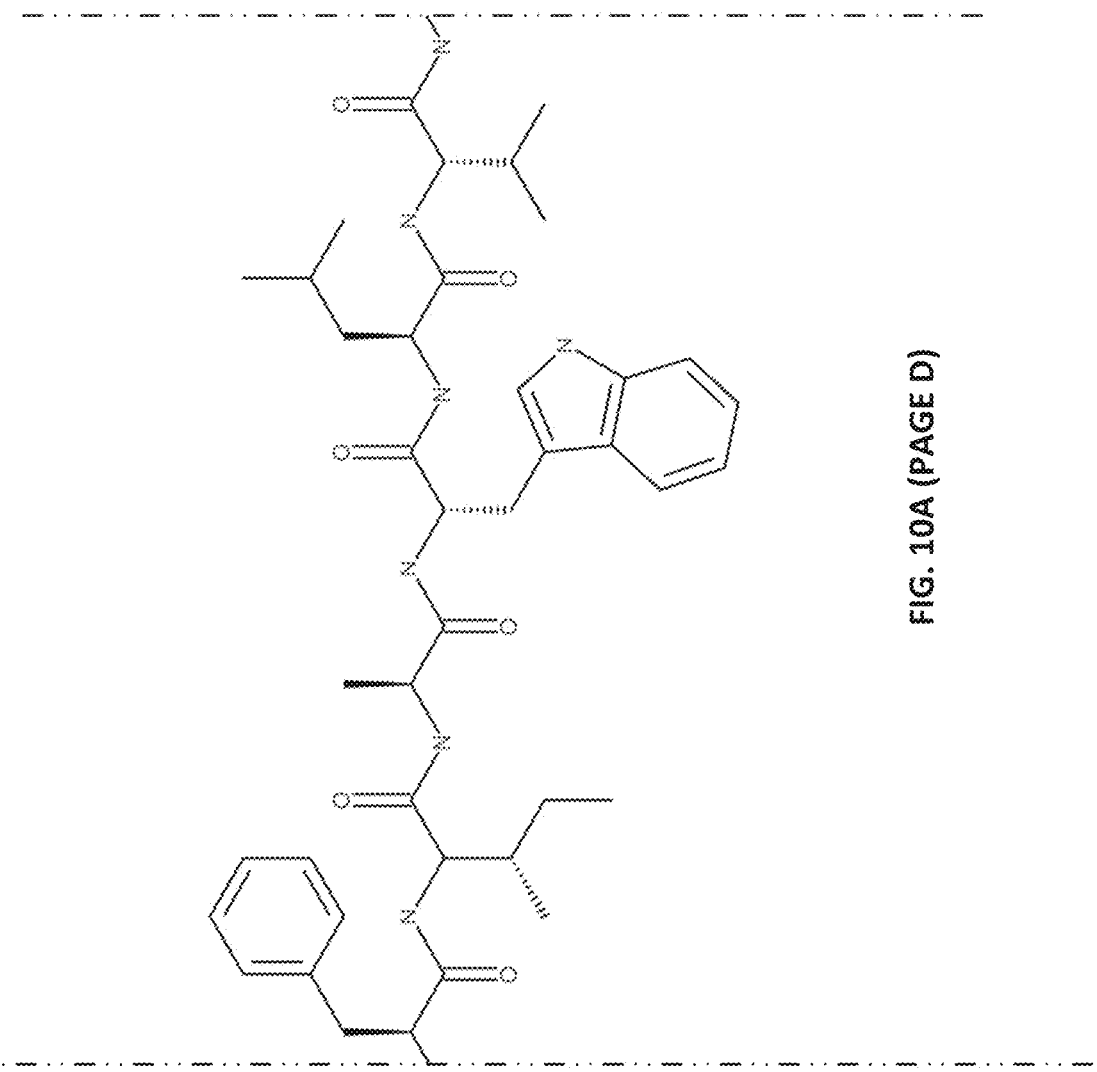
FIG. 10A (PAGE D)

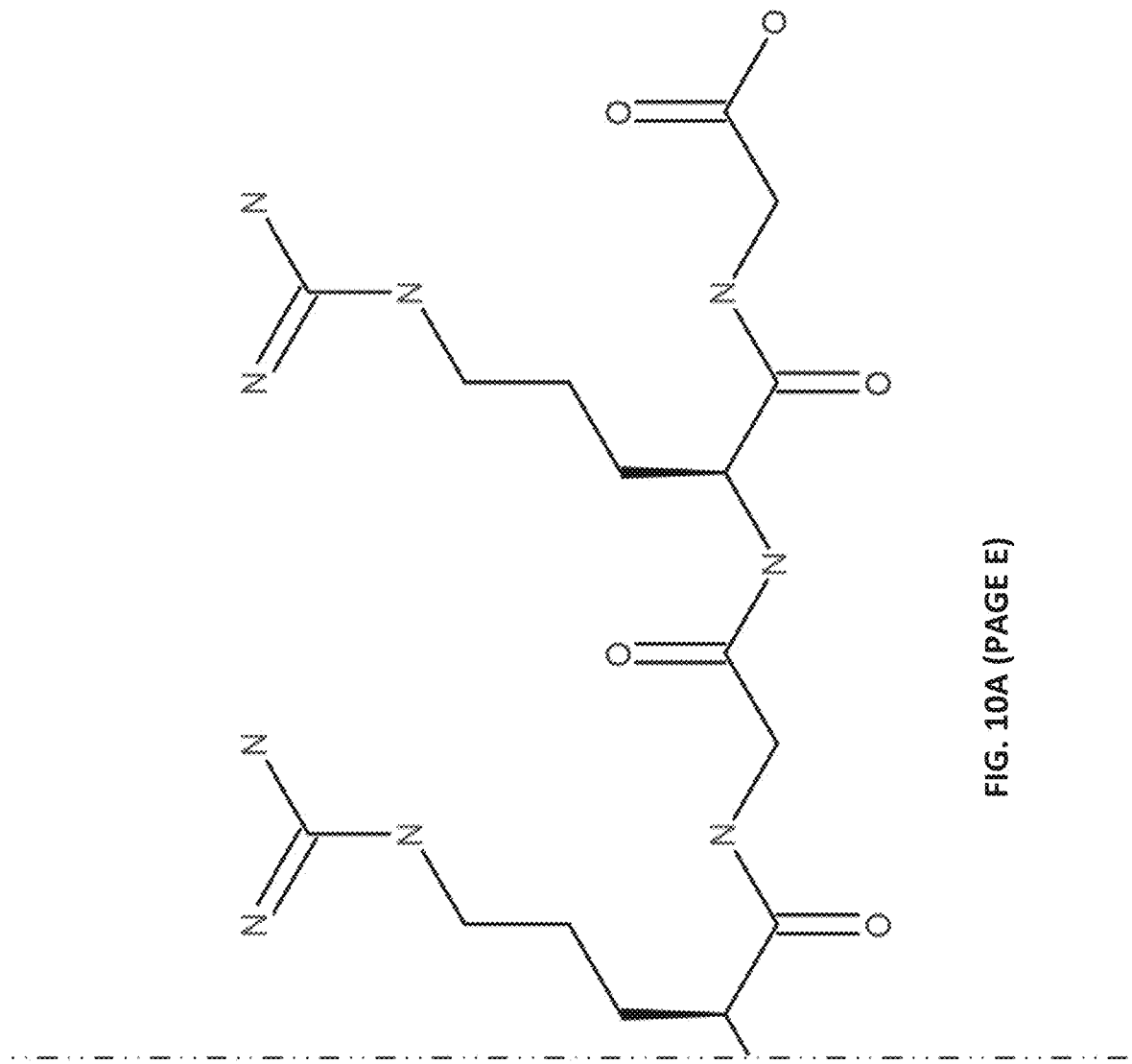
FIG. 10A (PAGE E)

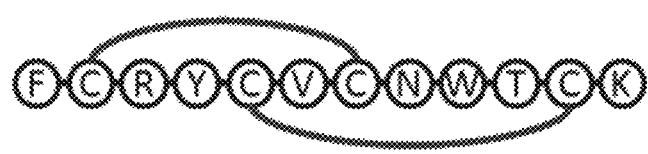
FIG. 12A
FIG. 12B
| | 1 | 2 | 3 | 4 | 5 | 6 | 7 | 8 | 9 | 10 | 11 | 12 |
|---|---|---|---|---|---|---|---|---|---|---|---|---|
| 1 | 0 | 1 | 0 | 0 | 0 | 0 | 0 | 0 | 0 | 0 | 0 | 0 |
| 2 | 1 | 0 | 1 | 0 | 0 | 0 | 1 | 0 | 0 | 0 | 0 | 0 |
| 3 | 0 | 1 | 0 | 1 | 0 | 0 | 0 | 0 | 0 | 0 | 0 | 0 |
| 4 | 0 | 0 | 1 | 0 | 1 | 0 | 0 | 0 | 0 | 0 | 0 | 0 |
| 5 | 0 | 0 | 0 | 1 | 0 | 1 | 0 | 0 | 0 | 0 | 1 | 0 |
| 6 | 0 | 0 | 0 | 0 | 1 | 0 | 1 | 0 | 0 | 0 | 0 | 0 |
| 7 | 0 | 1 | 0 | 0 | 0 | 1 | 0 | 1 | 0 | 0 | 0 | 0 |
| 8 | 0 | 0 | 0 | 0 | 0 | 0 | 1 | 0 | 1 | 0 | 0 | 0 |
| 9 | 0 | 0 | 0 | 0 | 0 | 0 | 0 | 1 | 0 | 1 | 0 | 0 |
| 10 | 0 | 0 | 0 | 0 | 0 | 0 | 0 | 0 | 1 | 0 | 1 | 0 |
| 11 | 0 | 0 | 0 | 0 | 1 | 0 | 0 | 0 | 0 | 1 | 0 | 1 |
| 12 | 0 | 0 | 0 | 0 | 0 | 0 | 0 | 0 | 0 | 0 | 1 | 0 |
FIG. 17C

|   | 1 | 2 | 3 | 4 | 5 | 6 | 7 | 8 | 9 | 10 | 11 | 12 | 13 |
|---|---|---|---|---|---|---|---|---|---|----|----|----|----|
| 1 | 0 | 1 | 0 | 0 | 0 | 0 | 0 | 0 | 0 | 0  | 0  | 1  | 0  |
| 2 | 1 | 0 | 1 | 0 | 0 | 0 | 0 | 0 | 0 | 0  | 0  | 1  | 0  |
| 3 | 0 | 1 | 0 | 1 | 0 | 0 | 0 | 0 | 0 | 0  | 0  | 0  | 0  |
| 4 | 0 | 0 | 1 | 0 | 1 | 0 | 0 | 0 | 0 | 0  | 0  | 0  | 1  |
| 5 | 0 | 0 | 0 | 1 | 0 | 1 | 0 | 0 | 0 | 0  | 0  | 0  | 1  |
| 6 | 0 | 0 | 0 | 0 | 1 | 0 | 1 | 0 | 0 | 0  | 0  | 1  | 0  |
| 7 | 0 | 0 | 0 | 0 | 0 | 1 | 0 | 1 | 0 | 0  | 0  | 1  | 0  |
| 8 | 0 | 0 | 0 | 0 | 0 | 0 | 1 | 0 | 1 | 0  | 0  | 0  | 0  |
| 9 | 0 | 0 | 0 | 0 | 0 | 0 | 0 | 1 | 0 | 1  | 0  | 0  | 0  |
| 10| 0 | 0 | 0 | 0 | 0 | 0 | 0 | 0 | 1 | 0  | 1  | 0  | 1  |
| 11| 0 | 0 | 0 | 0 | 0 | 0 | 0 | 0 | 0 | 1  | 0  | 0  | 0  |
| 12| 1 | 1 | 0 | 0 | 0 | 1 | 1 | 0 | 0 | 0  | 0  | 0  | 0  |
| 13| 0 | 0 | 0 | 1 | 1 | 0 | 0 | 0 | 0 | 1  | 1  | 0  | 0  |

FIG. 15A

| | A | B | C | D | E | F | G | H | I | J | K | L | M | N | O | P | Q | R | S | T | U | V | W | X | Y | Z | AA | AE |
|---|---|---|---|---|---|---|---|---|---|---|---|---|---|---|---|---|---|---|---|---|---|---|---|---|---|---|---|---|
| 1 | MW | | Vertex | | | | | | | | | | | | | Edges | | | | | | | | | | | | |
| 2 | 192.0569 | | 0 | 0 | 0 | 0 | 0 | 0 | 0 | 0 | 0 | 0 | 1 | 1 | 0 | 0 | 0 | 0 | 0 | 0 | 0 | 0 | 0 | 0 | 1 | 0 | 0 |
| 3 | 220.0882 | | 0 | 0 | 0 | 0 | 1 | 1 | 0 | 0 | 0 | 0 | 0 | 0 | 0 | 0 | 0 | 0 | 1 | 0 | 0 | 0 | 0 | 0 | 0 | 0 | 0 |
| 4 | 220.0882 | | 0 | 0 | 0 | 1 | 1 | 0 | 0 | 0 | 0 | 0 | 0 | 0 | 0 | 0 | 0 | 0 | 1 | 0 | 0 | 0 | 0 | 0 | 0 | 0 | 0 |

FIG. 15B

| mass | Vertex array | Edge array |
|---|---|---|
| 1271.4232 | 01 1110 11 0 11 1111 | 0 1110 01 1111 0 1 |
| 1271.4232 | 0 1110 11 0 11 1111 | 0 1110 01 1111 1 0 | mw = 220.882

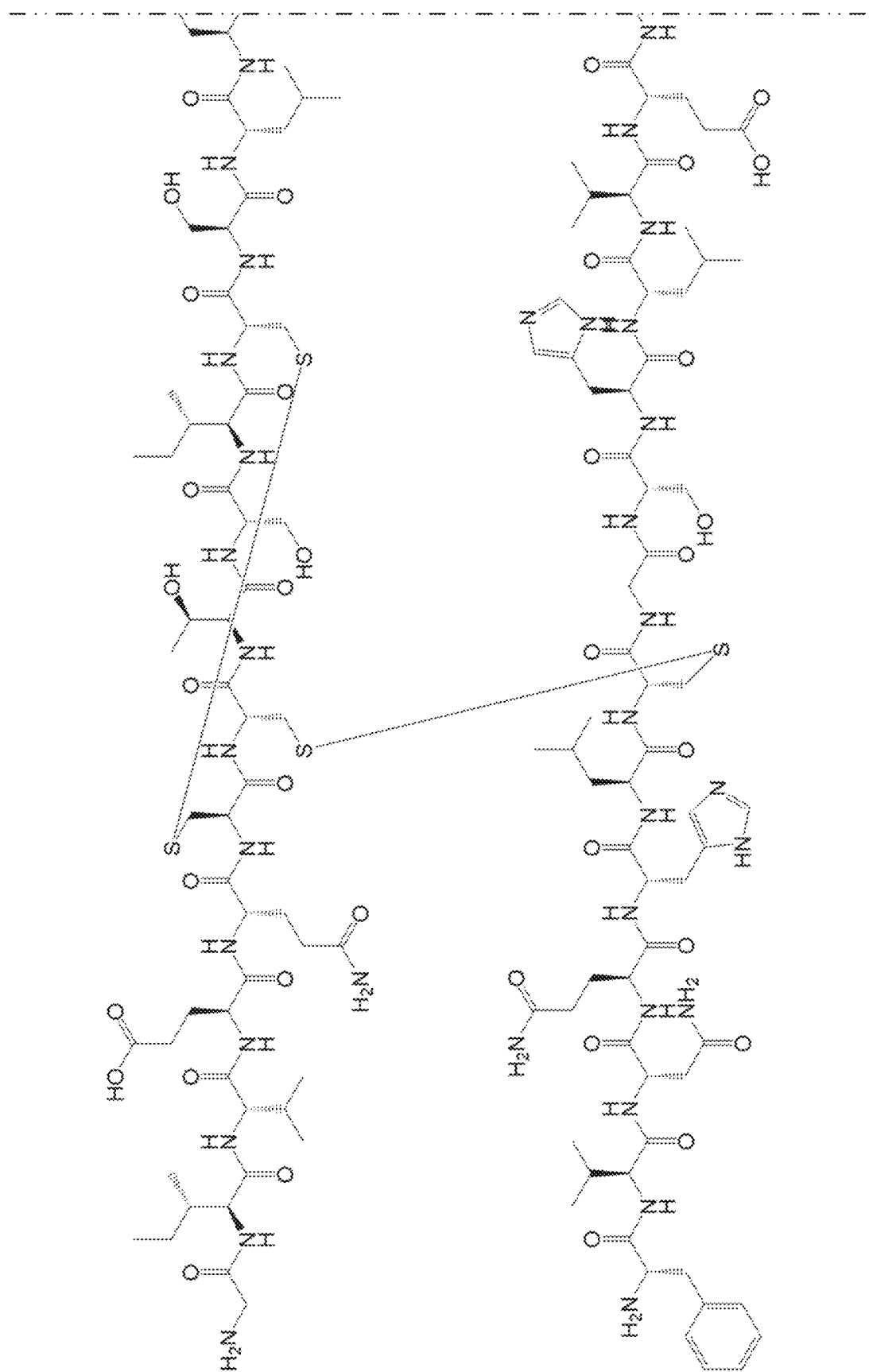
FIG. 22A (Page A)

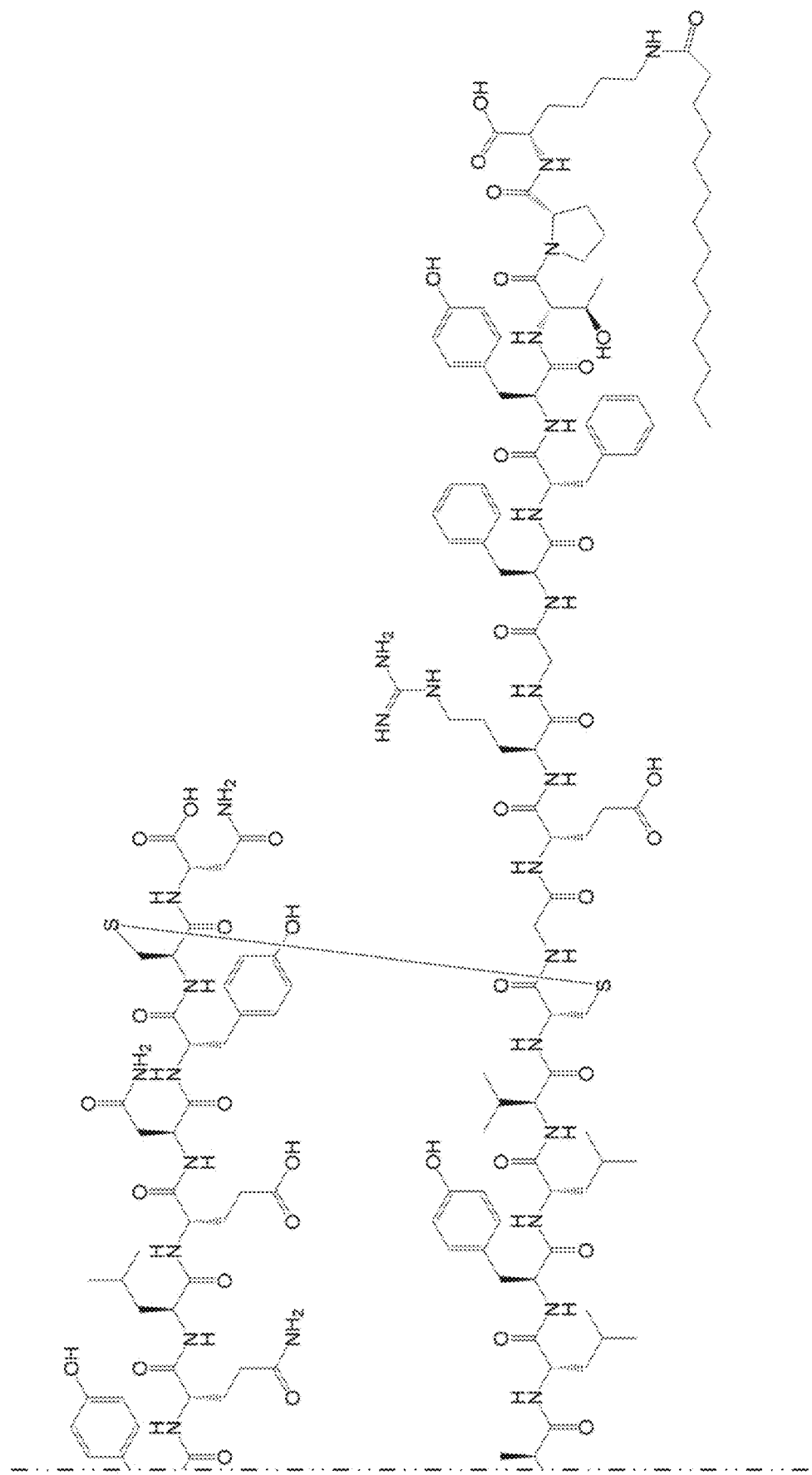
FIG. 22A (Page B)

FIG. 24

FIG. 26 (Page A)

FIG. 26 (Page B)

FIG. 27

```
order = 0; % "order" is the order in which a structure is entered into the database. "order" is incremented as the
database grows. When "order" reaches 10^6, or the hard drive is close to filling in, a warning is given that a
complete database cannot be constructed with the space available, and to please consider partitioning MCU graph
into several subgraphs for e=1:numberOfEdges % 8- START by adding each individual edge present in the structure, to the database. Just
the edge is added, with no neighbors. Therefore, the first several entries of the database will have a single "1" in the
Edge array and two "1"'s in the Vertex array (because each edge connects two vertices)

order = order+1; % increment "order" to track number of entries in database

Edges(e)=1; % "Edges" binary vector, initially all 0's, gets a 1 for edge e
    Vertices = E2V(e,:); % Vertices binary vector, initially all 0's, gets two elements set to 1, specifically those
vertices adjacent to edge "e"

% add substructure to database. The database is implemented as an
    % associative array, with edge indicator array acting as an index
    Record.Order = order;
    Record.Edges = Edges;
    Record.Vertices = Vertices
    SubstructureDatabase(Edges) = Record;

% recursively add DAUGHTER substructures of edge "e", to the database
    add_subgraphs(Edge_Occ, E2V(e,:), e, J(e,:));
    Edge_Occ(e)=0; % zero out Edge occurrence binary vector
end % for e end % main function add_subgraphs(parent_edge_subset,parent_edge_subset_str,parent_vert_subset, subset_min, neighbors)

% recursive step: For each substructure already in database ("parent substructure")
    -   identify its neighbors,
    -   add each ONE neighbor, one by one, to the parent substructure. This creates daughter substructures,
        that only differ from the parent substructure by one edge. Each daughter substructure is added to the
        database. The process repeats until there are no more substructures to add to the database.

for j=find(neighbors)
    child_edge_subset = parent_edge_subset;
    child_edge_subset(j)=1; % the only difference between child and parent subsets is one extra node
    if ~isKey(SubstructureDatabase,child_edge_subset_str)
        order = order+1;
        Record.Order = order;
        Record.Edges = child_edge_subset;
        % determine any new vertices
        f = find(E2V(j,:) & ~parent_vert_subset);
        child_vert_subset = parent_vert_subset;
        child_vert_subset(f)=1;
        Record.Vertices = child_vert_subset;
        SubstructureDatabase(child_edge_subset_str)=Record;
        neighbors_j = (neighbors | J(j,:)) & ~child_edge_subset
        add_subgraphs(child_edge_subset,child_edge_subset_str,child_vert_subset, subset_min, neighbors_j);
    end % if
end % for
end % function
```

Database entry   mass        5376.4044
                 Vertex array 1 1 1 1 1 1 1 1 1 1 0 1 1 1 1 1 1 1 1 1 1 1 1 1 1 1 1 1 1 1 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 0 0 0 1
                 Edge array   1 1 1 1 1 1 1 1 1 0 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 0 0 0 1 1 1

FIG. 30A

Database entry   mass        5376.4044
                 Vertex array 1 1 1 1 1 1 1 1 1 1 0 1 1 1 1 1 1 1 1 1 1 1 1 1 1 1 1 1 1 1 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 0 0 0 1
                 Edge array   1 1 1 1 1 1 1 1 1 0 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 0 0 0 1 1 1

FIG. 30B

Database entry   mass        5376.4044
                 Vertex array 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 0 1
                 Edge array   1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 0 1 1 1

FIG. 30C

Database entry   mass        5376.3945
                 Vertex array 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 0 0 1
                 Edge array   1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 1 0 0 0 0 1 1 1

FIG. 30D

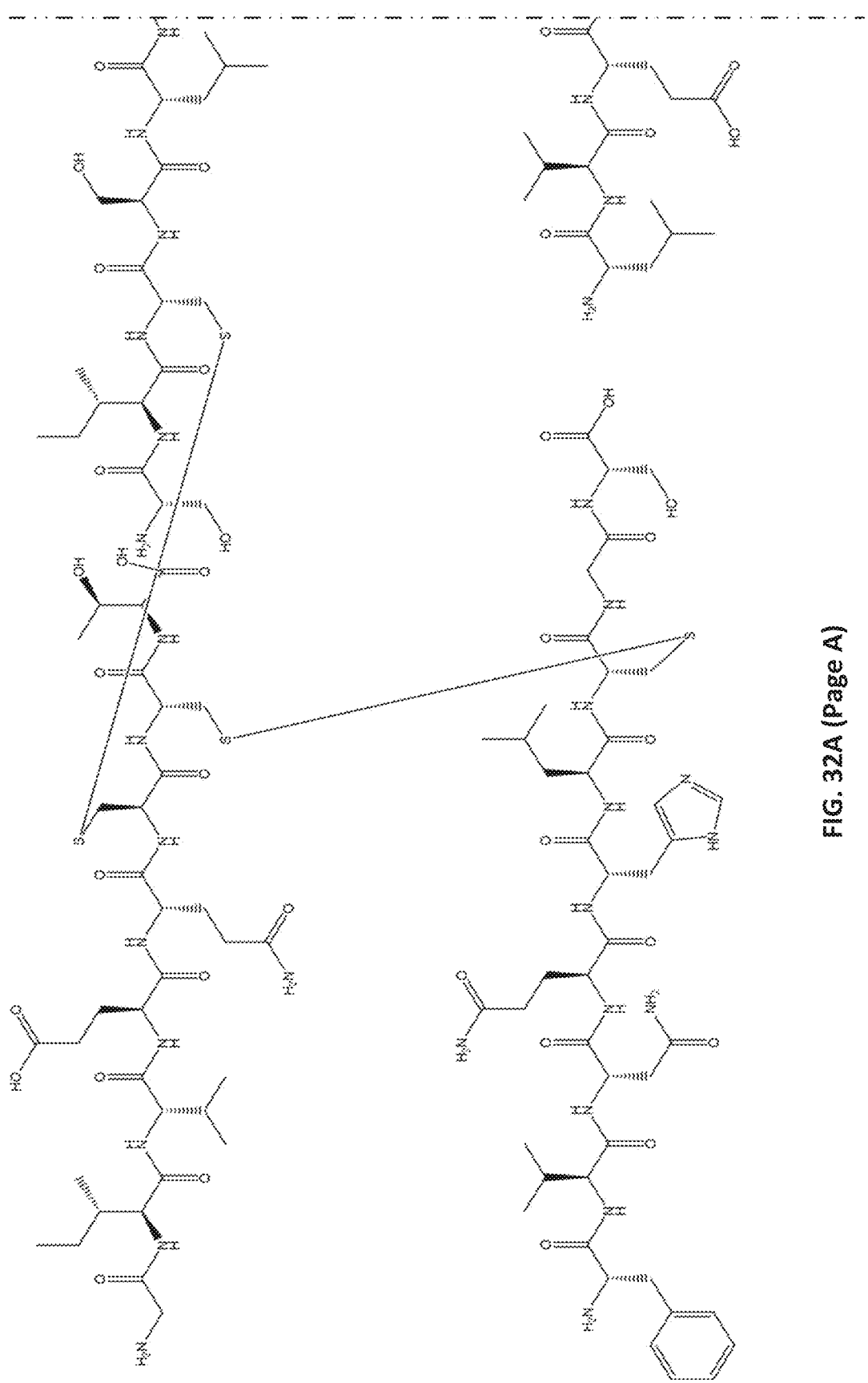
FIG. 32A (Page A)

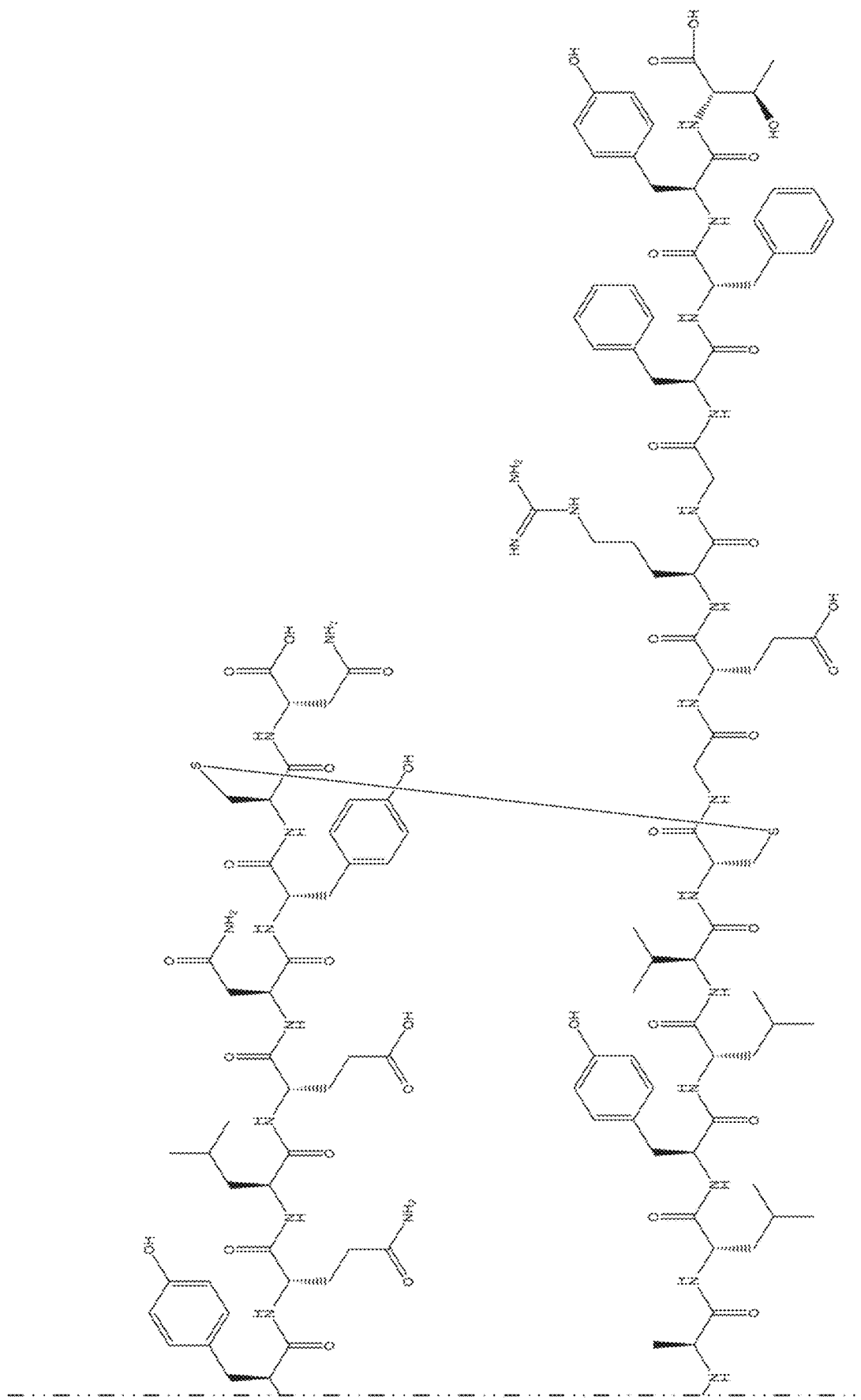
FIG. 32A (Page B)

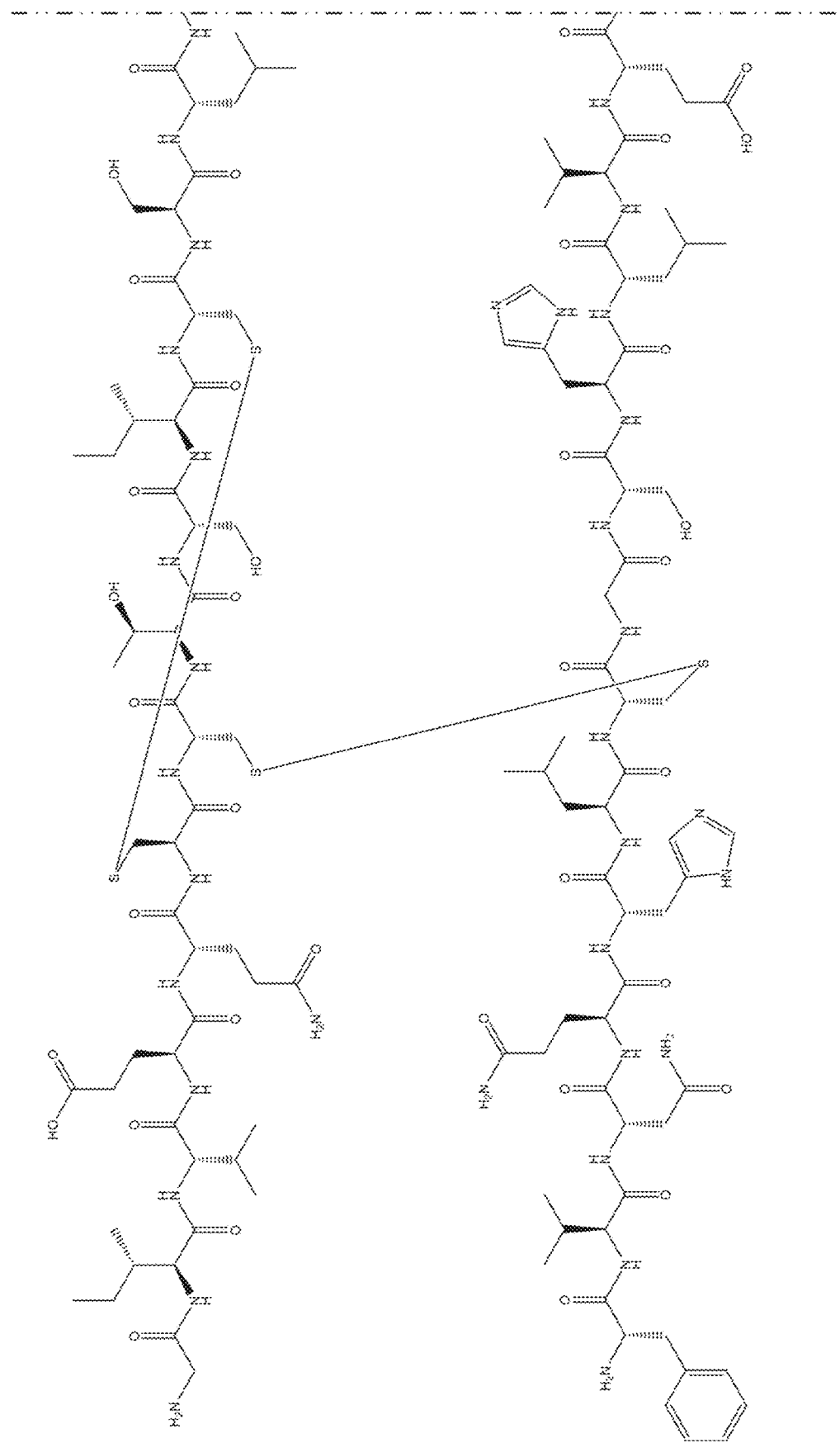
FIG. 33B (Page A)

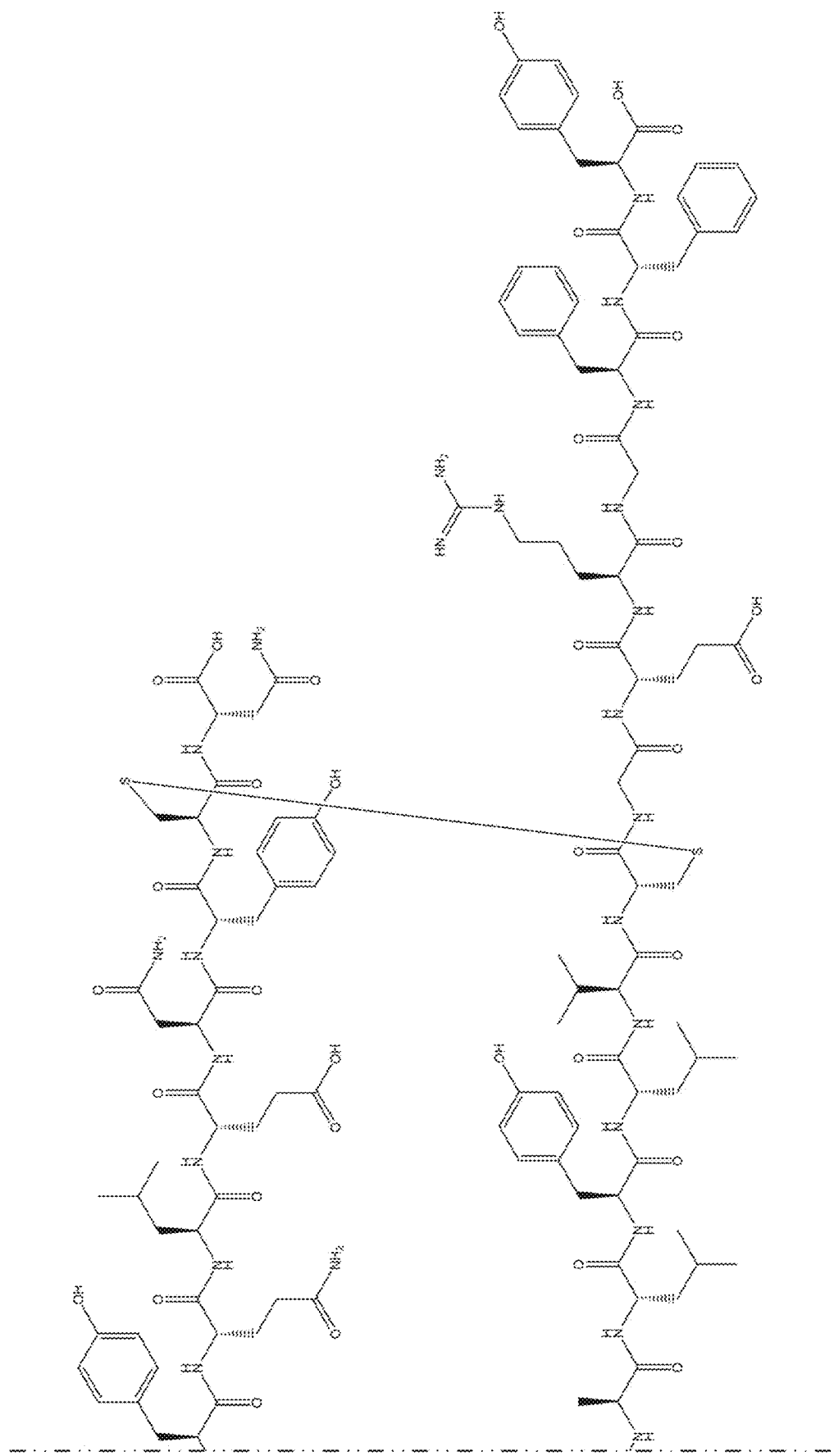
FIG. 33B (Page B)

COMPLEX MOLECULE SUBSTRUCTURE IDENTIFICATION SYSTEMS, APPARATUSES AND METHODS

FIELD OF THE INVENTION

The present invention relates to systems, apparatuses and methods for identifying substructures of complex molecules, particularly large molecules such as biomolecules.

BACKGROUND OF THE INVENTION

Identifying and characterizing substructures, such as metabolites, of pharmaceutical compounds is an important part of drug discovery and affect their biological activity, often resulting in metabolites with decreased bioavailability and enhanced toxicity. Understanding the structure of such metabolites and defining specific sites of metabolic transformations is useful, for example, in guiding synthetic optimization of the lead compounds or drug candidates to overcome the stability and toxicity issues.

Current metabolite identification (MetID) approaches have been unable to systematically characterize metabolites of large molecules, such as therapeutic proteins and peptides (TPPs) from biological matrices without prior knowledge of their structure. While some off the shelf small molecule MetID software, such as MASSCAP, SEQUEST and MassMetaSite are useful in characterizing metabolites of small molecule drugs and small linear peptides, this software has not been fully compatible with MetID of larger biomolecules, such as large non-linear peptides/proteins. There are at least three reasons: (i) most small molecule MetID software cannot properly deconvolute monoisotopic peaks for large molecules, which results in incorrect input mass values; (ii) most small molecule MetID software uses an atom-based algorithm designed for small molecule drugs, and the number of atoms of a typical large biomolecule, such as a TPP, is typically 1-2 orders of magnitude higher than for small molecules, which introduces a huge computational complexity for such atom-based algorithms; and (iii) information that is useful for small molecule MetID, such as cytochrome P450 metabolism pathways or mass defect filters, does not apply to large molecules, as large molecules have distinct metabolic processes, which are not generally accounted for in conventional small molecule software.

The computational complexity associated with atom-based representation of molecules can hinder computer analysis. Depending on the amount of RAM in a given computer, the processing required to identify all of the metabolites of a molecule having more than 10 million metabolites would likely bog down the computer. One gigabyte of RAM can, in the inventors' experience, handle about a million substructures. The number of theoretical metabolites for a given complex large molecule often exceeds 10 million.

In addition, conventional software for analyzing protein structure, for example, proteomics-based software, typically calculates amide and disulfide bond cleavages and has been unable to address the complete unpredictable metabolism profile of large molecules, such as TPPs, which includes unpredicted modifications (+Oxy, +P, +Met, etc), non-natural amino acids, in vivo disulfide scrambling, non-natural linkers and nonspecific proteolytic cleavages.

Thus, there is a need for systems and processes that are capable of decoding nonlinear peptides and large molecules and for systems and methodology that not only facilitate differentiating metabolites of large molecules, such as therapeutic peptides or proteins, from the proteinaceous background in the biological matrix, but also facilitates elucidation of the structure of metabolites of interest. There is also considerable need for systems and processes that generate and display the structures of large molecule metabolites.

SUMMARY OF THE INVENTION

Embodiments of the present invention address the above-described need by providing systems, apparatuses and methods for identifying substructures, such as metabolites, of molecules, and particularly the substructures of large molecules, such as biomolecules that have heretofore been difficult to identify and characterize. Indeed, data interpretation has been and continues to be the bottleneck for current peptide/protein metabolite identification.

The invention is applicable and useful for identifying substructures for all types of molecules. A chosen molecule may be a large molecule, or macromolecule, or a small molecule. Macromolecules include, but are not limited to amino acid based molecules, such as peptides, polypeptides, antibodies, proteins, enzymes, immunoglobulins, lipids, nucleic acids, carbohydrates, oligonucleotides, polynucleotides, polysaccharides and polymers. A chosen molecule may also be a conjugated molecule and a cross-linked molecule.

Small molecules include organic molecules that have a relatively low molecular weight, whether naturally-occurring or artificially created (e.g., via chemical synthesis). Embodiments of the present invention are useful for analyzing small molecules that are biologically active in that they produce a local or systemic effect in animals, preferably mammals, more preferably humans. In certain embodiments, the small molecule has a molecular weight of less than or equal to about 900 Daltons.

In general, embodiments of the present invention may be used by scientists, such as chemists and biochemists, to identify metabolites and other substructures of complex molecules, and to determine the associated chemical structures of such metabolites and other substructures. As such, embodiments of the present invention may be considered to be extremely useful in drug development and design.

As used herein, all amino acid three letter and single letter designations conform to those designations which are standard in the art, and are listed as follows:

Alanine Ala A Arginine Arg R Asparagine Asn N Aspartic acid Asp D Cysteine Cys C Glutamic acid Glu E Glutamine Gln Q Glycine Gly G Histidine His H Isoleucine Ile I Leucine Leu L Lysine Lys K Methionine Met M Phenylalanine Phe F Proline Pro P Serine Ser S Threonine Thr T Tryptophan Trp W Tyrosine Tyr Y Valine Val V Exemplary systems, apparatuses and methods of the invention combine small molecule MetID and Top Down proteomics approaches and provide a rapid and efficient way to not only identify and store the exhaustive pool of substructures, such as metabolites, of a given molecule, but to also provide structural characterization of the identified metabolites and visualization of the chemical structure or makeup of the metabolites. Exemplary systems, apparatuses and methods of the invention improve the operation of a conventional computer system by significantly improving search times required for the computer system to identify and characterize substructures and metabolites of complex molecules. Computer systems configured to operate according to embodiments of the present invention can identify and characterize hundreds of millions of substructures in a matter of hours, as compared to conventional computerized methods which would take weeks or months. The substructures may be stored in an electronic medium, such as a computer memory, displayed on the computer monitor, printed, or transmitted to another computer system for further analysis. The significantly reduced processing times enabled by the present invention will play an valuable and practical role in advancing the art of drug design and development.

The molecule to which the substructures belong are referred to as "the chosen molecule." The present invention employs a unique system for representing the chosen molecules. Specifically, a chosen molecule is described in terms of a defined minimum cleavable unit (referred to herein as an MCU), which is represented by a graph referred to as a minimum cleavable unit graph (an MCU graph). The MCU graph is in turn represented by data stored in data structure in the memory of a computer system. A minimum cleavable unit, as recited herein, is a part of a molecule where no cuts/cleavage (no metabolic process) is allowed to take place. The minimum cleavable unit may comprise a group of atoms between adjacent metabolic cleavage sites of a chosen molecule. By way of example, a minimum cleavable unit for a protein or peptide molecule may comprise a single amino acid, or a stretch of amino acids, for example. A minimum cleavable unit of a cyclic peptide may comprise a core region of the cyclic peptide, for example. The minimum cleavable unit approach facilitates defining molecules of interest in a simpler manner, for example, by reducing the complexity of a complex protein structure by attempting to reduce it to linear peptide realm. The minimum cleavable unit approach allows the user to define a module that eliminates follow up on metabolites that have cleavages within the MCU and are therefore not functional.

A chosen molecule may have many different MCU graphs, depending on the goal of a given study and how the MCU is defined. For example, if the goal of the study is to identify all metabolites generated by amide bond cleavages, then the MCU is defined as each individual amino acid residue, because the user will consider no further metabolism beyond single amino acids. As another example, if the goal of a study is to identify active metabolites of a cyclic peptide, the cyclic region of the peptide would also be included as an MCU, since an active metabolite must have an intact cyclic region, and no further metabolism needs to be considered within the cyclic region.

Researchers and scientists have heretofore failed to recognize that line graphs derived from MCU graphs are an efficient way to identify substructures, such as metabolites, of molecules. The present inventors have discovered that line graphs are particularly useful as substructure identification systems, apparatuses and methods. Importantly, the present inventors recognized that the universe of induced connected subgraphs of a line graph of an MCU graph completely and uniquely represents the entire universe of substructures and metabolites for the molecule represented by the corresponding MCU graph. In other words, there is a one-to-one relationship between the set of induced connected subgraphs of a line graph of an MCU graph and the set of metabolites for the molecule represented by the corresponding MCU graph. This relationship is actionable because it permits using an algorithm to identify the entire universe of metabolites of the chosen molecule. Practical application of the algorithm significantly improves the functioning of computer systems used to identify the entire universe of metabolites for the chosen molecule.

In a first phase of operation for one embodiment of the invention, the user inputs chosen molecule data, comprising (A) a set of minimum cleavable units for the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween. The chosen molecule data may be provided in the form of an MCU graph of the chosen molecule or another representation of a chosen molecule, such as a chemical structure or drawing with vertex and edge annotations that include identification of MCUs, the types of bonds connecting the MCUs and the molecular weights of MCUs. The system uses this input to populate an MCU graph data structure for the chosen molecule. Suitable MCU graph data structures include arrays, adjacency matrices, adjacency lists, incidence matrices or incidence lists.

Based on the MCU graph data structure, the system then generates a different representation of the chosen molecule, namely a line graph, and stores data representing the line graph in a line graph data structure, which is particularly useful in the substructure identification process of the invention as will be described in more detail below. Suitable line graph data structures also include adjacency matrices, adjacency lists, incidence matrices or incidence lists.

The system then traverses the line graph data structure using a suitable graph traversal algorithm (shown in FIG. 27) to identify a complete set of induced connected subgraphs (ICS) of the chosen molecule. Suitable graph traversal algorithms include a depth-first search algorithm, or a breadth-first search algorithm, or a reverse-search algorithm, or a tree-search algorithm, or a combination of two of more of the graph traversal algorithms recited herein. For each ICS, the system creates and populates an ICS record containing a molecular weight field, a vertex data field and an edge data field. The system then calculates and stores the total molecular weight corresponding to each induced connected subgraph and stores the molecular weight in the molecular weight field alongside the vertex and edge data for each ICS record, so that each record can be subsequently searched for and found by molecular weight. The data stored in each one of the ICS records represents a substructure of the chosen molecule. In some embodiments, the system may also be configured to calculate and store in each ICS record the number of biotransformations (i.e., broken covalent bonds) that would have to occur for the chosen molecule to be transformed into the substructure of the chosen molecule.

In a second phase of operation, the system receives a molecular weight from a user (who may or may not be the first user), wherein the molecular weight entered is predetermined by the user, either by experimentation or obtained from another source or device, such as a mass spectrometer. The system searches the ICS records that are stored in the database and contain ICS molecular weight, vertex array values and edge array values, to find an ICS record that has a molecular weight that matches the query molecular weight, and if found, displays, prints or transmits information in the ICS record to the user. Optionally, the system may also display, print or transmit a graphical representation of the structure of the matching induced connected subgraph based on the vertex and edge data in each record. Preferably, the substructures matching the given query molecular weight are listed and/or displayed in ranked order according to the number of biotransformations that would have to occur for the chosen molecule to be transformed into the matching substructure.

The substructure identification systems, apparatuses and methods of the present invention are useful for identifying metabolites of a chosen molecule as well as other substructures of a chosen molecule. For example, to characterize an intact protein, gas fragmentation techniques are often carried out to obtain fragment ions of the precursor protein ion. Each fragment ion may be viewed as a substructure of the precursor ion. In order to correctly characterize the structure of the precursor protein ion, the structure of each fragment ion needs to be correctly assigned based on its mass or molecular weight value. The systems, apparatuses and methods of the present invention may be applied to build the relationship between mass values of the fragment ions and their structures in the gas phase.

In one aspect, the invention provides a system for identifying substructures of a chosen molecule, the system comprising a) a microprocessor, b) a memory, c) an application program in the memory, d) a user interface for communication with an end user. The application program comprises program instructions that, when executed by the microprocessor, will cause the microprocessor to (i) receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween; (ii) based on the chosen molecule data, create and store in the memory a minimum cleavable unit graph data structure for the chosen molecule, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule; (iii) based on the MCU graph data, generate and store in the memory a line graph data structure, the line graph data structure being populated with line graph data representing a line graph for the MCU graph, the line graph having a plurality of line graph (LG) vertices and a plurality of line graph (LG) edges, each LG vertex corresponding to an MCU graph edge in the MCU graph and each LG edge corresponding to a pair of MCU graph vertices in the MCU graph that are connected together by said MCU graph edge; (iv) execute a graph traversal algorithm against the line graph data in the line graph data structure to determine a plurality of induced connected subgraphs for the line graph. Each induced connected subgraph comprises a connected subset of LG vertices and LG edges in the line graph, and a physical arrangement of said connected subset of LG vertices and LG edges, wherein the connected subset of LG vertices and LG edges and the physical arrangement thereof together uniquely corresponds to a connected subset of the set of minimum cleavable units and bonds, and the relative positions of said connected subset of minimum cleavable units and bonds in the chosen molecule.

The application program further comprises program instructions that, for each induced connected subgraph represented in the line graph data structure, create in the database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate the edge position of every LG edge in the induced connected subgraph relative to the LG vertices. For each ICS record in the line graph data structure, the application program calculates and stores in the molecular weight field a total molecular weight for the induced connected subgraph of that ICS record based on elemental molecular weights provided by the chosen molecule data for the chosen molecule and the vertex values and the edge values in the ICS record. Preferably, the system also calculates and stores in each ICS record the number of biotransformations (i.e., the biotransformation count) that would be required to transform the chosen molecule into the substructure represented by the vertex data, the edge data and the molecular weight for that ICS record. Storing the biotransformation counts alongside the other data in each ICS records permits searching and/or ranking the search results according to the biotransformation counts.

The user interface comprises program instructions that, when executed by the microprocessor, will cause the microprocessor to (i) receive a query molecular weight from the end user; (ii) search the database based on the query molecular weight to identify an ICS record having a total molecular weight in the molecular weight field that matches the query molecular weight, and (iii) transmit the vertex values in the vertex data field and the edge values in the edge data field for the identified ICS record to the user interface for presentation on a display device operated by the end user.

In some embodiments of the invention, the system further comprises program instructions in the user interface that, when executed by the microprocessor, will cause the microprocessor to a) use the vertex values in the vertex data field, the edge values in the edge data field and the chosen molecule data to produce in the memory of the computer system a graphical representation from the computer systems memory of an induced connected subgraph of the line graph; and (ii) transmit the graphical representation to the display device operated by the end user.

In additional embodiments of the invention, the system further comprises program instructions in the application program that, when executed by the microprocessor, causes the microprocessor to a) receive a specified tolerance for the molecular weight, b) use the specified tolerance to calculate and define a range of molecular weights for the search of the database, c) search the database based on the query molecular weight and the range to identify each ICS record in the database that has a total molecular weight in the molecular weight field that falls within the defined range of molecular weights, and d) for said each identified ICS record, transmit the vertex values in the vertex data field and the edge values in the edge data field to the user interface for presentation to the end user on the end user's display device. Preferably, the program instructions of the application program are further configured to rank the search results and display them in order of ascending biotransformation counts, so that the induced connected subgraphs requiring the least number of biotransformations are displayed first (i.e., at the top of the list and before the matching induced connected subgraphs requiring higher numbers of biotransformations.

In some embodiments of the invention, the chosen molecule data is obtained by executing instructions in the application, which are configured to parse information stored in the memory of the computer system as a linked list, or an array, or an adjacency matrix, or a graphic image file, or a chemical drawing file (for example ChemDraw® file from Cambridge Soft®, PerkinElmer, Inc., Waltham, Mass., USA), or a spreadsheet file, or a text file, or a CSV file, or a .CDX file, or a .CDXML file, or a .MOL file, or a .SDM file, or a CAD file, or a binary data file, or a .SMI file, or a HELM file, or a .CHELM file, or a .XHELM file.

The connected subset of the set of minimum cleavable units and bonds is a metabolite of the chosen molecule, or a catabolite of the chosen molecule, or a gas phase fragmentation of the chosen molecule, or a degradant of the chosen molecule, or a substructure of the chosen molecule.

In some embodiments of the invention, a) the chosen molecule data includes elemental composition data representing (A) a set of elemental units in each minimum cleavable unit, (B) a set of elemental bonds connecting the set of elemental units in the minimum cleavable unit, (C) elemental molecular weights for each elemental unit, and (D) an MCU connectivity profile for the minimum cleavable unit, the MCU connectivity profile indicating relative positions of elemental units and elemental bonds in the minimum cleavable units and connections therebetween. In these embodiments, the ICS record created in the database further comprises an elemental unit field populated with one or more elemental unit identifiers. The application program further includes program instructions that, when executed by the microprocessor, will cause the microprocessor to (a) receive a query elemental unit from the end user, (ii) search the database based on the query elemental unit to identify an ICS record having an elemental unit identifier in the elemental unit field that matches the query elemental unit, and (iii) transmit the vertex values in the vertex data field and the edge values in the edge data field for the identified ICS record to the user interface for presentation on a display device operated by the end user.

In another aspect, the invention provides a system for generating a database to facilitate identifying substructures of a chosen molecule using a microprocessor, the system comprising: a) a memory, b) a microprocessor, c) an input module for receiving and storing chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the minimum cleavable units and the bonds in the chosen molecule, the connectivity profile indicating relative positions of minimum cleavable units and bonds and connections therebetween, d) an MCU graph module configured to create in the memory a minimum cleavable unit graph data structure for the chosen molecule based on the chosen molecule data, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule, e) a line graph module configured to generate and store in the memory a line graph data structure populated with line graph data representing a line graph for the MCU graph, the line graph having a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge, f) a graph traversal module configured to run a graph traversing algorithm against the line graph data in the line graph data structure to determine a plurality of induced connected subgraphs for the line graph, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule; and g) a subgraph database generator that (i) for each induced connected subgraph represented in the line graph data structure, creates in the database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate the edge position of every LG edge in the induced connected subgraph relative to the LG vertices, and (ii) for each ICS record in the line graph data structure, calculates and stores in the molecular weight field a total molecular weight for the induced connected subgraph of that ICS record based on the chosen molecule data for the chosen molecule and the vertex values and the edge values in the ICS record.

The system further includes a user interface in the memory for communication with an end user, and a search engine in the memory, both having program instructions that, when executed by the microprocessor, will cause the microprocessor to (i) receive a query molecular weight from the end user, (ii) search the database based on the query molecular weight to identify an ICS record having a total molecular weight in the molecular weight field that matches the query molecular weight; and (iii) transmit the vertex values in the vertex data field and the edge values in the edge data field for the identified ICS record to the user interface for presentation on a display device operated by the end user.

In some embodiments of the invention, the user interface further comprises program instructions that, when executed by the microprocessor, will cause the microprocessor to a) use the vertex values in the vertex data field, the edge values in the edge data field and the chosen molecule data to produce a graphical representation of an induced connected subgraph of the line graph; and b) transmit the graphical representation to the display device operated by the end user.

In some embodiments of the invention, the application program further comprises program instructions that, when executed by the microprocessor, causes the microprocessor to a) receive a specified tolerance for the molecular weight, b) use the specified tolerance to calculate and define a range of molecular weights for the search of the database, c) search the database based on the query molecular weight and the range to identify each ICS record in the database that has a total molecular weight in the molecular weight field that falls within the defined range of molecular weights, and d) for said each identified ICS record, transmit the vertex values in the vertex data field and the edge values in the edge data field to the user interface for presentation to the end user.

In another aspect, the invention provides a method for generating a database to facilitate identifying substructures of a chosen molecule using a microprocessor and a memory device. The method comprises the steps of: a) receiving and storing in the memory device chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween, b) based on the chosen molecule data, creating and storing in the memory device a minimum cleavable unit graph data structure for the chosen molecule, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule; c) based on the MCU graph data, generating and storing in the memory device a line graph data structure, the line graph data structure being populated with line graph data representing a line graph for the MCU graph, the line graph having a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge, d) executing on the microprocessor a graph traversal algorithm against the line graph data in the line graph data structure to determine a plurality of induced connected subgraphs for the line graph, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule. For each induced connected subgraph represented in the line graph data structure, the method further comprises the steps of e) creating in the database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate the edge position of every LG edge in the induced connected subgraph relative to the LG vertices, and f) for each ICS record in the line graph data structure, calculating and storing in the molecular weight field a total molecular weight for the induced connected subgraph of that ICS record based on the chosen molecule data for the chosen molecule and the vertex values and the edge values in the ICS record.

In some embodiments of the invention, the method further comprises a) producing with the microprocessor a graphical representation of an induced connected subgraph of the line graph based on the connectivity profile of the chosen molecule, the vertex values in the vertex data field and the edge values in the edge data field; and b) transmitting the graphical representation to the display device.

In an additional aspect, the invention provides a system for generating a database to facilitate identifying a substructure of a chosen molecule using adjacency matrices. In this aspect, the system comprises a) a microprocessor, b) a memory device and c) program instructions that cause the microprocessor to (i) receive data representing a chemical diagram of the chosen molecule and annotations that identify (A) minimum cleavable units of the chosen molecule, (B) molecular weights of each minimal cleavable unit of the chosen molecule, and (C) types of bonds connecting minimum cleavable units of the chosen molecule, (ii) generate a minimum cleavable unit graph adjacency matrix of the chosen molecule, the minimum cleavable unit graph adjacency matrix having a plurality of records, each record corresponding to a pair of vertices and having a field that is assigned a first value where an edge exists between the pair or a second value where an edge does not exist between the pair, each vertex corresponding to a minimum cleavable unit of the chosen molecule, wherein an edge represents a bond connecting minimum cleavable units of the chosen molecule, (iii) generate a line graph adjacency matrix from the minimum cleavable unit graph adjacency matrix, the line graph adjacency matrix having a plurality of vertices, each vertex corresponding to a pair of edges of the minimum cleavable unit graph adjacency matrix and having a field that is assigned the first value where an endpoint exists between the pair of edges or a the second value where no endpoint exists between the pair of edges, the line graph adjacency matrix having a vertex for each edge of the minimum cleavable unit graph adjacency matrix based upon endpoints connected by the edge, wherein vertices represent bonds between the minimum cleavable units of the chosen molecule, (iv) generate an edge to vertex adjacency matrix from the minimum cleavable unit adjacency matrix, the edge to vertex adjacency matrix having a plurality of elements, each element corresponding to an edge and a vertex of the minimum cleavable unit graph adjacency matrix and having a field that is assigned the first value where the edge and the vertex are connected to each other or the second value where the edge and the vertex are not connected to each other, the vertices representing minimum cleavable units of the chosen molecules and the edges representing bonds connecting the minimum cleavable units of the chosen molecule, (v) traverse the line graph adjacency matrix and the edge to vertex graph adjacency matrix using a graph traversal algorithm to determine a plurality of induced connected subgraphs for the chosen molecule, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule; and (vi) calculate and store in said database a molecular weight for each of the induced connected subgraphs, wherein the molecular weight for each induced connected subgraph is calculated by retrieving and summing together the molecular weights of every vertex of the induced connected subgraph.

In another aspect, the invention provides a system for generating a database to facilitate identifying a substructure of a chosen molecule using a microprocessor, the system comprising a) a graphical input module to receive a chemical diagram of the chosen molecule and annotations that identify (A) minimum cleavable units of the chosen molecule, (B) molecular weights of each minimal cleavable unit of the chosen molecule, and (C) types of bonds connecting minimum cleavable units of the chosen molecule, b) a matrix generator module to generate a minimum cleavable unit graph adjacency matrix of the chosen molecule, the minimum cleavable unit graph adjacency matrix having a plurality of records, each record corresponding to a pair of vertices and having a field that is assigned a first value where an edge exists between the pair or a second value where an edge does not exist between the pair, each vertex corresponding to a minimum cleavable unit of the chosen molecule, wherein an edge represents a bond connecting minimum cleavable units of the chosen molecule, c) a line graph matrix generator module to generate a line graph adjacency matrix from the minimum cleavable unit graph adjacency matrix, the line graph adjacency matrix having a plurality of vertices, each vertex corresponding to a pair of edges of the minimum cleavable unit graph adjacency matrix and having a field that is assigned the first value where an endpoint exists between the pair of edges or a the second value where no endpoint exists between the pair of edges, the line graph adjacency matrix having a vertex for each edge of the minimum cleavable unit graph adjacency matrix based upon endpoints connected by the edge, wherein vertices represent bonds between the minimum cleavable units of the chosen molecule, d) an edge to vertex matrix generator module to generate an edge to vertex matrix from the minimum cleavable unit adjacency matrix, the edge to vertex matrix having a plurality of elements, each element corresponding to an edge and a vertex of the minimum cleavable unit graph adjacency matrix and having a field that is assigned the first value where the edge and the vertex are connected to each other or the second value where the edge and the vertex are not connected to each other, the vertices representing minimum cleavable units of the chosen molecules and the edges representing bonds connecting the minimum cleavable units of the chosen molecule, e) a graph traversing engine that traverses the adjacency matrix and the edge to vertex matrix using a depth first or breadth first search to produce and store in a database induced connected subgraphs of the line graph adjacency matrix based on the value assignments in the line graph adjacency matrix and the edge to vertex matrix, and f) a molecular weight calculator module that calculates and stores in the database a molecular weight for each induced connected subgraph, wherein the molecular weight for each induced connected subgraph is calculated by retrieving and summing together the molecular weights of every vertex of the induced connected subgraph.

In yet another aspect, the invention provides a method for identifying a substructure of a chosen molecule using a microprocessor. The method comprises: a) executing on the microprocessor a graphical input module to receive a chemical diagram of the chosen molecule and annotations that identify (A) minimum cleavable units of the chosen molecule, (B) molecular weights of each minimal cleavable unit of the chosen molecule, and (C) types of bonds connecting minimum cleavable units of the chosen molecule, b) executing on the microprocessor a matrix creator to generate a minimum cleavable unit graph adjacency matrix of the chosen molecule, the minimum cleavable unit graph adjacency matrix having a plurality of records, each record corresponding to a pair of vertices and having a field that is assigned a first value where an edge exists between the pair or a second value where an edge does not exist between the pair, each vertex corresponding to a minimum cleavable unit of the chosen molecule, wherein an edge represents a bond connecting minimum cleavable units of the chosen molecule, c) executing on the microprocessor a line graph matrix generator module to generate a line graph adjacency matrix from the minimum cleavable unit graph adjacency matrix, the line graph adjacency matrix having a plurality of vertices, each vertex corresponding to a pair of edges of the minimum cleavable unit graph adjacency matrix and having a field that is assigned the first value where an endpoint exists between the pair of edges or a the second value where no endpoint exists between the pair of edges, the line graph adjacency matrix having a vertex for each edge of the minimum cleavable unit graph adjacency matrix based upon endpoints connected by the edge, wherein vertices represent bonds between the minimum cleavable units of the chosen molecule, d) executing on the microprocessor an edge to vertex matrix generator module to generate an edge to vertex matrix from the minimum cleavable unit adjacency matrix, the edge to vertex matrix having a plurality of elements, each element corresponding to an edge and a vertex of the minimum cleavable unit graph adjacency matrix and having a field that is assigned the first value where the edge and the vertex are connected to each other or the second value where the edge and the vertex are not connected to each other, the vertices representing minimum cleavable units of the chosen molecules and the edges representing bonds connecting the minimum cleavable units of the chosen molecule, e) executing on the microprocessor a graph traversing engine that traverses the line graph adjacency matrix and the edge to vertex matrix using a graphical search to produce and store induced connected subgraphs of the line graph adjacency matrix, and f) executing on the microprocessor a molecular weight calculator module that calculates and stores in a database a molecular weight for each induced connected subgraph generated by the graph traversing engine, wherein the molecular weight for each induced connected subgraph is calculated by retrieving and summing together the molecular weights of every vertex of the induced connected subgraph.

In yet another aspect, the invention provides an apparatus for creating and searching a database in a memory of a computer system using a microprocessor to identify chemical substructures of a chosen molecule. The apparatus comprises the following stored in the memory: a) an input module, b) a database generating module and c) a search engine.

The input module comprises program instructions that, when executed by the microprocessor, causes the microprocessor to receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween.

The database generating module comprises program instructions that, when executed by the microprocessor, causes the microprocessor to (i) based on the chosen molecule data, create and store in the memory a V2V adjacency matrix for the chosen molecule, the V2V adjacency matrix comprising a plurality of V2V vectors, wherein the plurality of V2V vectors is populated with a set of V2V values selected to identify, for each pair of vertices in the chosen molecule, whether said pair of vertices are connected to each other by a bond in the chosen molecule, (ii) generate and store in the memory an edge-to-vertex (E2V) adjacency matrix for the chosen molecule based on the V2V adjacency matrix, the E2V adjacency matrix comprising a plurality of E2V vectors, wherein the plurality of E2V vectors is populated with a set of E2V values selected to identify, for each edge-vertex pair in the V2V adjacency matrix, whether the edge and the vertex of said each edge-vertex pair are directly connected to each other in the chosen molecule, (iii) generate and store in the memory an edge-to-edge (E2E) adjacency matrix based on data in the E2V adjacency matrix, the E2E adjacency matrix comprising a plurality of E2E vectors, wherein the plurality of E2E vectors is populated with a set of E2E values selected to identify, for each pair of edges in the chosen molecule, whether said each pair of edges are directly connected to each other by a vertex in the chosen molecule; (iv) execute a graph traversing algorithm against the E2V values in the E2V adjacency matrix and the E2E values in the E2E adjacency matrix to determine every induced connected subgraph of the E2E graph, a vertex position for every vertex said every induced connected subgraph, and an edge position for every edge in said every induced connected subgraph, (v) for said every induced connected subgraph of the E2E graph, creating in the database an ICS record comprising a molecular weight field, a vertex data field and an edge data field, wherein the vertex data field is populated with vertex values configured to indicate the vertex position for said every vertex in the induced connected subgraph, and the edge data field is populated with edge values configured to indicate the edge position for said every edge in the induced connected subgraph, and (vi) use the connectivity profile, the set of molecular weights for the elements of the chosen molecule, and the ICS record for every induced connected subgraph to calculate and store in the molecular weight field of each ICS record a total molecular weight for the induced connected subgraph of that ICS record.

The search engine comprises program instructions that, when executed by the microprocessor, causes the microprocessor to (i) receive a specified molecular weight, (ii) search the database to find at least one ICS record in which the total molecular weight in the molecular weight field is equivalent to the specified molecular weight, and (iii) transmit the vertex values of the vertex data field and the edge values of the edge data field for said at least one ICS record to a display device.

In some embodiments of the invention, the apparatus further comprises a visualizer module, stored in the memory, comprising program instructions that, when executed by the microprocessor, will cause the microprocessor to retrieve and use the connectivity profile, the list of elements, the vertex values in the vertex data field and the edge values in the edge data field of said at least one ICS record to generate and display on the display device a graphical representation of the induced connected subgraph for said at least one ICS record.

In some embodiments of the invention, the apparatus further comprises an MCU library, stored in the memory, comprising a set of MCU properties for the defined MCU, the set of MCU properties comprising a) a list of constituents in the defined MCU, or b) a molecular weight for a constituent of the defined MCU, or c) a chemical structure for the defined MCU, or d) a common name for the defined MCU, or e) any combination of two or more of the above-referenced MCU properties.

In some embodiments of the invention, each of the induced connected subgraphs of the E2E graph has a connected set of edges and vertices, and a physical arrangement of said connected set of edges and vertices, that together uniquely corresponds to a connected set of elements and a physical arrangement of said connected set of elements for a metabolite of the chosen molecule, or a catabolite of the chose molecule, or a gas phase fragmentation of the chosen molecule, or a degradant of the chosen molecule, or a substructure of the chosen molecule.

In still another aspect, the invention provides an apparatus for creating a database in a memory of a computer system to facilitate identifying chemical substructures of a chosen molecule using a microprocessor, the apparatus comprising a) an input module stored in the memory and ii) a database generating module stored in the memory.

The input module comprises program instructions that, when executed by the microprocessor, causes the microprocessor to receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween.

The database generating module comprises program instructions that, when executed by the microprocessor, causes the microprocessor to (i) generate and store in the memory an edge-to-vertex (E2V) graph for the chosen molecule based on the connectivity profile, the E2V graph comprising a plurality of E2V vectors, wherein the plurality of E2E vectors is populated with a set of E2V values selected to identify, for each edge-vertex pair in the chosen molecule, whether the edge and the vertex of said each edge-vertex pair are directly connected to each other in the connectivity profile of the chosen molecule, (ii) generate and store in the memory an edge-to-edge (E2E) graph based on data in the E2V graph, the E2E graph comprising a plurality of E2E vectors, wherein the plurality of E2E vectors is populated with a set of E2E values selected to identify, for each pair of edges in the chosen molecule, whether said each pair of edges are directly connected to each other by a vertex in the connectivity profile of the chosen molecule, (iii) execute a graph traversing algorithm against both the E2V graph and the E2E graph to determine every induced connected subgraph of the E2E graph, a vertex position for every vertex said every induced connected subgraph, and an edge position for every edge in said every induced connected subgraph, (iv) for said every induced connected subgraph of the E2E graph, create in the database an ICS record comprising a molecular weight field, a vertex data field and an edge data field, wherein the vertex data field is populated with vertex values configured to indicate the vertex position for said every vertex in the induced connected subgraph, and the edge data field is populated with edge values configured to indicate the edge position for said every edge in the induced connected subgraph, and (v) use the connectivity profile, the set of molecular weights for the elements of the chosen molecule, and the ICS record for every induced connected subgraph to calculate and store in the molecular weight field of each ICS record a total molecular weight for the induced connected subgraph of that ICS record.

In some embodiments of the invention, the apparatus further comprises a visualizer module, stored in the memory, comprising program instructions that, when executed by the microprocessor, will cause the microprocessor to retrieve and use the connectivity profile, the list of elements, the vertex values in the vertex data field and the edge values in the edge data field of said at least one ICS record to generate and display on the display device a graphical representation of the induced connected subgraph for said at least one ICS record.

In another aspect, the invention provides an apparatus for searching a database to find and transmit to a display device information describing a set of component parts for a chemical substructure of a chosen molecule and a physical arrangement of said component parts using a microprocessor. The apparatus comprises a) an electronic interface to a database comprising a multiplicity of ICS records, each ICS record comprising a molecular weight field, a vertex data field and an edge data field, wherein the vertex data field is populated with vertex values configured to indicate a vertex position for every vertex in an induced connected subgraph for a line graph representing a connectivity profile of the chosen molecule, and the edge data field is populated with edge values configured to indicate an edge position for every edge in the induced connected subgraph, b) an input module configured to cause the microprocessor to receive a specified molecular weight, c) a search engine having program instructions that, when executed by the microprocessor, will cause the microprocessor to use the electronic interface to the database to find at least one ICS record in which the total molecular weight in the molecular weight field is equivalent to the specified molecular weight; and d) an output module, stored in the memory, configured to transmit the vertex values of the vertex data field and the edge values of the edge data field for said at least one ICS record to the display device.

In some embodiments of the apparatus, the search engine further comprises program instructions that, when executed by the microprocessor, causes the microprocessor to a) receive a specified tolerance for the molecular weight, b) use the specified tolerance to calculate and define a range of molecular weights for the search of the database, and c) search the database to find the at least one ICS record in which the total molecular weight in the molecular weight field falls within the defined range of molecular weights.

In some embodiments of the invention, the apparatus further comprises a) a connectivity profile for the chosen molecule, b) a list of elements for the chosen molecule, and c) a visualizer module, stored in the memory, comprising program instructions that, when executed by the microprocessor, will cause the microprocessor to use the connectivity profile, the list of elements, the vertex values in the vertex data field and the edge values in the edge data field of said at least one ICS record to generate and display on the display device a graphical representation of the induced connected subgraph for said at least one ICS record.

In some embodiments of the invention, the graphical representation comprises a) a chemical structure diagram, or b) an MCU graph diagram, or c) a vertex to vertex (V2V) graph diagram, or d) an edge to edge (E2E) graph diagram, or e) an edge to vertex (E2V) graph diagram, or f) a line graph diagram, or g) a combination of two or more of the recited diagrams.

In additional embodiments of the invention, the apparatus further comprises a database; and a database generating module stored in the memory comprising program instructions that, when executed by the microprocessor, causes the microprocessor to i) generate and store in memory an edge-to-vertex (E2V) graph for the chosen molecule based on the connectivity profile, the E2V graph comprising a plurality of E2V vectors, wherein the plurality of E2E vectors is populated with a set of E2V values selected to identify, for each edge-vertex pair in the chosen molecule, whether the edge and the vertex of said each edge-vertex pair are directly connected to each other in the connectivity profile of the chosen molecule, and (ii) generate and store in memory an edge-to-edge (E2E) graph based on data in the E2V graph, the E2E graph comprising a plurality of E2E vectors, wherein the plurality of E2E vectors is populated with a set of E2E values selected to identify, for each pair of edges in the chosen molecule, whether said each pair of edges are directly connected to each other by a vertex in the connectivity profile of the chosen molecule, (iii) execute a graph traversing algorithm against both the E2V graph and the E2E graph to determine every induced connected subgraph of the E2E graph, a vertex position for every vertex said every induced connected subgraph, and an edge position for every edge in said every induced connected subgraph, (iv) for said every induced connected subgraph of the E2E graph, create in the database an ICS record comprising a molecular weight field, a vertex data field and an edge data field, wherein the vertex data field is populated with vertex values configured to indicate the vertex position for said every vertex in the induced connected subgraph, and the edge data field is populated with edge values configured to indicate the edge position for said every edge in the induced connected subgraph, and (v) use the connectivity profile, the set of molecular weights for the elements of the chosen molecule, and the ICS record for every induced connected subgraph to calculate and store in the molecular weight field of each ICS record a total molecular weight for the induced connected subgraph of that ICS record.

BRIEF DESCRIPTION OF THE DRAWINGS

FIG. 9A illustrates a Minimum Cleavable Unit Graph of a chosen hypothetical molecule that may be generated by the process of FIG. 7; FIG. 9B illustrates an exemplary MCU graph data structure for the chosen hypothetical molecule generated in accordance with an embodiment of the invention; FIG. 9C illustrates an exemplary Line Graph that may be generated to represent the chosen hypothetical molecule; FIG. 9D illustrates an exemplary Line graph data structure, namely an adjacency matrix (E2E) of the Line Graph shown in FIG. 9C. FIG. 9E is a high-level diagram of two exemplary induced connected subgraphs that may be generated by traversing the line graph data structure for a hypothetical chosen molecule.

FIG. 10A shows an MCU graph of a iraglutide molecule.

FIGS. 12A and 12B show MCU graphs for Peptide A, generated in accordance with an embodiment of the invention.

FIG. 12C shows an MCU graph data structure (adjacency matrix) for Peptide A generated in accordance with an embodiment of the invention.

FIGS. 15A and 15B show exemplary ICS records stored in a database generated in accordance with an embodiment of the invention, including the molecular weight field, vertex array field, and edge array field.

FIG. 22A shows the chemical structure of insulin detemir, on which the process of FIG. 6 may operate.

FIG. 24 is a line graph corresponding to the MCU graph data structure for insulin detemir.

FIGS. 30A-30D show four exemplary database entries (ICS records) generated in accordance with an embodiment of the invention.

FIGS. 32A, 32B, 33A and 33B show proposed chemical structures of four metabolites of insulin detemir that were generated in accordance with the embodiment of the invention set forth in FIGS. 6 and 16.

DETAILED DESCRIPTION OF EXEMPLARY EMBODIMENTS

In general, embodiments of the present invention may be used by scientists, such as chemists and biochemists, to identify the substructures of a complex molecule, such as the metabolites of the molecule and to determine the associated chemical structures of the same. Embodiments of the present invention may be useful in drug development and design.

Figure 1:
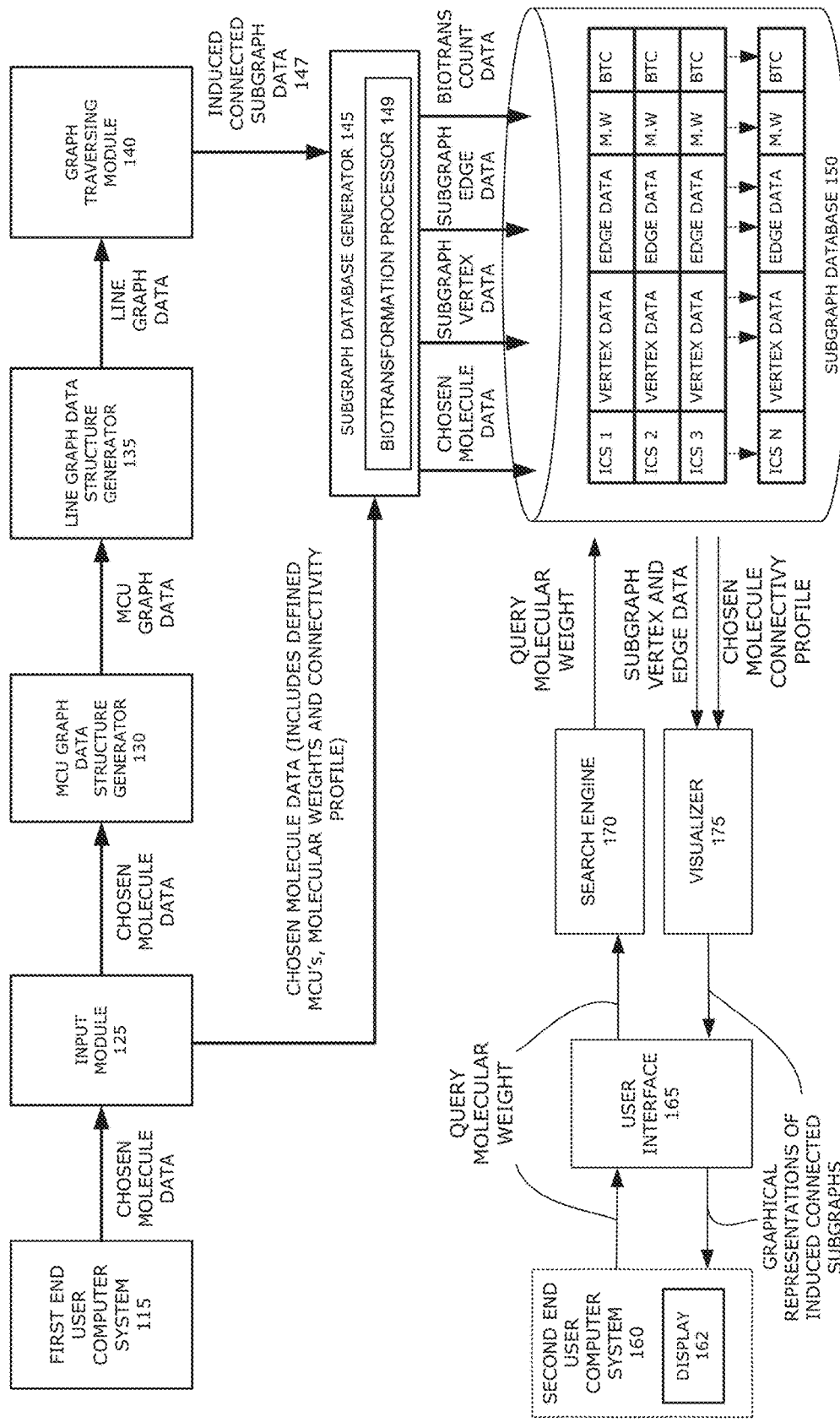
FIG. 1 shows a high-level flow diagram illustrating, by way of example, the flow of data in an embodiment of the present invention.

FIG. 1 shows a high-level flow diagram illustrating, by way of example, the flow of data in an embodiment of the present invention. As shown in FIG. 1, a first user uses a first end user computer system 115 and an input module 125 to supply chosen molecule data to the system, the chose molecule data including a set of defined MCUs for the chosen molecule, molecular weights for the MCUs and a connectivity profile for the chosen molecule. The connectivity profile indicates relative positions of minimum cleavable units and bonds, and any connections between the MCUs and bonds in the chosen molecule. An MCU graph data structure generator 130 creates and populates an MCU graph data structure with data representing an MCU graph for the chosen molecule. The MCU graph data structure generator 130 stores the MCU graph data in a memory device (not shown in FIG. 1) associated with the system. A line graph data structure generator 135 retrieves the MCU graph data from the MCU graph data structure and uses it to create and populate a line graph data structure.

A graph traversing module 140 then uses a suitable graph traversal algorithm to traverse the data in the line graph data structure to produce induced connected subgraph data 147, which represents all of the induced connected subgraphs that can be derived from the line graph represented by the line graph data in the line graph data structure. A subgraph database generator 145 uses the induced connected subgraph data 147 and the chosen molecule data (particularly the molecular weights) to build and populate a subgraph database 150. The subgraph database 150 includes a plurality of ICS records, each record comprising at least a vertex data field with vertex data for the induced connected subgraph, an edge data field with edge data for the induced connected subgraph, a molecular weight field populated with the molecular weight for the induced connected subgraph, and a biotransformation count field populated with values representing the number biotransformations (defined below) required to transform the chosen molecule into the substructure represented by the values stored in the vertex, edge and molecular weight fields in each ICS record. The subgraph database generator 145 calculates the molecular weight for each induced connected subgraph based on the molecular weights for the MCUs in the chosen molecule data supplied by the end user.

Figure 5:
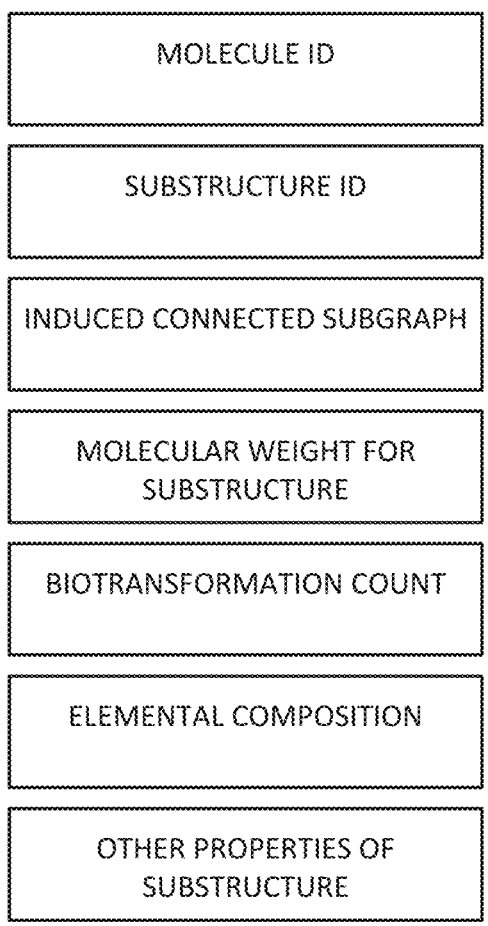
FIG. 5 shows an exemplary induced connected subgraph (ICS) record that may be stored in the database in accordance with embodiments of the present invention.

As shown in FIG. 1, the biotransformation counts may be calculated by a biotransformation processor 149 associated with the subgraph database generator 145, the biotransformation processor 149 being configured to carry out a biotransformation counting algorithm such as the algorithm depicted in FIG. 3 and described in more detail below. FIG. 5 shows an exemplary induced connected subgraph (ICS) record that may be stored in the subgraph database 150 in accordance with embodiments of the present invention.

After the subgraph database 150 is built (it may have millions of records), a second user can use a second end user computer system 160 and a user interface 165 to search the database 150 based on a given query molecular weight (or a given range of molecular weights). The query molecular weight (or range of weights) is passed to a search engine 170, which causes the system to retrieve from the subgraph database 150 vertex data and edge data for all of the records that have molecular weights that are equivalent to the query molecular weight or fall within the specified range of molecular weights. A visualizer 175 uses the vertex data and edge data to generate a graphical representation of the induced connected subgraph, which is transmitted via the user interface 165 to a display device 162 operated by the second user. In preferred embodiments, if there are two or more induced connected subgraphs that match the query mass (or range), the visualizer 175 and user interface 165 operate to rank the matching induced connected subgraphs according to the values in their respective biotransformation fields, and to display the matching induced connected subgraphs in rank order. It is noted that the first end user computer system and the second end user computer system may, in some embodiments, comprise the same computer system. In other words, the system may be configured so that the same computer system is used to initiate both the database generation and the database searching functions of the system.

Figure 2:
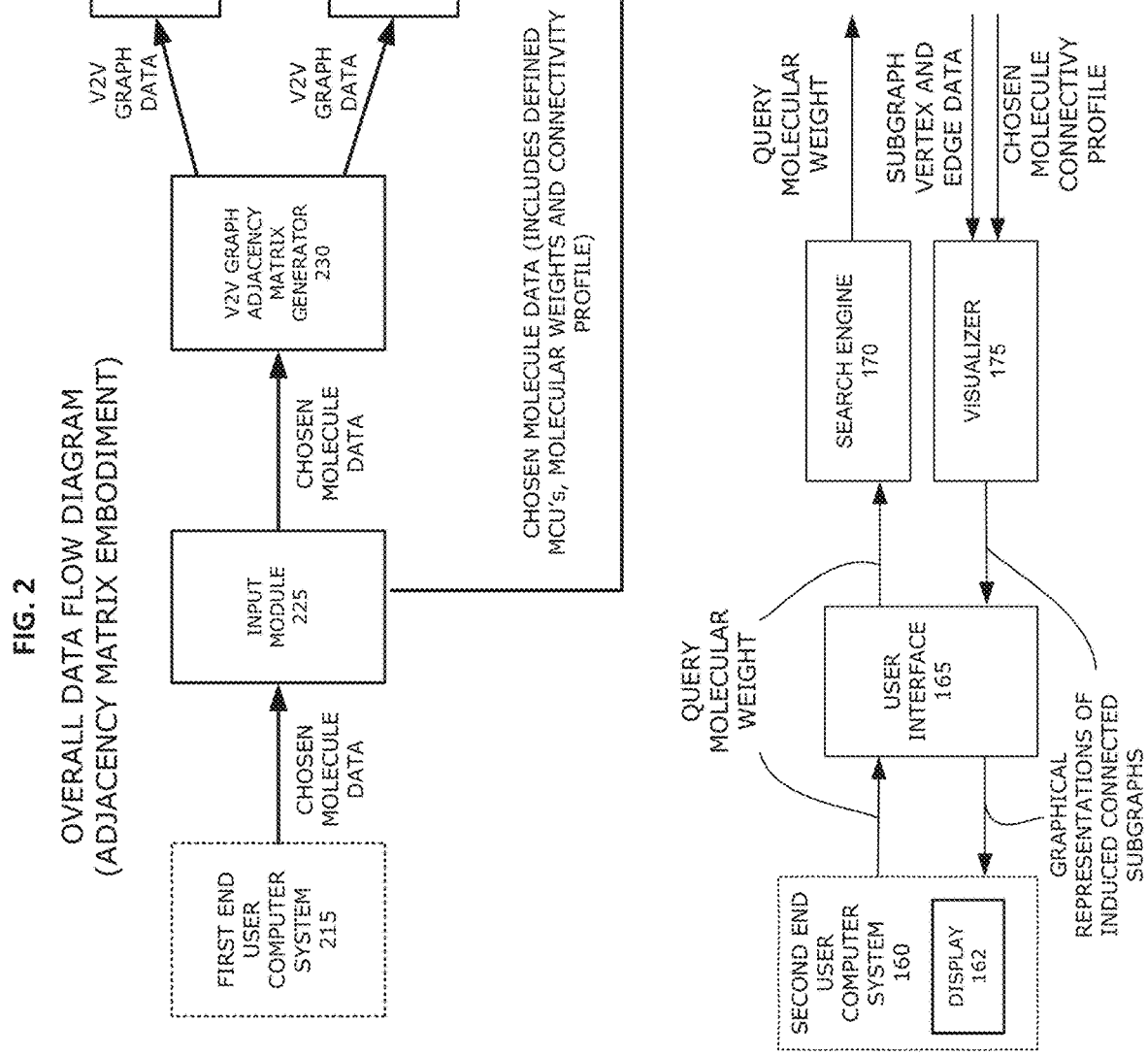
FIG. 2 shows a high-level overall flow diagram illustrating, by way of example, the flow of data in another embodiment of the present invention, wherein the data structures representing the various types of graphs are adjacency matrices.

FIG. 2 shows a high-level overall flow diagram illustrating, by way of example, the flow of data in another embodiment of the present invention, wherein the data structures representing the various types of graphs are adjacency matrices. As shown in FIG. 2, the overall data flow is substantially the same as the overall data flow in the system illustrated in FIG. 1, except that a vertex to vertex (V2V) adjacency matrix generator 230 uses the chosen molecule data to generate and store V2V graph data, an edge-to-edge (E2E) graph adjacency matrix generator 235 uses the V2V graph data to generate and store E2E graph data, and an edge-to-vertex (E2V) graph adjacency matrix generator 237 uses the V2V graph data to generate and store E2V graph data.

Figure 3:
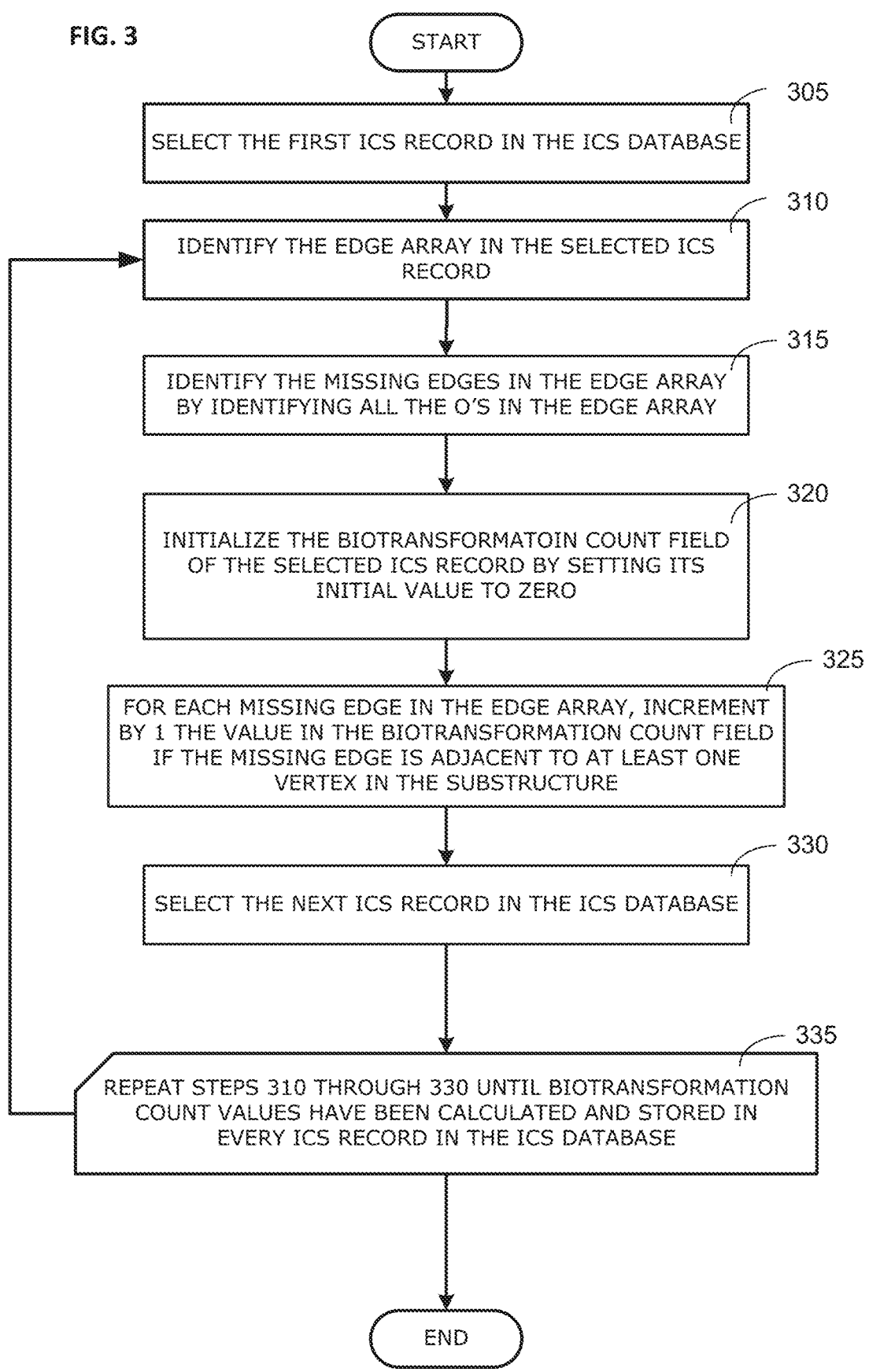
FIG. 3 shows a high-level flow diagram illustrating, by way of example, an algorithm for calculating and storing in the induced connected subgraph (ICS) database the biotransformation counts associated with each one of the induced connected subgraphs derived by embodiments of the invention.

FIG. 3 shows a high-level flow diagram illustrating, by way of example, an algorithm for calculating and storing in the ICS database the biotransformation counts associated with each one of the induced connected subgraphs represented by the vertex array data and edge array data created by the system. For the purposes of this disclosure, a "biotransformation" is defined as the breaking of a covalent bond between two MCUs.

Often, multiple metabolites will match a given query mass in a search, depending on a tolerance range specified in the search query, e.g., within ±5 ppm, within ±4 ppm, within ±2 ppm, or some other limited range around the given search mass. In such cases, it is often efficient and desirable to filter (or at least prioritize) the list of metabolites returned in the search so that the metabolites that are more likely to be generated from the chosen molecule are displayed at the top of the list of metabolites returned in the search results, i.e., they are displayed before displaying the metabolites that are less likely to be generated from the chosen molecule. Because metabolites are typically produced enzymatically, and because enzymes typically hydrolyze one bond at a time, it is reasonable to assume that the metabolites that can be generated by breaking the fewest number of bonds in the chosen molecule are also the metabolites that are most likely to be generated from that chosen molecule, regardless of whether the metabolites are generated in the body or in a laboratory. A similar sequential fragmentation process occurs during gas phase fragmentation. One bond breaks at a time, with the weakest bond breaking first, followed by the breaking of the next weakest bond, and so on.

Accordingly, embodiments of the present invention, and in particular, the subgraph database generator, may include a biotransformation processor (such as a set of computer program instructions) configured to count and store in the ICS database, for each induced connected subgraph (i.e., each metabolite) represented in the ICS database, the number of biotransformations (or broken covalent bonds) that are required to transform the chosen molecule into that particular metabolite. In addition, the search engine is suitably configured to use the stored biotransformation counts, along with the query mass, to retrieve and display the metabolites in the search results in ranked order, wherein the metabolites having the lower biotransformation count values are ranked higher than the metabolites having the highest biotransformation count values. In some embodiments, the system may also be configured to filter the search results so that those metabolites requiring more than a specified maximum number of biotransformations will be filtered out of the search results and not presented on the user's display device.

Say, for example, that the chosen molecule is the linear peptide A-N-T-G-F-A-N-G-G, and one of the metabolites matching the query mass is A-N-T-G-F, and another one of the metabolites matching the query mass is T-G-F-A-N. Evidently, it takes a single broken bond to obtain the A-N-T-G-F metabolite from the chosen molecule, while it takes two broken bonds to obtain the T-G-F-A-N metabolite. In this situation, the user interface for the search query module would rank the A-N-T-G-F metabolite higher than the T-G-F-A-N metabolite.

Embodiments of the present invention are configured to produce an ICS database comprising an ICS record representing every substructure that can be generated from the chosen molecule. Each ICS record comprises at least a vertex array, an edge array and a biotransformation count field. Accordingly, as shown in FIG. 3, one algorithm for counting and storing the number of biotransformations for each substructure represented in the ICS database would proceed as follows:

Step 305—select the first ICS record in the ICS database;
Step 310—identify the edge array in the selected ICS record;
Step 315—identify the missing edges by identifying all of the 0's in the edge array;
Step 320—initialize the biotransformation count field of the selected ICS record by setting its initial value to zero;
Step 325—for each missing edge in the edge array, increment by 1 the value in the biotransformation count field if the missing edge is adjacent to at least one vertex in the substructure;

Step 330—select the next ICS record in the ICS database; and

Step 335—Repeat steps 310 through 330 above until biotransformation count values have been calculated and stored in every ICS record in the ICS database.

In some cases, the structure of the chosen molecule comprises two monomers (monomer A and monomer B) separated by a cut vertex. For a substructure or metabolite of such a chosen molecule that straddles the cut vertex, the number of biotransformations is the sum of the number of biotransformations needed to transform the chosen molecule into monomer A and the number of biotransformations needed to transform the chosen molecule into monomer B.

The values stored in the biotransformation count fields in accordance with this algorithm may then be used by embodiments of the invention to rank and/or filter the search results so that the substructures that are the most likely to be generated are the only substructures listed or displayed to the end user, or so that the substructures that are the most likely to be generated are listed or displayed at the top of list (i.e., before the substructures that are less likely to be generated).

Figure 4:
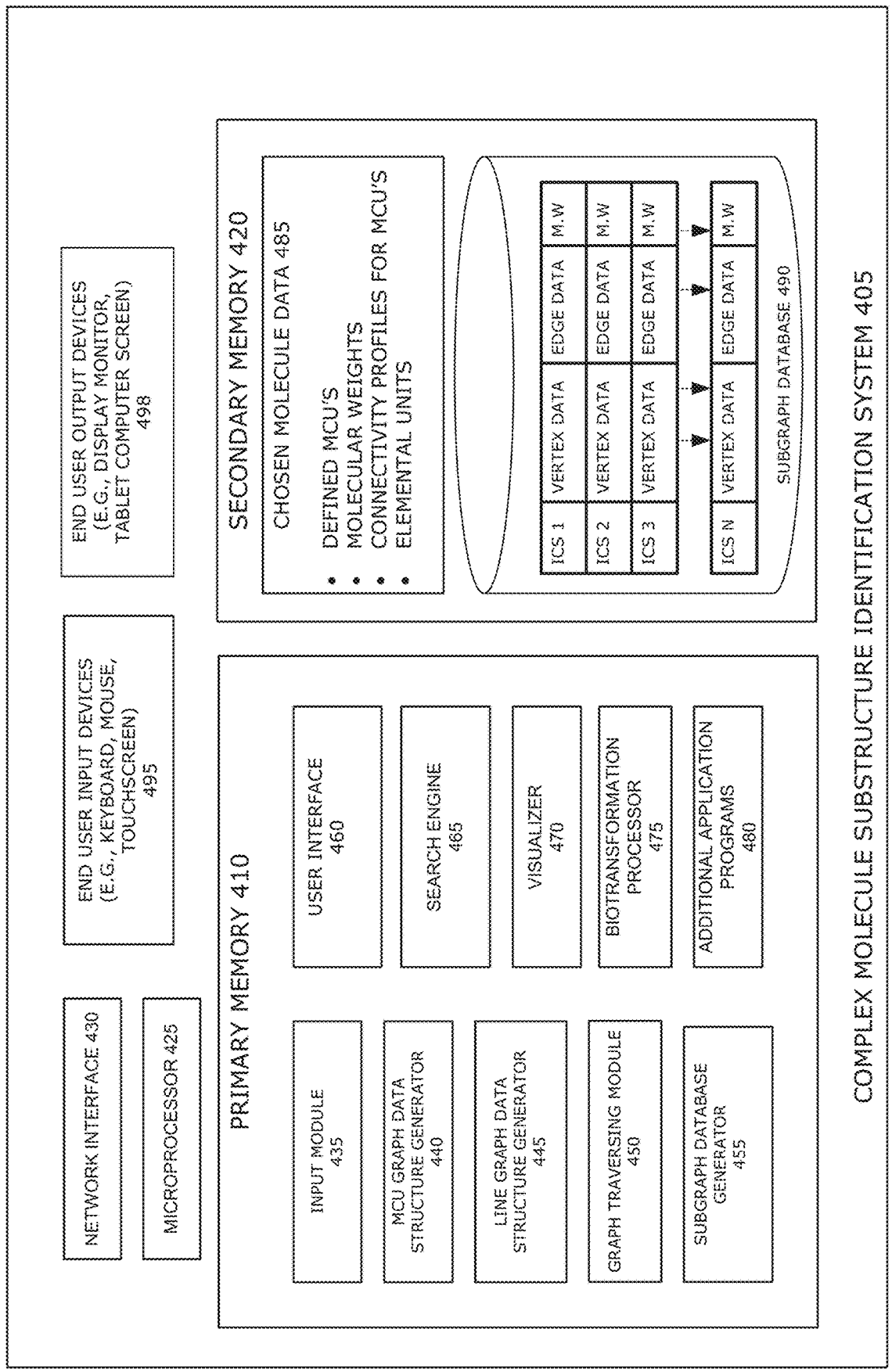
FIG. 4 shows a high-level block diagram illustrating an example of the architecture for a complex molecule substructure identification system configured to operate in accordance with an exemplary embodiment of the present invention.

FIG. 4 shows a high-level block diagram illustrating an example of the architecture for a complex molecule substructure identification system configured to operate in accordance with an exemplary embodiment of the present invention. The complex molecule substructure identification system 405 may be implemented on a general purpose or a specialized computer system, including, for example, a personal computer system, a notebook computer, a laptop, tablet or handheld computer system, an Internet-enabled smart phone or personal digital assistant computing device, or any combination of one or more thereof. Typically, the complex molecule substructure identification system 405 includes a central processing unit (CPU) or microprocessor 425, a primary memory 410 (also called random access memory (or RAM)), and a non-volatile secondary memory storage area 420 (e.g., a hard drive, a flash drive, or a CD-ROM drive). As shown in FIG. 4, the complex molecule substructure identification system 405 may also include a network interface 430, such as, for example, a wired Ethernet local area network adaptor, an 802.11 a/g/n WiFi adaptor, a universal serial bus (USB) adaptor, and/or a Bluetooth wireless data communications adaptor, to provide data communication with other computer systems, peripherals such as printers, and/or data communications networks. Program code, such as the code comprising an application program 412, and program data, such as chosen molecule data 485, can be loaded into the primary memory 410 (i.e., loaded into RAM) from the non-volatile secondary storage area 420 and provided to the microprocessor 425 for execution. Operating under the control of the application program 412, the microprocessor 425 can generate and store results in the secondary memory storage area 420 for subsequent access, display, output and/or transmission to other computer systems, other computer programs and/or other data communication networks.

The results of the substructure identification processes carried out by the microprocessor 425 under the control of the software modules of the application program 412 are stored in the secondary memory storage area 420, so that it can be viewed, navigated and modified, as required, by a human user interacting with the complex molecule substructure identification system 405 via one or more end user input devices 495 (e.g., a keyboard, mouse, stylus, touchscreen, etc.) and one or more end user output devices 498 (e.g., a display device, a printer, a tablet display screen, or smartphone display screen, etc.) operating under the control of a user interface module 460 in the application program 412. The secondary memory storage area 420, and the data it contains, may be integrated into the same physical machine as the microprocessor 425, the primary memory 410, the application program 412 and the software modules 435, 440, 445, 450, 455, 460, 465, 470, 475 and 480, as shown in FIG. 4. However, some or all of data and/or databases shown in the secondary memory storage area 420 may also reside on separate computer systems in a distributed arrangement without departing from the scope of the claimed invention.

The network interface 430 may be employed to establish a connection to remote servers and machines (e.g., mass spectrometer devices) containing or generating additional input data (not shown in FIG. 4) to be processed and a multiplicity of electronic files and documents deemed useful or necessary for carrying out the processes. The network interface 430 may also provide connectivity to remote terminals and remote computer systems (not shown) operated by other human users who wish to access and use the complex molecule substructure identification system 405 of the present invention.

The primary memory 410 may comprise without limitation one or more local or remote, fixed or removable, permanent or temporary, magnetic or optical, random access memory (RAM) areas, cache memory areas, or disk drives, contains a plurality of program modules for controlling the functions of microprocessor 425 to perform the methods of identifying substructures of complex molecules as described herein. Each one of these modules may comprise a computer software program, procedure, or process written as source code in a conventional programming language, and can be presented for execution by the microprocessor 425. The various implementations of the source code and object and byte codes can be stored on a computer-readable storage medium (such as a DVD, CDROM, floppy disk or memory card) or embodied on a transmission medium or carrier wave.

The application program 412 comprises a collection of computer software program modules 435, 440, 445, 450, 455, 460, 465, 470, 475 and 480, discussed below, each containing program instructions that cause the microprocessor 425 to perform a variety of specific tasks, as necessary, to receive various types of input data (such as chosen molecule data 485), and to execute the below-described algorithms to generate, store, transmit and display the MCU graphs, line graphs, induced connected subgraphs, substructure visualizations, biotransformation data, edge data and vertex data associated with the identification processes described herein. These software modules are flexible and may be configured to receive, process and output a large variety of different types of inputs and outputs, including without limitation, chemical structure drawing files, images and other electronic documents, graphs, layouts and schemas. The purpose and function of each one of the computer software modules 435, 440, 445, 450, 455, 460, 465, 470, 475 and 480 in the application program 412 will now be described in more detail below.

The application program 412 includes an input module 435, an MCU graph data structure generator module 440, a line graph data structure generator module 445, a graph traversing module 450, a subgraph database generator module 455, a user interface module 460, a search engine module 465, a visualizer module 470, a biotransformation processor module 475 and one or more additional data processing modules 480. The input module 435 comprises program instructions that, when executed by the microprocessor 425, causes the microprocessor 425 to receive and store in the secondary memory storage area 420 chosen molecule data 485 representing (A) a set of defined minimum cleavable units for the chosen molecule, (B) a set of bonds connecting the set of defined minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween. The input module 435 may also include program instructions that, when executed by the microprocessor 425, causes the microprocessor 425 to receive, scan, parse and/or store the data represented in a chemical diagram of the chosen molecule, the diagram including annotations that identify (A) minimum cleavable units of the chosen molecule, (B) molecular weights of each minimal cleavable unit of the chosen molecule, and (C) types of bonds connecting minimum cleavable units of the chosen molecule.

The MCU graph data structure generator 440 creates and populates an MCU graph data structure (an example of which is shown in FIG. 9D) with data representing an MCU graph for the chosen molecule. The MCU graph data structure generator 440 will typically store the MCU graph data in the secondary memory storage area 420 or some other memory storage area (not shown in FIG. 4) that is connected to or associated with the complex molecule substructure identification system 405. The line graph data structure generator 445 retrieves the MCU graph data from the MCU graph data structure and uses it to create and populate a line graph data structure, which is also stored in the secondary memory storage area 420, or some other memory storage area (not shown in FIG. 4) that is connected to or associated with the complex molecule substructure identification system 405.

The graph traversing module 450 then uses a suitable graph traversal algorithm to traverse the data in the line graph data structure to produce induced connected subgraph data 147, which represents all of the induced connected subgraphs that can be derived from the line graph represented by the line graph data in the line graph data structure. The subgraph database generator 455 uses the induced connected subgraph data 147 and the chosen molecule data 485 (particularly the molecular weights) to build and populate the subgraph database 490 stored in the secondary memory storage area 420. As shown in FIG. 4, the subgraph database 490 includes a plurality of ICS records, each record comprising at least a vertex data field with vertex data for the induced connected subgraph, an edge data field with edge data for the induced connected subgraph, a molecular weight field populated with the molecular weight for the induced connected subgraph, and a biotransformation count field populated with values representing the number biotransformations (defined above) required to transform the chosen molecule into the substructure represented by the values stored in the vertex, edge and molecular weight fields in each ICS record. The subgraph database generator 455 calculates the molecular weight for each induced connected subgraph based on the molecular weights for the MCUs in the chosen molecule data 485 supplied by the end user. The biotransformation processor 475 determines the biotransformations for each induced connected subgraph in accordance with the algorithm illustrated in FIG. 3 and described in detail above.

After the subgraph database 490 is built by a first user, a second user (or the first user) may operate one or more of the end user input devices 495 to activate the user interface 460 to search the subgraph database 490 based on a given query molecular weight (or a given range of molecular weights). The query molecular weight (or range of weights) is passed to the search engine 465, which causes the system to retrieve from the subgraph database 490 vertex data and edge data for all of the records that have molecular weights that are equivalent to the query molecular weight or fall within the specified range of molecular weights. Accordingly, the user interface module 460 and the search engine module 465 together comprise program instructions that, when executed by the microprocessor 425, will cause the microprocessor 425 to (i) receive the query molecular weight from the end user; (ii) search the subgraph database 490 based on the query molecular weight to identify an ICS record having a total molecular weight in the molecular weight field that matches the query molecular weight, and (iii) transmit the vertex values in the vertex data field and the edge values in the edge data field for the identified ICS record to the user interface 460 for presentation on the end user output device 498 (e.g., a display monitor) operated by the end user.

The visualizer module 470 includes program instructions that, when executed by the microprocessor 425, will cause the microprocessor 425 to use the vertex data and edge data for the identified ICS record in the subgraph database 490 to generate a graphical representation of the identified induced connected subgraph, which is transmitted via the user interface 460 to the end user output device 498 operated by the second user. In preferred embodiments, if there are two or more induced connected subgraphs that match the query mass (or range), program instructions in the visualizer module 470 and the user interface 460 operate to rank the matching induced connected subgraphs according to the values in their respective biotransformation fields, and to display the matching induced connected subgraphs in rank order on the end user output devices 498.

The additional data processing modules 480 may include, for example, a database management program (not shown) that creates, organizes and facilitates storing and retrieving ICS records to and from the subgraph database 490. Any type of database management program can be utilized, including a flat file system, hierarchical database, relational database, or distributed database, such as those provided by Oracle Corporation, of Redwood Shores, Calif.

In some embodiments, the complex molecule substructure identification system 405 is capable of acting as a server configured for communicating with client computing devices using a standard web browser, such as Internet Explorer, over a data communications network (not shown), which may comprise the Internet and the World Wide Web. In such embodiments, the complex molecule substructure identification system 405 may be implemented using any one of a number of available web server applications or programs, including, for example, Internet Information Services (IIS), available from Microsoft Corporation, of Redmond, Wash.

FIG. 5 shows an exemplary induced connected subgraph (ICS) record that may be stored in the database in accordance with embodiments of the present invention. As shown in FIG. 5, each ICS record in the subgraph database 490 of the secondary memory storage area 420 may comprise a plurality of different data fields associated with each induced connected subgraph of the chosen molecule, including without limitation, a molecule identifier field 505 for storing a specified identifier for each induced connected subgraph, a substructure identifier field 510 to store a specified identifier for each induced connected subgraph, an induced connected subgraph field 515 (typically a set of arrays) for storing vertex data and edge data for each induced connected subgraph, a molecular weight field 520 for storing the total molecular weight of the induced connected subgraph, a biotransformation count field 525 for storing the biotransformation count of each induced connected subgraph, an elemental composition field 530 for storing elemental composition data, and one or more other fields 535 for storing other properties associated with each one of the induced connected subgraphs.

Figure 6:
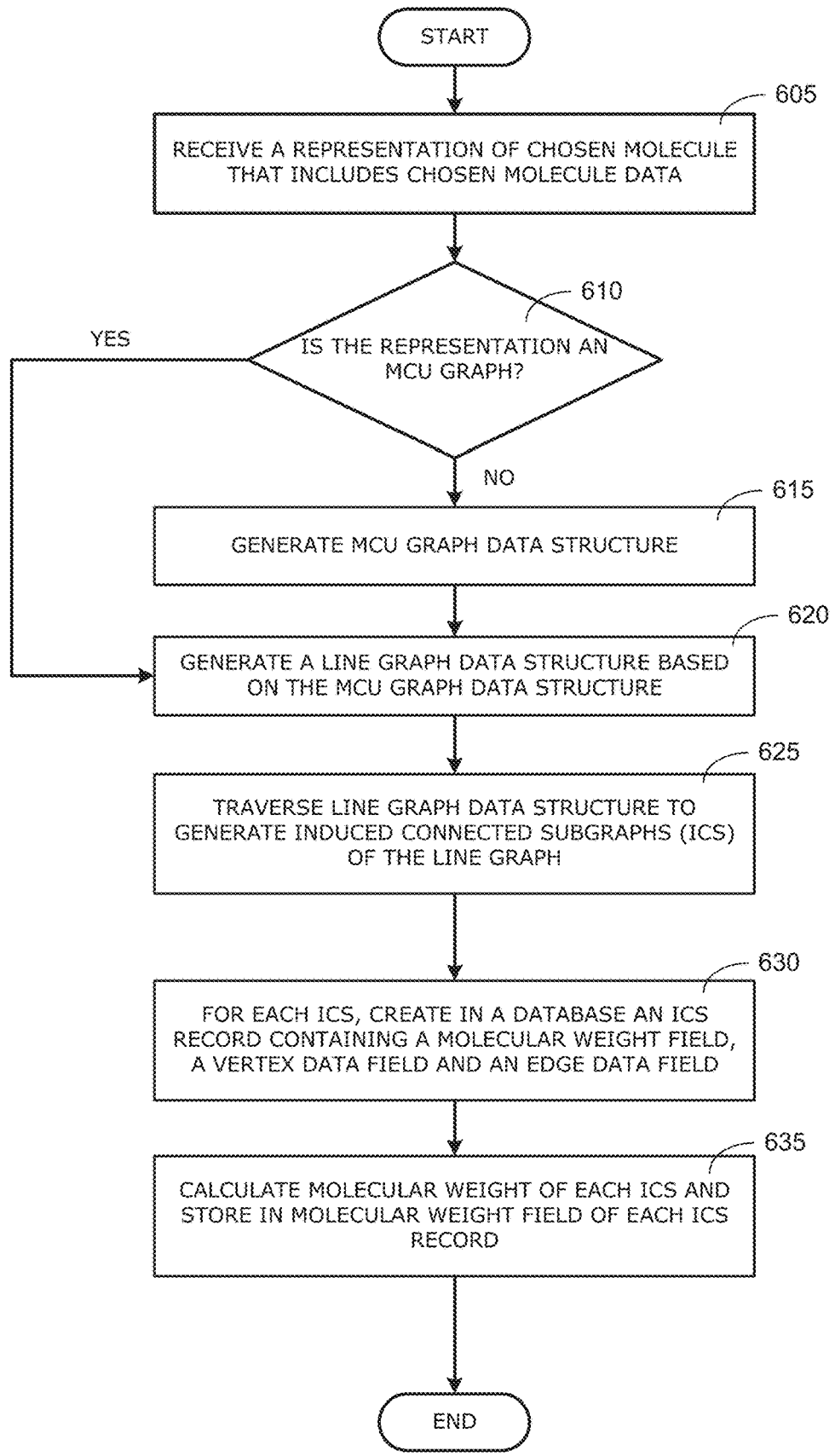
FIG. 6 is a flow diagram illustrating, in accordance with one embodiment of the present invention, the steps performed by the microprocessor to determine the chemical structure of metabolites for a chosen molecule in accordance with an embodiment of the present invention.

FIG. 6 is representative of steps or functions of processes or computer programs that may be stored in the primary memory 440 and executed by the microprocessor 425 to perform the function of identifying metabolites of a chosen molecule in accordance with an embodiment of the present invention.

For the purposes of this disclosure and convenience, the process illustrated in FIG. 6 may be viewed as the first phase of operation of the system of the present invention, which utilizes data structures of graphical representations of a chosen molecule in order to identify metabolites of a chosen molecule. Generally, FIG. 6 illustrates a process in which data structures are generated for MCU graphs and line graphs of the chosen molecule. The line graph data structures are traversed using a graph traversal algorithm to generate data structures of induced connected subgraphs, which represent substructures of the chosen molecule.

As the steps of the processes shown in FIG. 6 are described in this disclosure, reference will be made to FIGS. 7-15, wherein the results of the steps are shown with respect to exemplary chosen molecules.

Turning now to FIG. 6, a Substructure ID process 600 of the invention includes a number of steps, the result of which provides the exhaustive set of substructures of a chosen molecule. The structure of a hypothetical chosen molecule is shown in FIG. 9A. At step 605, the system receives a representation of a chosen molecule that includes chosen molecule data. The chosen molecule data includes the minimum cleavable units in the chosen molecule, the bonds connecting minimum cleavable units in the chosen molecule, the molecular weights for each minimum cleavable unit, and the connectivity profile for the chosen molecule. The connectivity profile indicates relative positions of minimum cleavable units and bonds and connections therebetween. The representation of the chosen molecule may be in the form of an MCU graph. FIG. 9A shows an exemplary MCU graph for a hypothetical molecule that may be received in accordance with the present invention. Each vertex 1, 2, 3, 4 and 5 of the MCU graph of FIG. 9A represents a minimum cleavable unit of the hypothetical molecule. Each edge, represented by the black lines connecting the vertices of the MCU graph in FIG. 9A, represents a bond that connects the minimum cleavable units of the chosen molecule.

Figure 7:
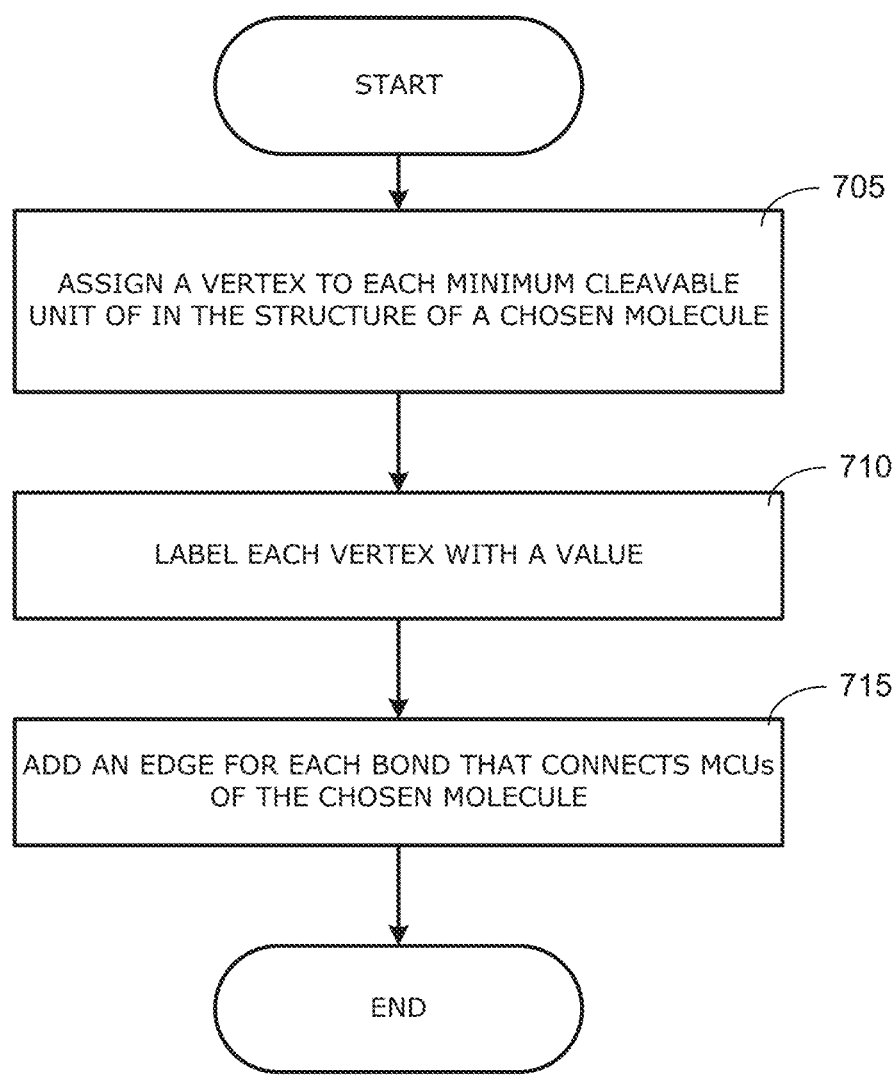
FIG. 7 is a flow diagram illustrating an algorithm for generating an MCU graph in accordance with an embodiment of the present invention.

In an alternative embodiment of the invention, in the first step of the process, the received representation of the chosen molecule is not an MCU graph, but rather a chemical diagram file that contains a structure, formula, drawing or other suitable representation of the chosen molecule. In this instance, the system, at step 615, generates an MCU graph and a corresponding MCU graph data structure for the chosen molecule, based upon the chemical structure of the molecule and the user-defined MCU, or based upon the chosen molecule data. The MCU graph may be generated from a chemical diagram file, such as a ChemDraw file, a chemical table file, or a HELM representation (Hierarchical Editing Language for Complex Macromolecules) of the molecule. The chemical diagram file may also be generated using the simplified molecular-input line-entry system (SMILES), As shown in FIG. 7, an MCU graph of the hypothetical chosen molecule may be generated as follows: At step 705, assign a vertex to each minimum cleavable unit of the chosen molecule. At Step 710, assign an identifier or value to each vertex. The identifier or value may be a numerical value, for example. As shown in FIG. 9A, the hypothetical chosen molecule has 5 vertices. The vertices are assigned numerical values 1, 2, 3, 4 and 5. At step 715, add an edge for each bond that connects the MCUs of the chosen molecule. The edges of the MCU graph for the chosen hypothetical molecule are denoted by the black lines connecting the vertices.

The MCU graph data structure that is generated by the system is preferably an adjacency matrix or an adjacency list. An exemplary MCU graph adjacency matrix for the chosen hypothetical molecule represented in FIG. 9A is shown in FIG. 9B. The adjacency matrix of the MCU graph is a Vertex to Vertex matrix (V2V). The Vertex to Vertex matrix comprises a data structure that, in an exemplary embodiment of the invention, is configured as an n by n matrix for a chosen molecule of n elemental components or n minimum cleavable units. Each slot in the matrix contains a numerical value of 1 (one) if two vertices are connected to one another or are adjacent, and a 0 if there is no adjacency between the two. Both the rows and the columns of the V2V matrix for the chosen hypothetical molecule are labelled 1 through 5 to represent the 5 vertices present in the corresponding MCU graph. By way of example, as shown in FIG. 9B, vertices 1 and 2 are adjacent, as denoted by the "1" in the row 1, column 2 of the matrix. On the other hand, vertices 1 and 5 are not adjacent, as denoted by the "0" set forth in row 1, column 5 of the matrix.

Returning to FIG. 6, at step 620, the system, in order to represent the line graph of the chosen molecule, generates a line graph data structure (also known as a "bond graph data structure" or "edge graph data structure") from the MCU graph data structure. For case of understanding, a line graph corresponding to the hypothetical molecule MCU graph adjacency matrix is depicted in FIG. 9C. Generally, the line graph encoding process is such that (i) each vertex of the line graph represents a covalent bond between the between the MCUs of the chosen molecule, and (ii) two vertices of the line graph are connected by an edge if and only if the corresponding covalent bonds are incident to the same MCU in the MCU graph.

Figure 8:
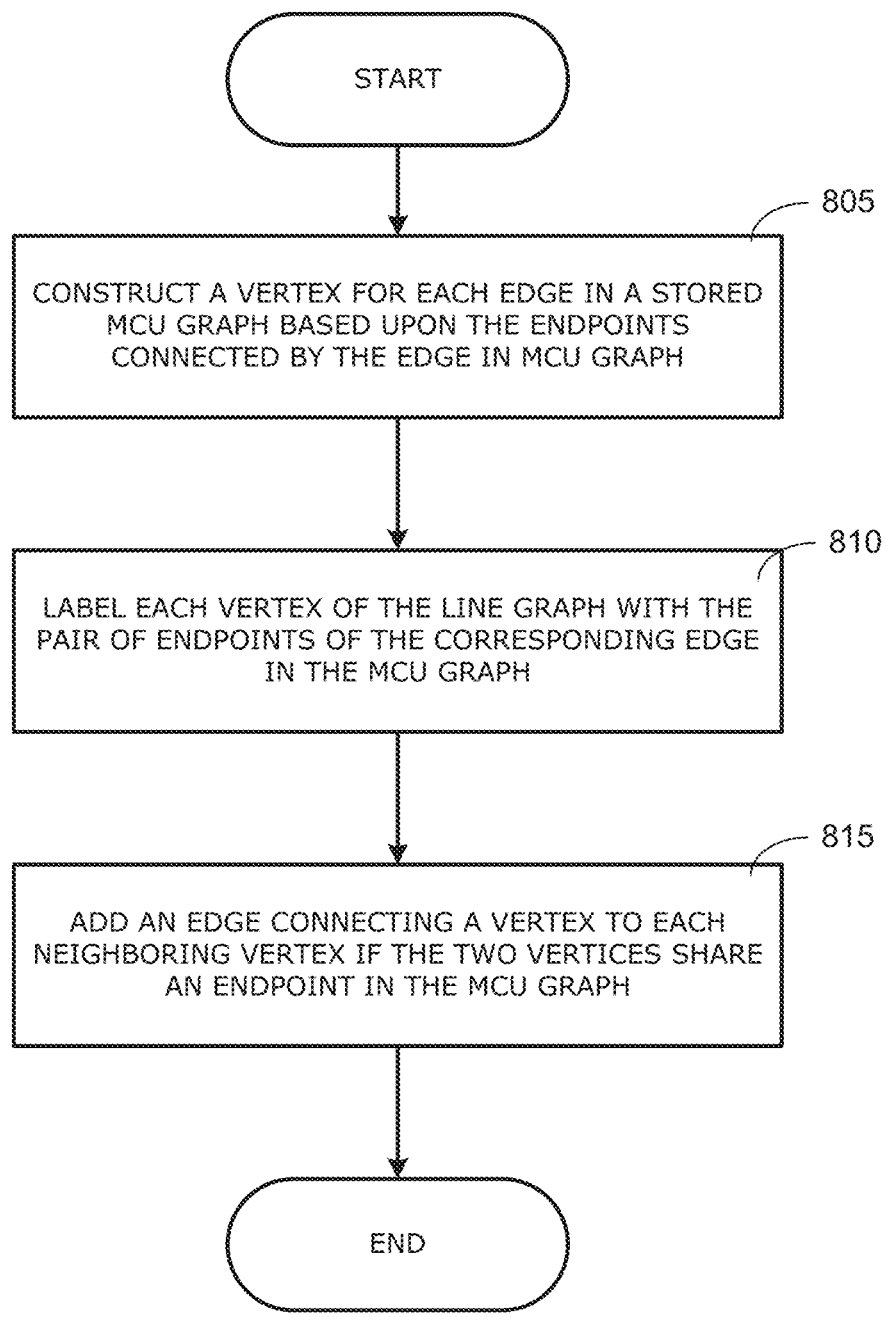
FIG. 8 is a flow diagram illustrating an algorithm for generating a line graph for an MCU graph in accordance with one embodiment of the present invention.

As illustrated by the flow diagram of FIG. 8, an algorithm for generating a line graph proceeds as follows: At step 805, vertices of the line graph are constructed from edges in the MCU Graph of the hypothetical chosen molecule, based upon the endpoints connected by each edge. Each vertex of the line graph is assigned a unique index, for example a numerical value, based upon the values assigned to the vertices of the corresponding MCU graph. The vertices of line graph correspond to the edges of the MCU. For the line graph of the chosen hypothetical molecule, vertex A of FIG. 9C corresponds to the edge connecting vertices 1 and 2 of the MCU graph of FIG. 9A; vertex B corresponds to the edge connecting vertices 1 and 3 of the MCU graph of FIG. 9A; vertex C of FIG. 9C corresponds to the edge connecting vertices 1 and 4 of the MCU graph of FIG. 9A; Vertex D of FIG. 9C corresponds to the edge connecting vertices 2 and 5 of the MCU graph of FIG. 9A. Vertex E of FIG. 9C corresponds to the edge connecting vertices 4 and 3 of the MCU graph of FIG. 9A; and vertex F of FIG. 9C corresponds to the edge connecting vertices 4 and 5 of the MCU graph of FIG. 9A.

The line graph data structure generated by the system of the invention is preferably a line graph adjacency matrix or adjacency list. In one embodiment of the invention, the line graph data structure is generated automatically by computer code, such as by a line graph data structure generating program like line graph data structure generator 445 (shown in FIG. 4), described above, or an edge to vertex (E2V) matrix generating program.

Typically, there are two types of adjacency matrices for the line graph, namely, an Edge to Edge matrix and an Edge to Vertex matrix. For each matrix, a notation of zeros and ones (0.1) may be used to describe a connection between components of the chosen molecule (designated "1") or the lack thereof (designated "0"). The (0,1) notation is but one example of a notation that may be used for a matrix. It will be understood that many other notations could be selected and used to express where connections exist or do not exist. Any notation that permits distinguishing between the presence and the absence of a connection between components of the chosen molecule may be suitably employed.

The Edge to Edge matrix comprises a data structure that, in an exemplary embodiment of the present invention, is configured as an n by n matrix for a chosen molecule of n elemental components or n minimum cleavable units. Each slot in the matrix contains a numerical value of 1 (one) if edge E1 and edge E2 are adjacent, and a 0 (zero) if there is no adjacency between the two.

The Edge to Vertex matrix comprises a data structure that, in an exemplary embodiment of the present invention, is configured an n by n matrix for a chosen molecule of n elemental components or minimum cleavable units. Each slot in the matrix contains a numerical value of 1 (one) if an edge and a given vertex are adjacent, and a 0 (zero) if there is no adjacency between the two.

An exemplary line graph adjacency matrix (E2E) corresponding to the MCU graph and MCU graph data structure for the chosen hypothetical molecule represented in FIG. 9A is set forth in FIG. 9D. An exemplary E2V matrix in accordance with the invention, for chosen molecule Peptide A is set forth in FIG. 14. The E2V matrix is a 13×12 matrix, with rows numbered 1 through 13 representing edges in the Peptide A MCU graph of FIG. 12A and the MCU graph data structure of FIG. 12C, and columns numbered 1 through 12 representing vertices of the Peptide A MCU graph of FIG. 12 A. and the data structure of FIG. 12C.

At step 625, the system uses a graph traversing program containing program instructions that, when executed by a microprocessor, causes the microprocessor to perform the steps of a graph traversal algorithm to traverse the E2E and E2V matrices of the line graph to produce and store induced connected subgraphs of the line graph. FIG. 9E shows a high level representation of two induced connected subgraphs of the chosen hypothetical molecule represented by the MCU graph of FIG. 9A.

In one embodiment of the invention, the graphical search is a depth-first search. The process proceeds as follows: First, individual vertices of the line graph data structure are added as connected components. Next, for any connected component. (i) its vertex index is defined as the minimum index of its constituent vertices; (ii) its neighboring vertices are identified; (iii) a new connected component, defined as the union of the current connected component and each one of its neighboring vertices that has an index that is above the index of the current connected component, is added to the list of connected components; and (iv) the search (traversing the line graph adjacency matrices) proceeds inductively until all connected components have been enumerated. The lack of infinite loops is guaranteed by the particular direction of the search in the direction of non-decreasing vertex indices.

As the connected components (induced connected subgraphs) are enumerated, the system, at step 630 creates and stores an induced connected subgraph record (ICS record) in a database in secondary memory, such as, for example, subgraph database 490 shown in FIG. 4 and described above. The ICS record contains a molecular weight field, a vertex data field and an edge data field. FIGS. 15A and 15B show examples of the molecular weight data, vertex data and edge data that might stored in each ICS record be for chosen molecule Peptide A, in accordance with some embodiments of the invention.

At step 635 of FIG. 6, the system calculates and stores the total molecular weight corresponding to each induced connected subgraph and stores the molecular weight in the molecular weight field of the ICS record in the database. At the completion of the steps 630 and 635, all induced connected subgraphs have been enumerated and stored, and the corresponding molecular masses have been calculated and are stored, preferably in one or more databases. This completes the first phase of the metabolite identification process of the invention, which may be referred to as the substructure database building phase.

Importantly, the present inventors recognized that every induced connected subgraph of an MCU graph, such as the MCU graph shown in FIG. 9A, is a substructure of the chosen molecule represented by the MCU graph. Indeed, there are multiple substructures that correspond to each induced connected subgraph of an MCU graph, such as the MCU graph shown in FIG. 9A. The multiple substructures are not accounted for by writing out the induced connected subgraphs of the MCU graph. Hence, the pool of induced connected subgraphs of the MCU graph underestimates the pool of substructures of the molecule represented by an MCU graph, such as the MCU graph of FIG. 9A.

However, the present inventors have also recognized that the list of induced connected subgraphs of the line graph represented by the data structure of a line graph of a chosen molecule completely and uniquely represents the entire pool of substructures for the chosen molecule. This property is both novel and actionable because it leads to an algorithm that facilitates identification of the entire pool of metabolites of the chosen molecule and thereby improves the operation of a conventional computer system employed to identify all of the substructures of a complex molecule.

Figure 10B:
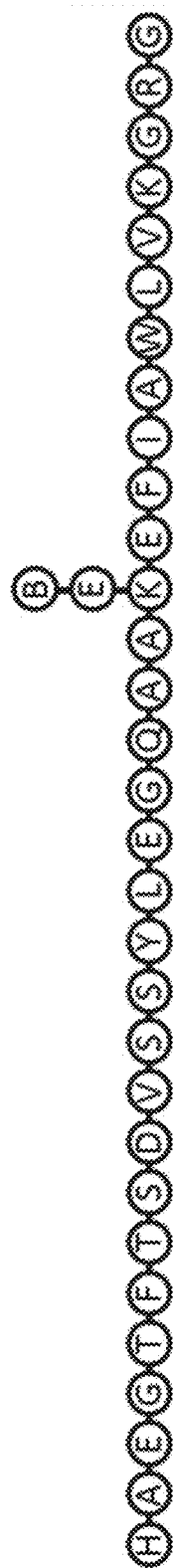
FIG. 10B is the corresponding line graph of the MCU graph of liraglutide, a derivative of human incretin glucagon-like peptide-1 (GLP-1) receptor agonist.

FIG. 10A shows the chemical structure of chosen molecule Liraglutide. FIG. 10B shows the corresponding MCU graph of Liraglutide. As shown in FIG. 10B, the user-defined MCU in this example is an amino acid residue. Because, in this example, there is no interest in any further metabolism beyond a single amino acid, each vertex of the MCU graph is an amino acid residue, with the exception of vertex B. Vertex B represents a fatty acid chain. In this example, no further metabolism was allowed to take place. Hence, vertex B is also an MCU.

The building blocks of the representation set forth in FIG. 10A are atoms, whereas the building blocks of the MCU graph in FIG. 10B are MCUs. One advantage of the atom-based representation of FIG. 10A is that it reveals the chemical details of the structure. However, a disadvantage is that the complexity of the atom-based representation is that it is often too complex for use in computing substructure databases and theoretical metabolite databases. The MCU representation overcomes this problem by allowing the user to ignore irrelevant details of the chemical structure.

Figure 11:
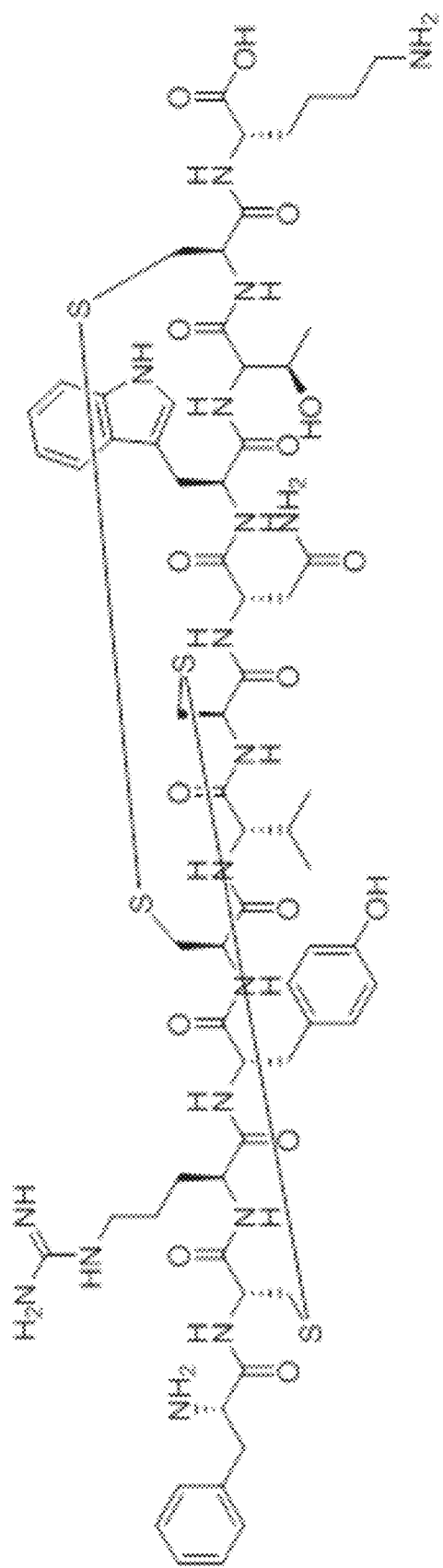
FIG. 11 is the chemical structure of an exemplary chosen molecule Peptide A having disulfide cross-linking bonds upon which the systems, apparatuses and methods of the invention may operate.

FIG. 11 shows the chemical structure of Peptide A, a 12 amino acid peptide containing 2 disulfide bonds.

FIGS. 12A and 12B show MCU graphs of Peptide A generated in accordance with an embodiment of the invention. In this instance an MCU of Peptide A is selected as an amino acid. Thus no cleavage is permitted beyond the amino acid level. As shown in FIG. 12A, there are 12 amino acids in the molecule and thus 12 vertices in the MCU graph, represented by the encircled letters. The MCU graph contains 13 edges, which are represented in FIG. 12A by the solid black lines connecting all the vertices to other vertices.

FIG. 12B is another MCU graph of Peptide A, with the vertices represented by encircled numbers instead of encircled letters.

The MCU graph data structure for Peptide A is set forth in FIG. 12C. The data structure comprises a 12×12 adjacency matrix that contains a row for each of the 12 vertices and 12 columns for each row. The presence or absence of a bond between each vertex is indicated using the 1,0 notation, where 1 denotes the presence of a bond or connection and 0 denotes the lack of a bond or connection. For example, vertex 1 is connected to vertex 2, hence the 1 in column 2, but is not connected to any other vertex, hence a zero is listed in each of the remaining 11 columns. As an additional example. Vertex 2 is connected to vertices 1, 3 and 7, hence the 1's in each of the respective columns for the row corresponding to Vertex 2.

Figures 13A, 13B:
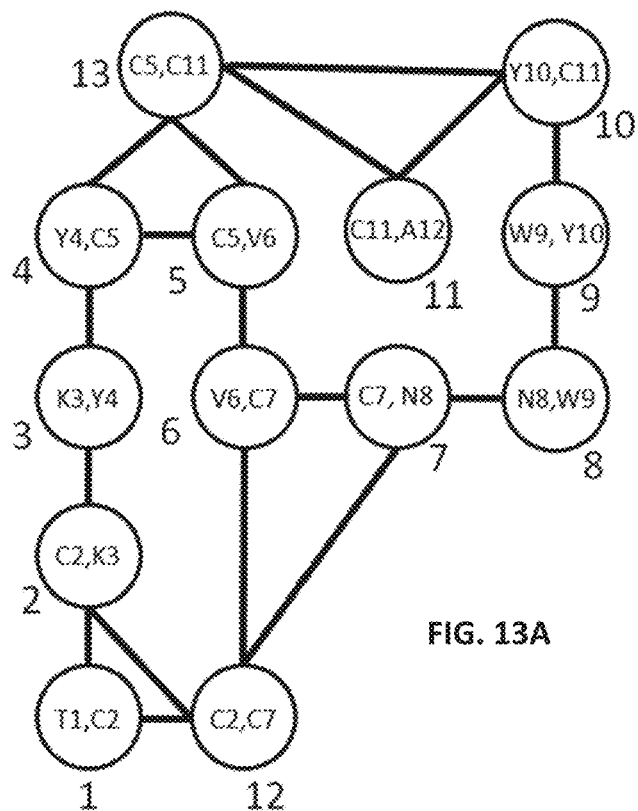
FIG. 13A is a line graph of the MCU graph for Peptide A and FIG. 13B shows the corresponding line graph data structure generated in accordance with the invention.
Figure 14:
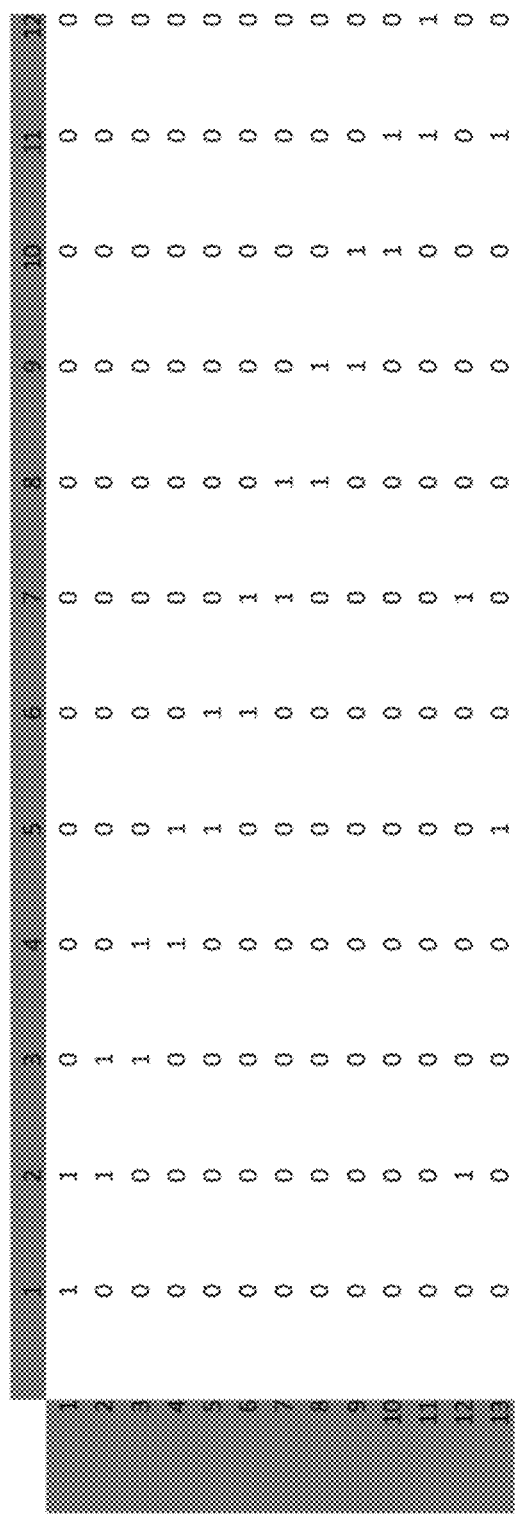
FIG. 14 shows an Edge to Vertex data structure generated from the MCU graph of Peptide A.

FIG. 13A shows a line graph of Peptide A that may be generated in accordance with an embodiment of the invention. Vertices of the line graph are represented as circles and numbered 1-12. For ease of understanding, vertices contain the single letter amino acid and position within the peptide that represent the endpoints of a given edge of the MCU graph of Peptide A. The corresponding MCU graph data structure is set forth in FIG. 13B. The corresponding E2V Matrix data structure is set forth in FIG. 14. In the E2V matrix Edges are represented as rows 1-13 and vertices are represented as columns 1-12.

FIGS. 15A and 15B show exemplary data for the ICS records stored in a subgraph database generated in accordance with an embodiment of the present invention, including the molecular weight field, vertex array field, and edge array field. The ICS records represent induced connected subgraphs of the line graph of Peptide A. As shown in rows 3 and 4 of FIG. 15A, two of the ICS records show the same molecular weight, but differing Vertex values in the vertex data field and differing edge values in the edge data field. Thus, the configuration of the subgraph database generated by the embodiments of the present invention permit the system to distinguish ICSs (and thus substructures of the chosen molecule) that have the same molecular weight.

Figure 16:
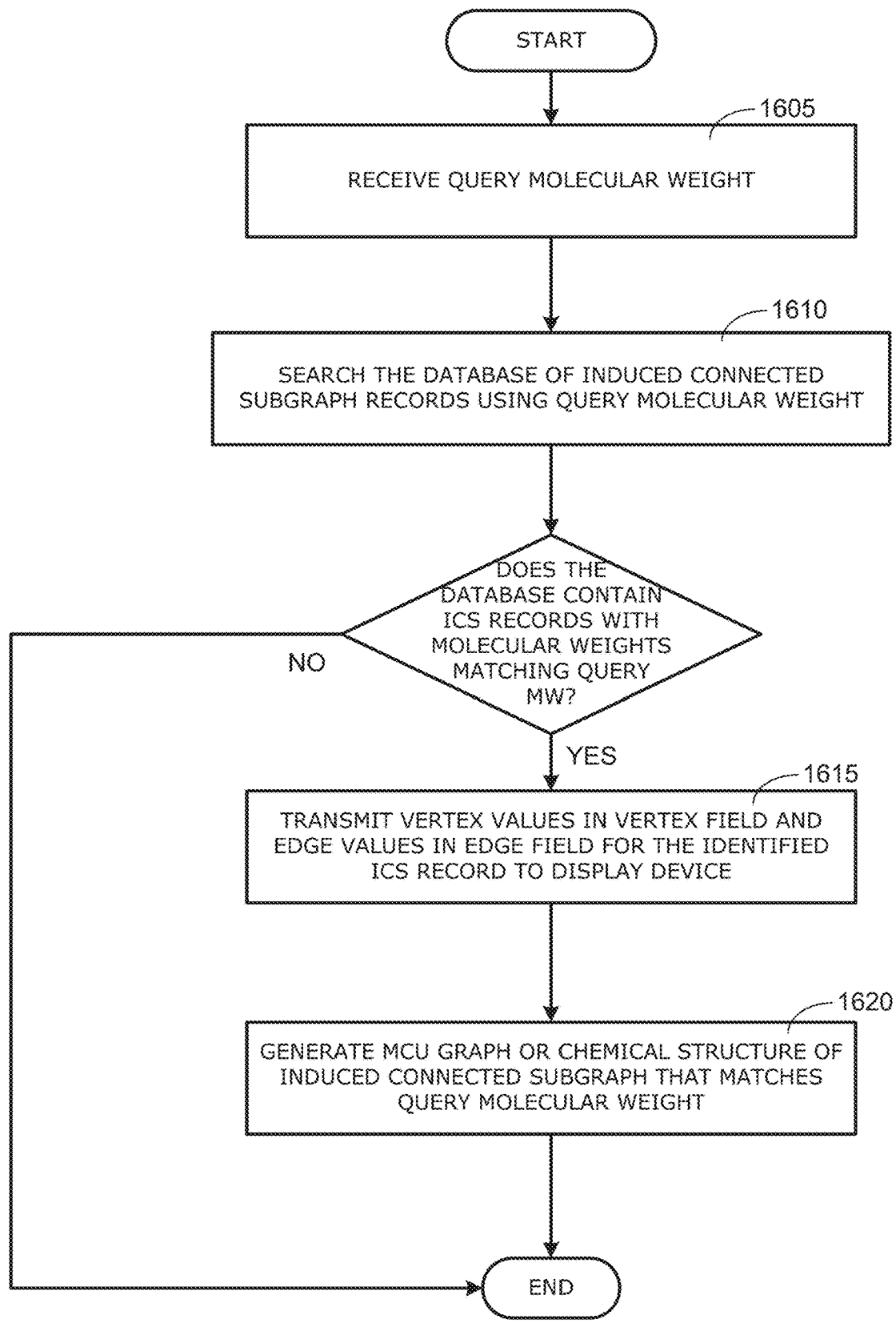
FIG. 16 is a flow diagram illustrating the steps, in accordance with one embodiment of the invention, in searching the database of induced connected subgraphs to identify a substructure of a chosen molecule.

FIG. 16 shows a flow diagram illustrating the steps of an exemplary searching process carried out in accordance with one embodiment of the invention. The search may be performed asynchronously with the first phase of operation of the invention. The search process utilizes the database of stored induced connected subgraph records created in the first phase of operation. At step 1605, the system receives a query molecular weight. At steps 1610 and 1615, the system searches the database of stored induced connected subgraph records generated at Steps 630 and 635 using the query molecular weight in order to identify induced connected subgraph records having molecular weight field values that match the query molecular weight, i.e., records that have molecular weights in the molecular weight field that are within a specified range of the query molecular weight, preferably within 5 ppm of the query molecular mass, more preferably with 4 ppm of the query molecular mass, and more preferably within 2 ppm of the query molecular mass. In some embodiments, the search of the induced connected subgraph records may be carried out by a search engine module (i.e., a computer program) comprising program instructions configured to cause the microprocessor to search for and retrieve data from the ICS records stored in the subgraph database during the first phases of operation of the invention. The query molecular weight is typically an experimentally observed or known molecular weight of a substructure of the chosen molecule. A query molecular weight may be generated using technology such as mass spectrometry, and particularly differential mass spectrometry.

At step 1615, the system displays to the user vertex values from the vertex data field and edge values from the edge data field for the identified induced connected subgraph record in the database. This step is achieved by transmitting the vertex values and edge values from the identified ICS record to a user interface for presentation on a display device operated by an end user.

In an additional embodiment of the invention, the system may use the vertex values in the vertex data field, the edge values in the edge data field and the chosen molecule data to produce a graphical representation of an induced connected subgraph of the line graph and transmit the graphical representation to the display device operated by the end user. See Step 1620 of FIG. 16. The graphical representation may be an MCU graph or a chemical structure diagram of the substructure represented by the induced connected subgraph record. It is noted that displaying the graphical representation, as set forth at Step 1620, is an optional step, depending on whether the user wishes to see the graphical representation, or is satisfied with receiving (or being presented with) the vertex values and the edge values for the induced connected subgraphs of the line graph.

Figure 17A:
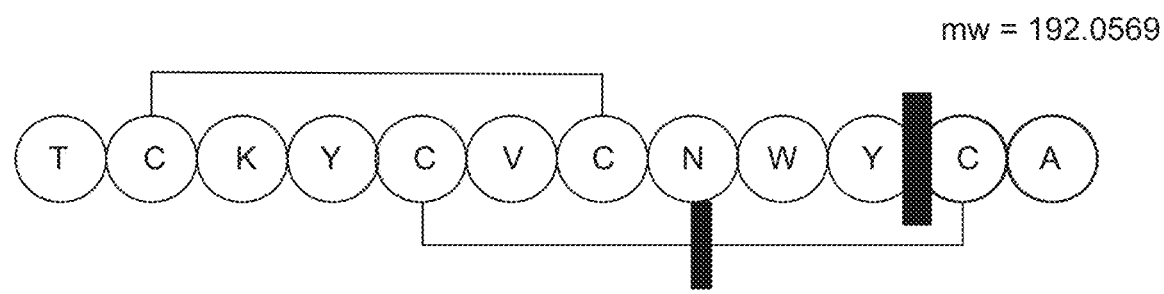
FIG. 17A shows an MCU graph of a substructure of Peptide A, generated in accordance with an embodiment of the invention.
Figure 17B:
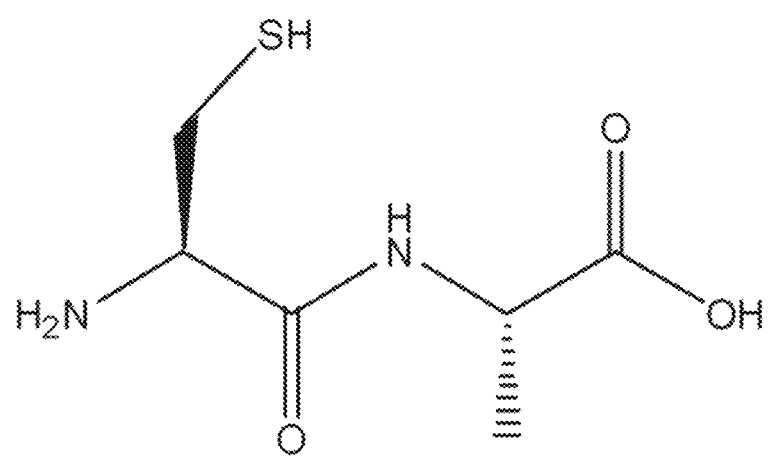
FIG. 17B shows the chemical structure corresponding to the substructure depicted in the MCU graph of FIG. 17A.

FIG. 17A shows graphical representation, i.e., an MCU graph, represented by an induced connected subgraph (ICS) of the line graph of Peptide A. The substructure has a molecular weight of 192.0569 daltons. FIG. 17B shows the corresponding chemical structure of the substructure represented by the MCU graph of FIG. 17A.

Figure 18A:
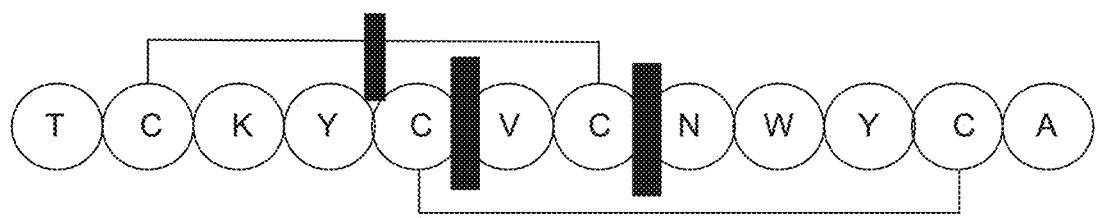
FIGS. 18A and 19A show MCU graphs of two substructures of Peptide A, generated in accordance with an embodiment of the invention.
Figure 18B:
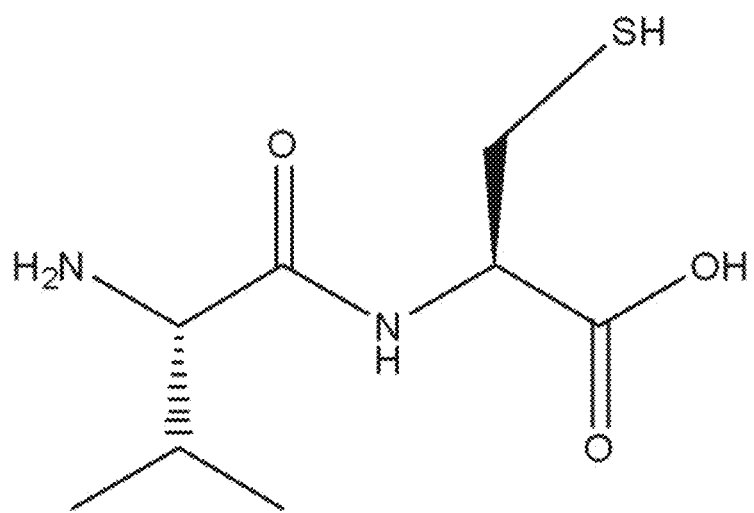
FIGS. 18B and 19B show the chemical structure corresponding to the substructure depicted in the MCU graph of FIGS. 18A and 19A, respectively.
Figure 19A:
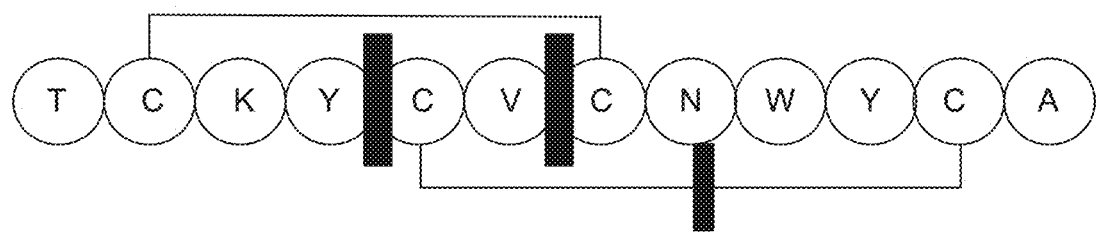
Figure 19B:
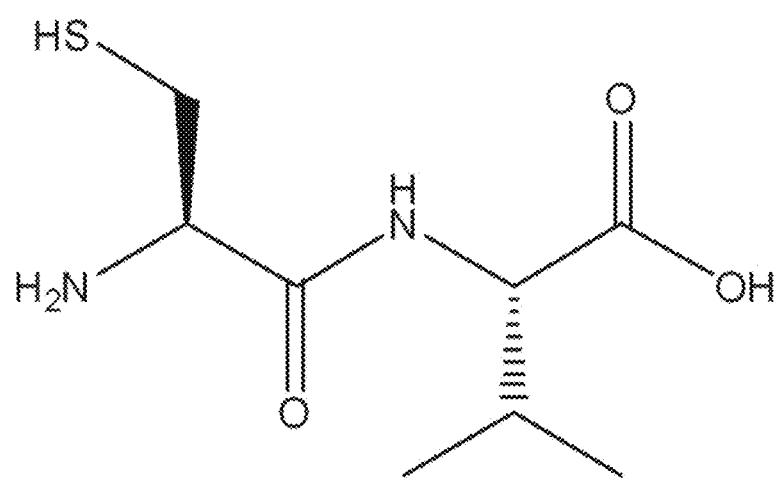

FIGS. 18A and 19A show graphical representations, i.e., MCU graphs, represented by ICSs of the line graph of Peptide A. The MCU graphs represent substructures of Peptide A that have a molecular weight of 220.0882 daltons. FIGS. 18B and 19B show the corresponding chemical structures of the substructure represented by the MCU graph of FIGS. 18A and 19A, respectively.

Figure 20A:
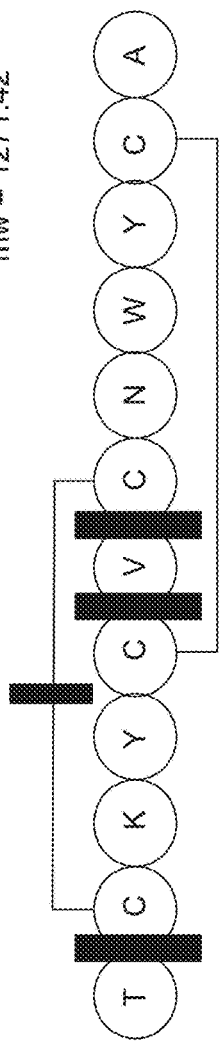
FIGS. 20A and 21A show the MCU graphs of two substructures of Peptide A, generated in accordance with an embodiment of the invention.
Figure 20B:
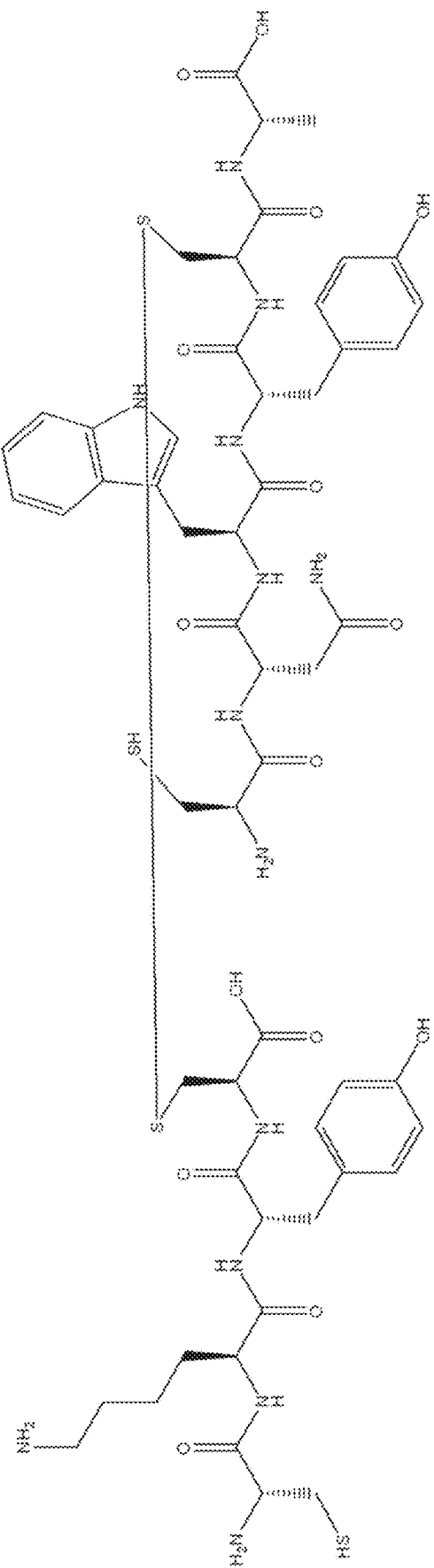
FIGS. 20B and 21B show the chemical structures corresponding to the substructures depicted in the MCU graphs of FIGS. 20A and 21A, respectively.
Figure 21A:
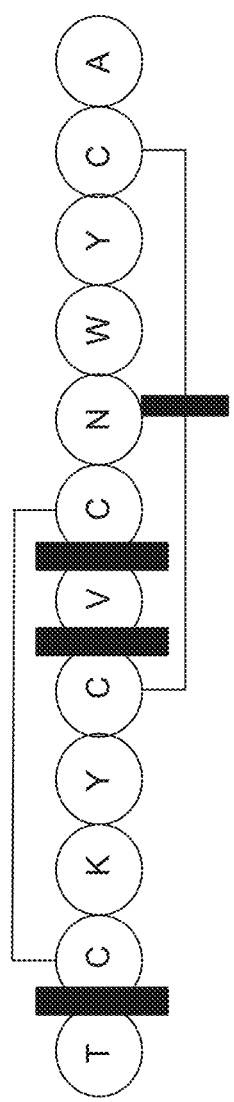
Figure 21B:
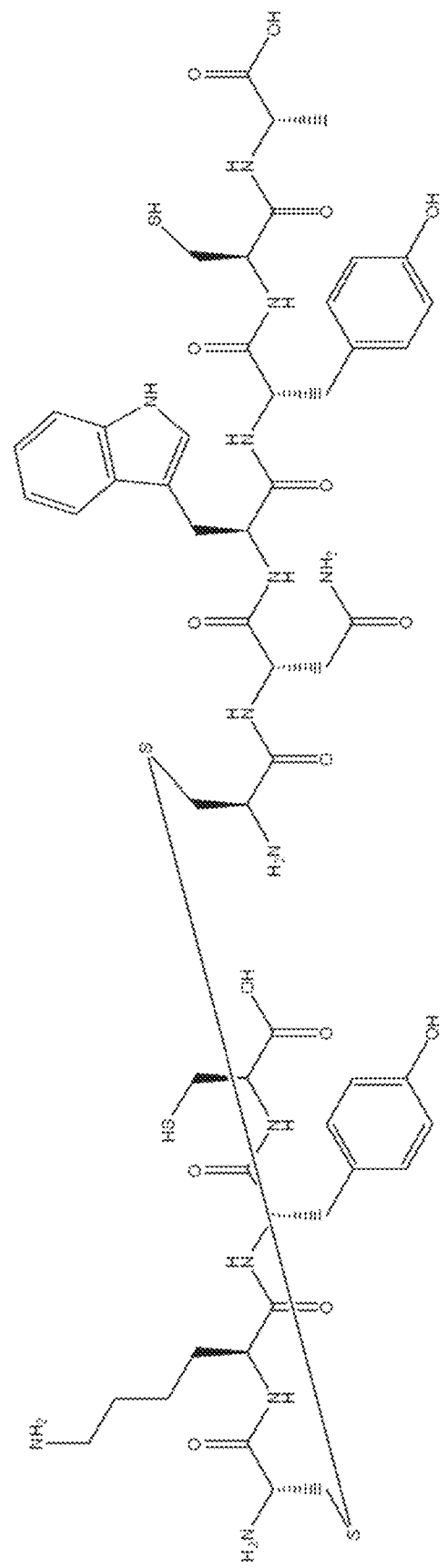

FIGS. 20A and 21A show graphical representations, i.e., MCU graphs, represented by ICSs of the line graph of Peptide A. The MCU graphs represent substructures of Peptide A that have a molecular weight of 1271.42 daltons. FIGS. 20B and 21B show the corresponding chemical structure of the substructures represented by the MCU graphs of FIG. 20A and FIG. 21A, respectively.

Figure 22B:
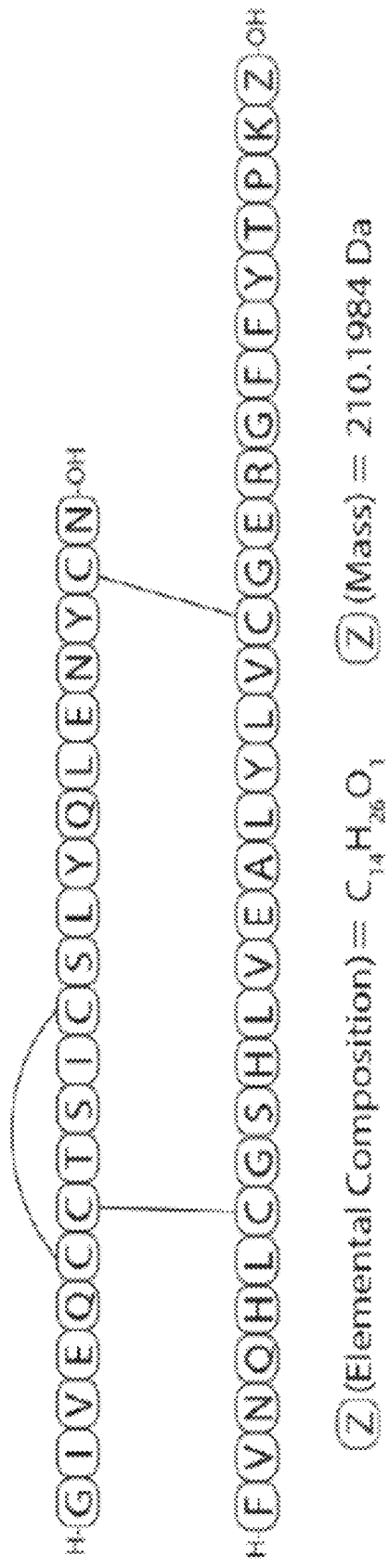
FIGS. 22B and 22C are MCU graphs of insulin detemir generated in accordance with an embodiment of the invention.
Figure 22C:
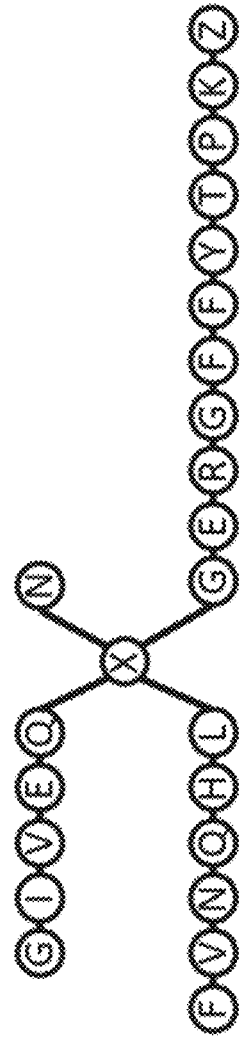

FIG. 22A shows the chemical structure of another chosen molecule, namely insulin detemir. FIGS. 22B and 22C depict the MCU graphs of insulin detemir. In the MCU graph of FIG. 22B, MCUs include single amino acid residues and elemental composition. The elemental composition ($C_{12}H_{60}O_1$) is designated by the encircled Z. FIG. 22C shows that part of the molecule, designated by the encircled X has been abstracted out into a single MCU. A user who is not interested in cleavages with the abstracted region of the molecule may use this approach to tailor the pool of substructures that would be generated by the invention.

Figure 23:
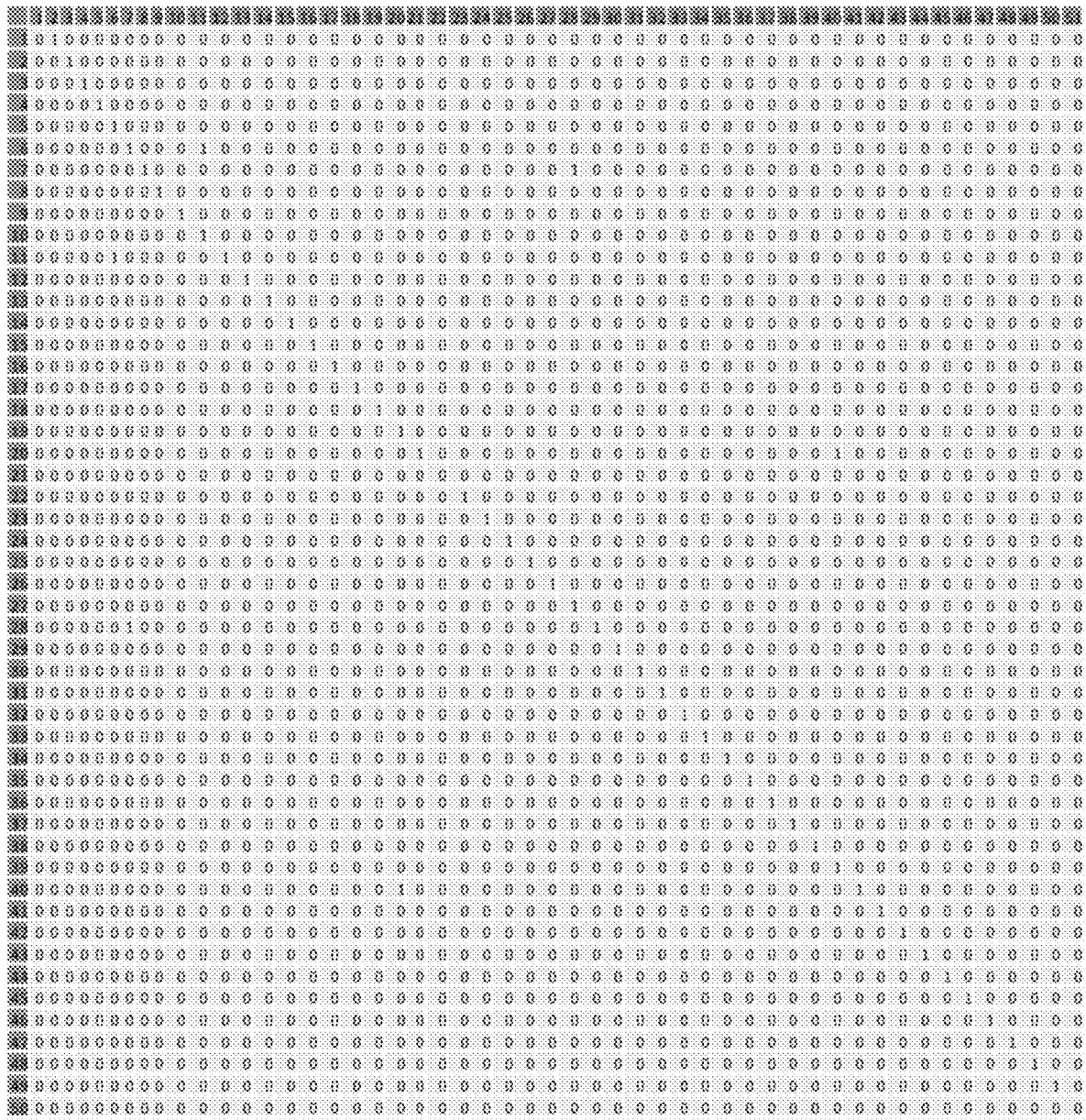
FIG. 23 shows an MCU graph data structure for insulin detemir generated in accordance with the invention.

FIG. 23 shows the MCU graph data structure for insulin detemir generated in accordance with the invention. The adjacency matrix is a 50×51 matrix.

Figure 24:
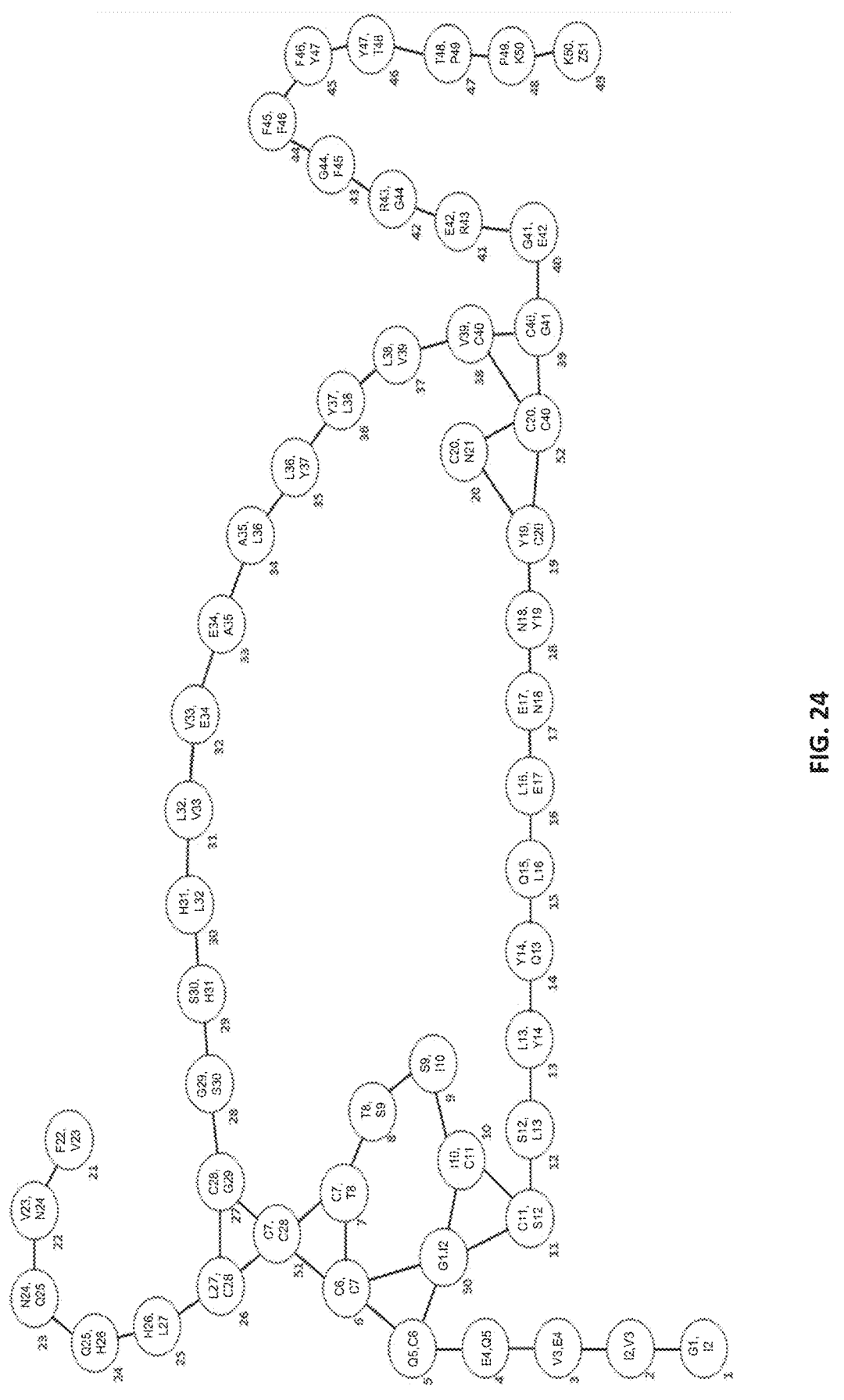

FIG. 24 shows a line graph of the MCU graph represented in FIG. 22B of insulin detemir. The line graph has 52 vertices, as designated by the numerical values assigned thereto.

Figure 25:
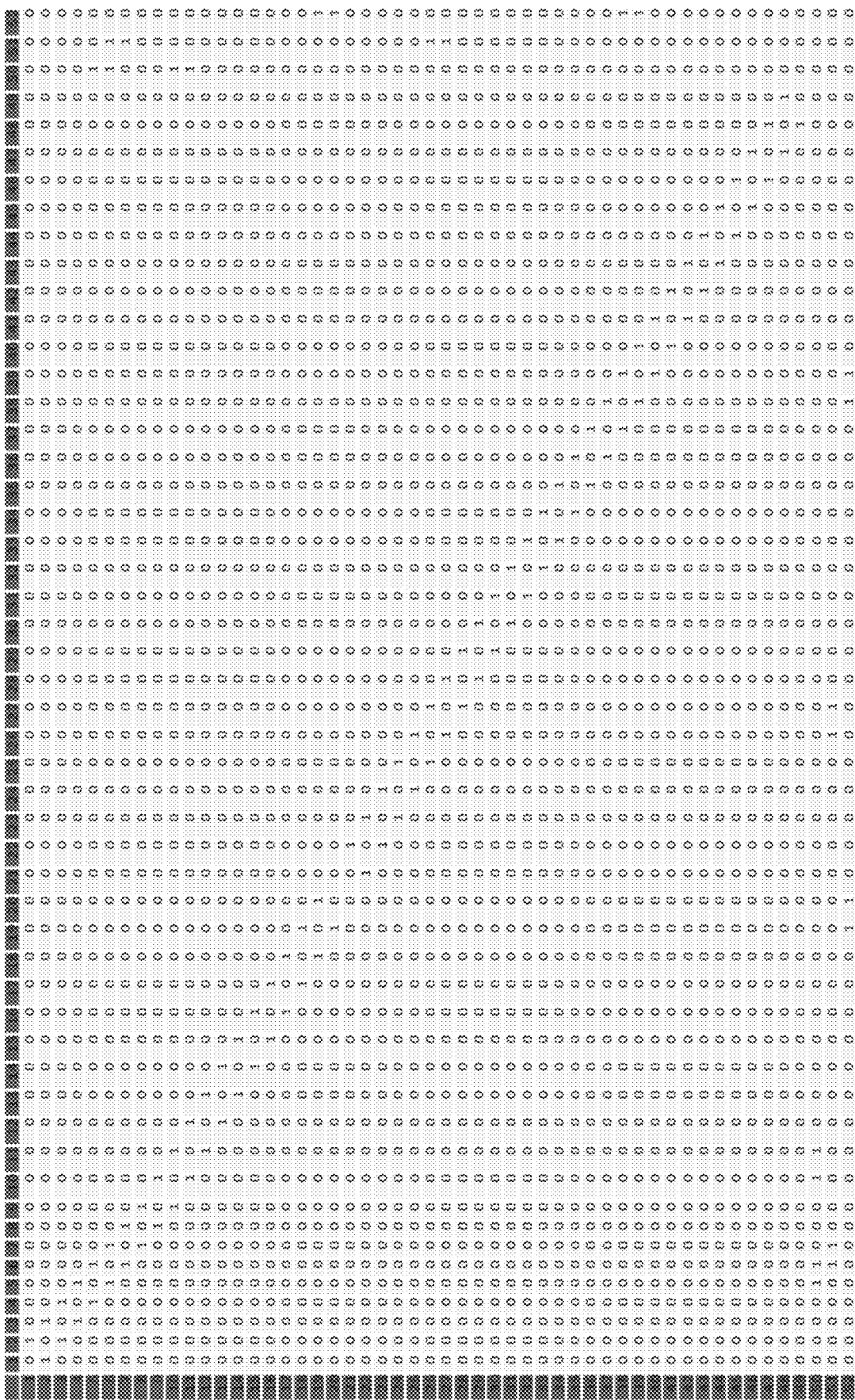
FIG. 25 shows the line graph data structure for insulin determir generated in accordance with an embodiment of the invention.

FIG. 25 shows the line graph data structure for the insulin detemir, generated from the MCU graph data structure set forth in FIG. 23. The data structure is a 52×52 adjacency matrix.

Figure 26:
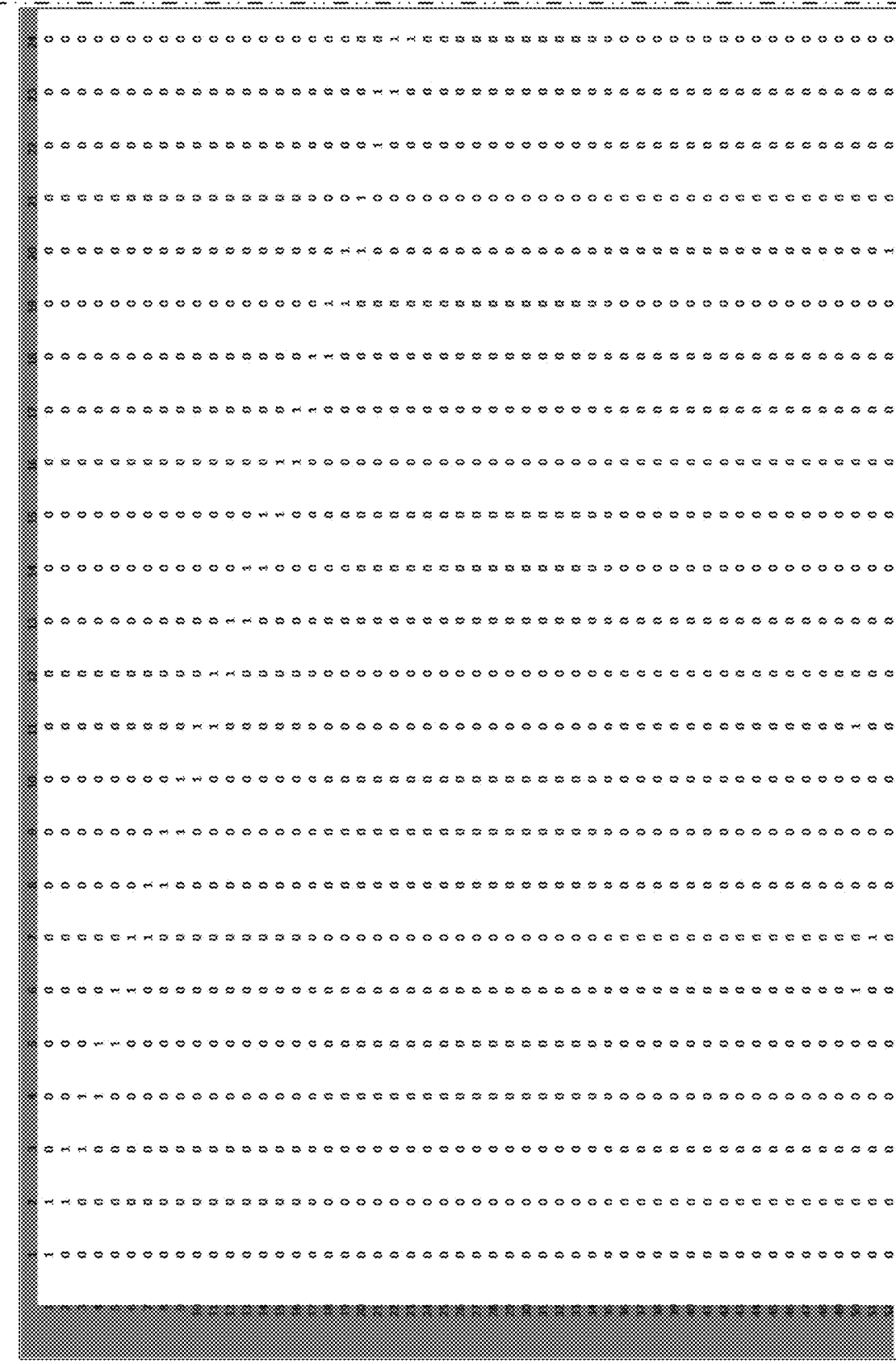
FIG. 26 shows an Edge to Vertex data structure generated from the MCU graph data structure in accordance with an embodiment of the invention.

FIG. 26 depicts an edge to vertex data structure generated in accordance with the invention from the MCU graph data structure shown in FIG. 23.

Figure 27:
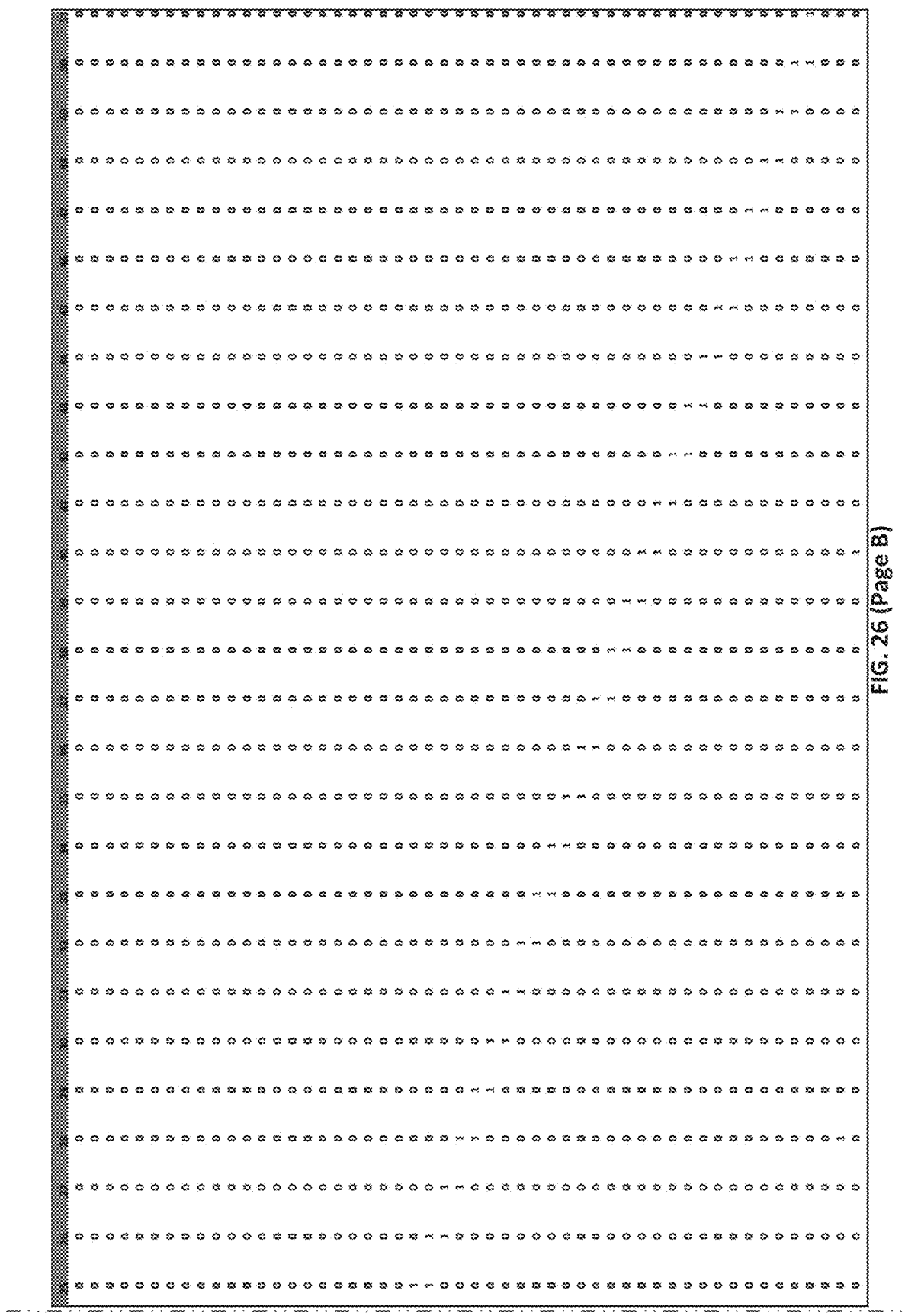
FIG. 27 shows exemplary MatLab code program instructions for populating a substructure database from MCU graph data stored in an MCU graph adjacency matrix in accordance with an embodiment of the present invention.

FIG. 27 shows exemplary MatLab code program instructions configured to carry out a graph traversing algorithm to populate a substructure database from MCU graph data stored in an MCU graph adjacency matrix. As shown in FIG. 27, the code receives as input data stored in an MCU graph adjacency matrix data structure E2V and the data stored in a line graph adjacency matrix data structure J. Note that the latter may be derived from the former. Therefore, the algorithm represented by the MatLab code shown in FIG. 27 may be written so that it ONLY requires the data from the MCU graph adjacency matrix data structure to populate the ICS database.

Figure 28:
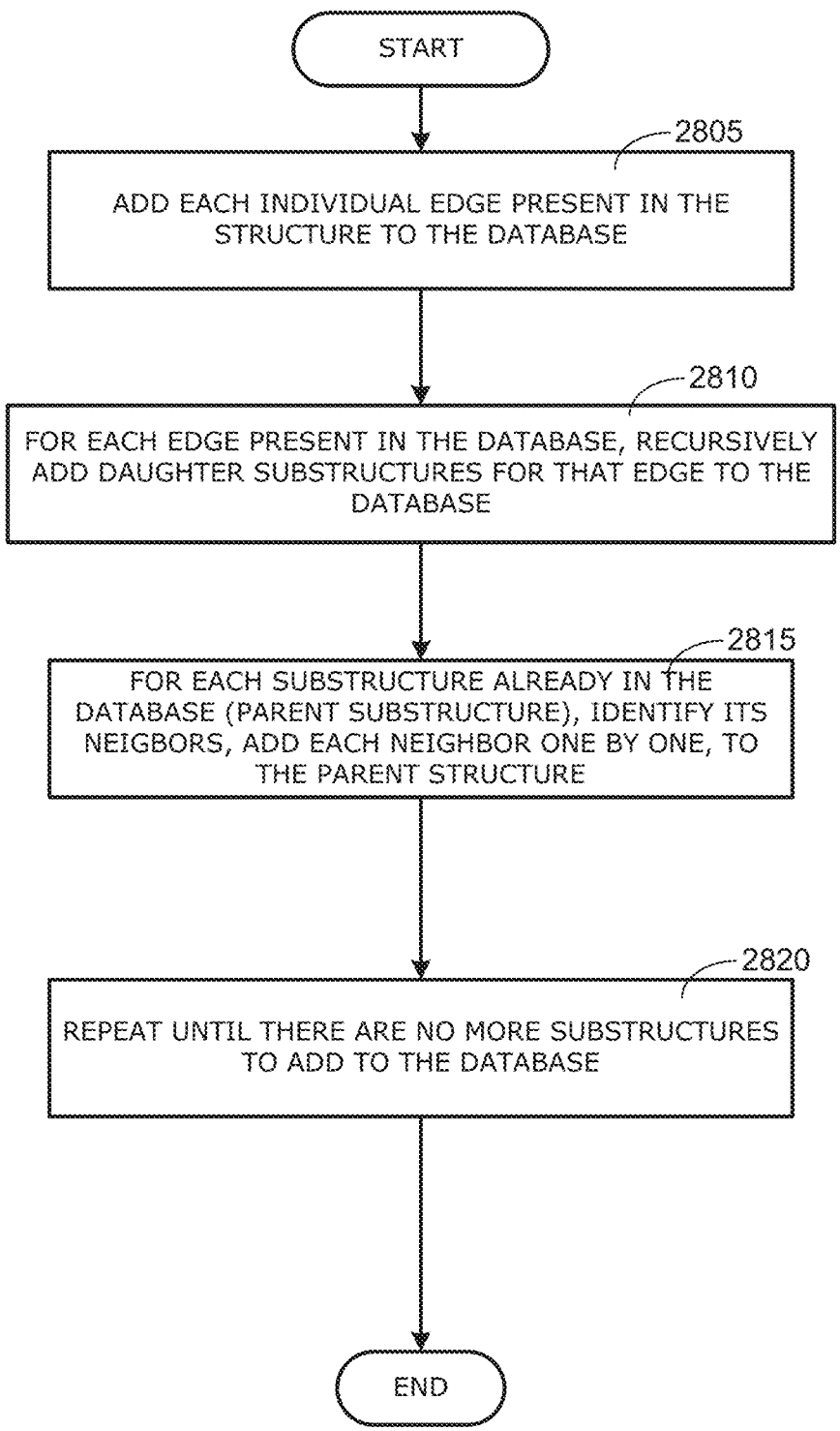
FIG. 28 shows a flow diagram illustrating the algorithm performed by the exemplary code shown in FIG. 27.

FIG. 28 shows a flow diagram illustrating the algorithm performed by the exemplary code shown in FIG. 27. As shown in FIG. 28, the algorithm for traversing the graph data structure to populate the subgraph database comprises the following steps: First, at step 2805, add to the database data representing each individual edge present in the structure. Then, at step 2810, for each edge present in the database, recursively add to the database all of the daughter substructures for that edge. Next, at step 2815, for each substructure already in the database (i.e., each parent substructure), identify its neighbors and add each neighbor, one by one, to the parent structure and, at step 2820, repeat steps 2810, 2815 and 2820 until there are no more substructures to add to the database.

Figure 29:
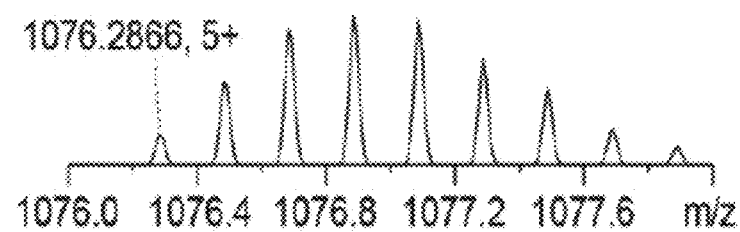
FIG. 29 is an experimental isotope envelope of a potential metabolite of an insulin detemir in rat kidney membrane incubation, which has a monoisotopic m/z at 1076.2866 Th([M+5H]) and a molecular mass of 5376.3965 Da.

FIG. 29 is an experimental isotope envelope of a potential metabolite of an insulin detemir in rat kidney membrane incubation, which has a monoisotopic m/z at 1076.2866 Th([M+5H]) and a molecular weight of 5376.3965 Da. The molecular weight was used as a query molecular weight to search a database of ICS records in accordance with the algorithm illustrated by the flow diagram shown in FIG. 16. A binary search of the database was performed to identify ICS records having a molecular weight that matched the query molecular within 2 ppm.

FIGS. 30A-30D show four exemplary database entries (ICS records) generated in the binary search of the database containing vertex arrays and edge arrays representing induced connected subgraphs of insulin detemir. Three of the ICSs had a molecular weight of 5376.4044 and one ICS had a molecular weight of 5376.3945.

Figure 31A:
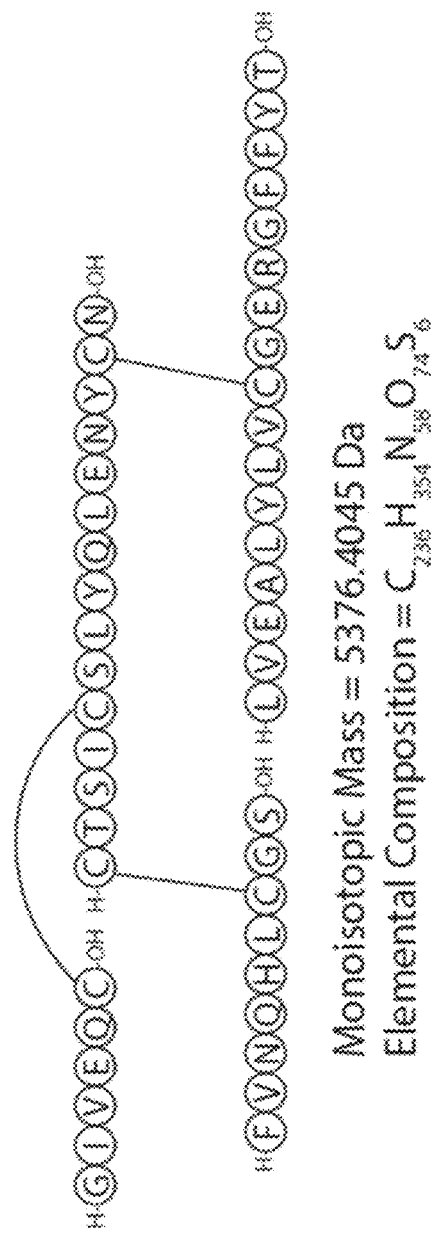
FIGS. 31A and 31B show MCU graphs of induced connected subgraphs of the line graph data structure for insulin detemir.
Figure 31B:
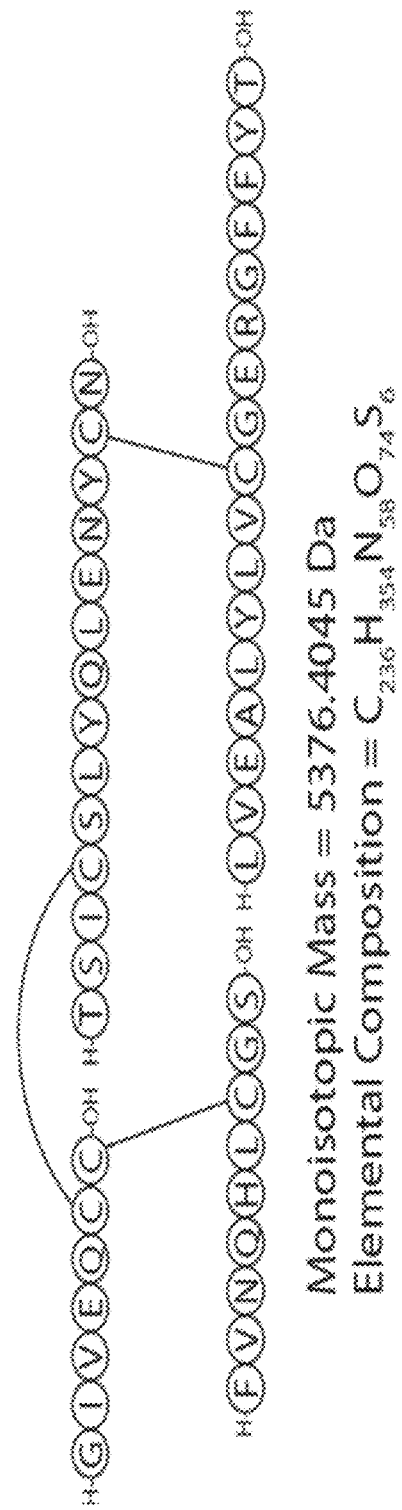
Figure 31C:
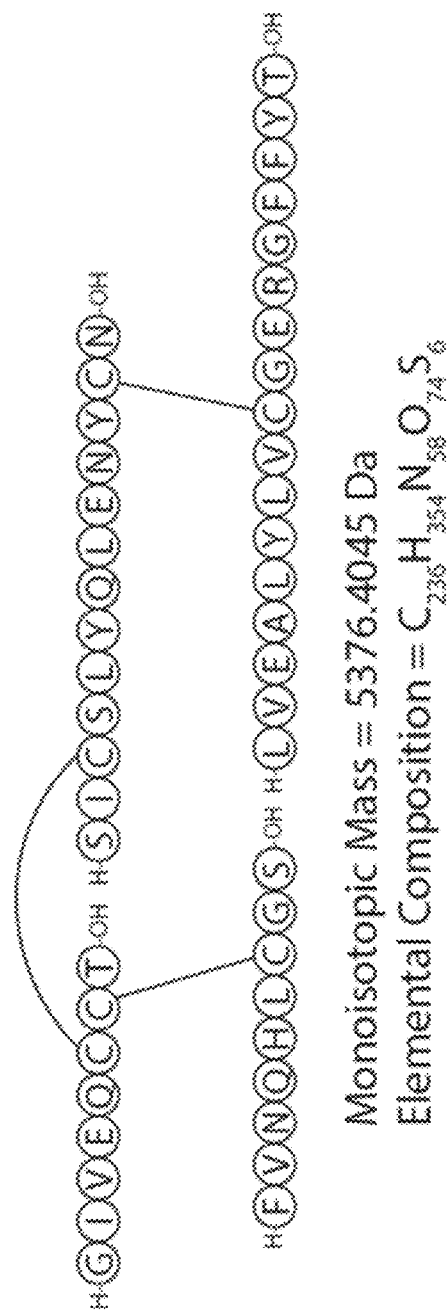
FIG. 31C-31F show MCU graphs of induced connected subgraphs corresponding to vertex arrays and edge arrays shown in FIGS. 30A-30D.
Figure 31D:
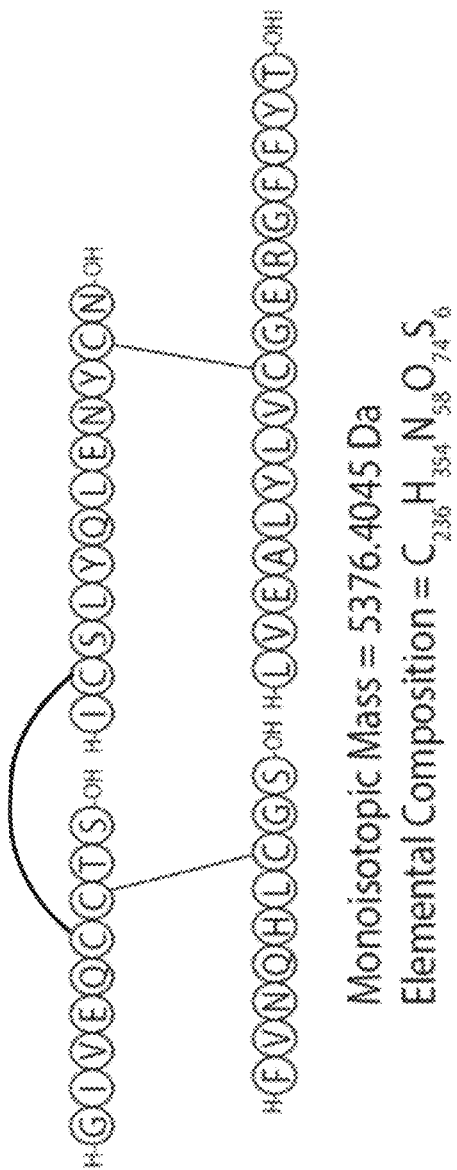
Figure 31E:
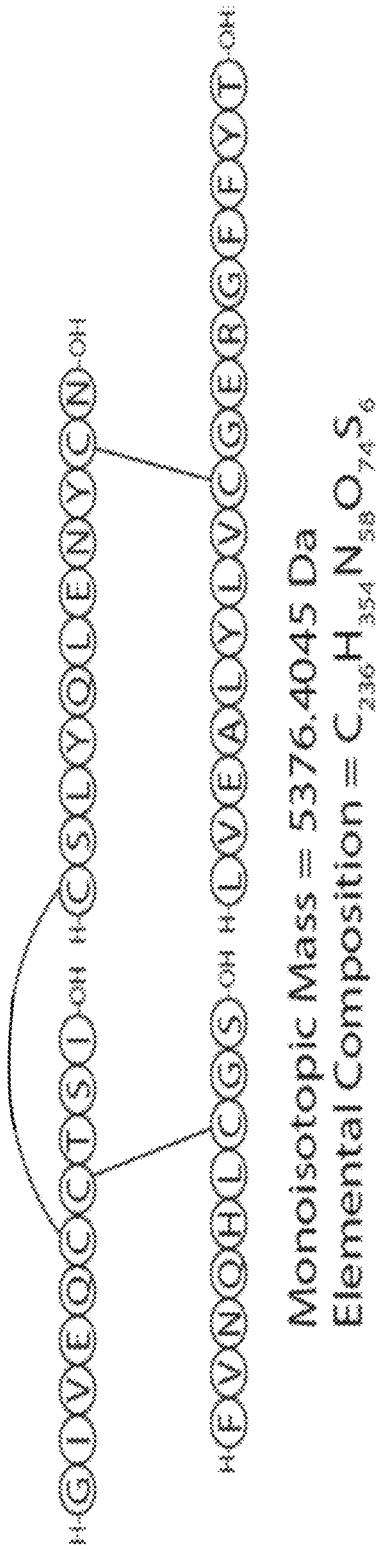

FIGS. 31A and 31B show MCU graphs of induced connected subgraphs of the line graph data structure for insulin detemir.

FIG. 31C-31F show MCU graphs of the four induced connected subgraphs corresponding to the vertex arrays and edge arrays shown in FIGS. 30A-30D, respectively.

FIGS. 32A, 32B, 33A and 33B show proposed chemical structures of the four induced connected subgraphs corresponding to the vertex arrays and edge arrays shown in FIGS. 30A-30D, respectively.

Figure 31F:
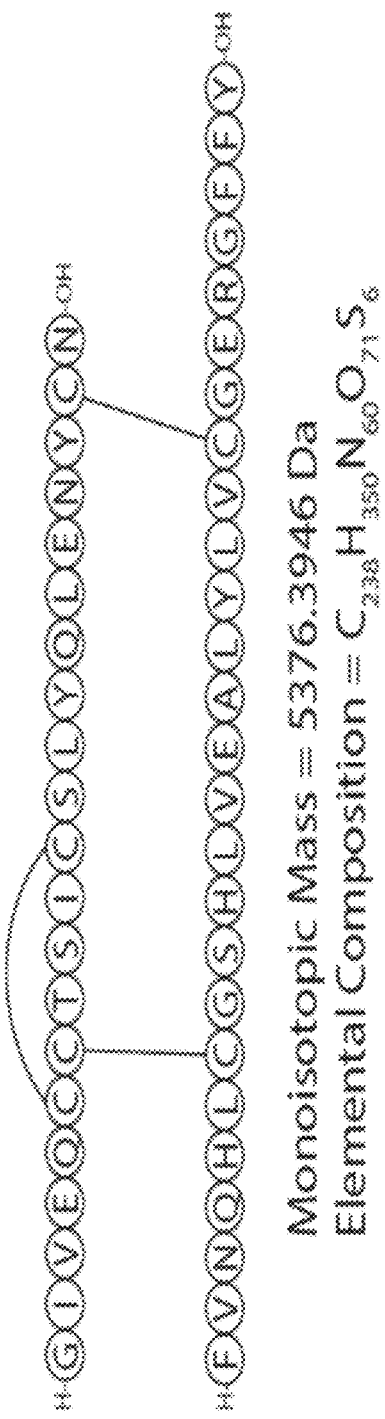
Figure 34A:
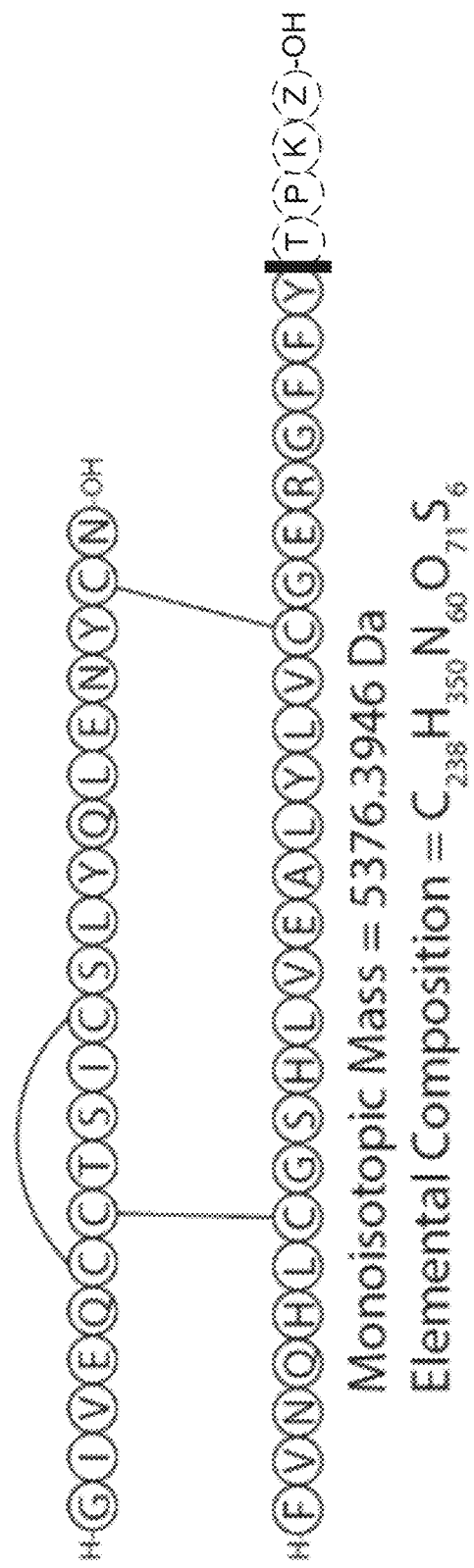
FIG. 34A is a metabolic cleavage map of the structure shown in FIG. 31F, a metabolite of the insulin detemir.
Figure 34B:
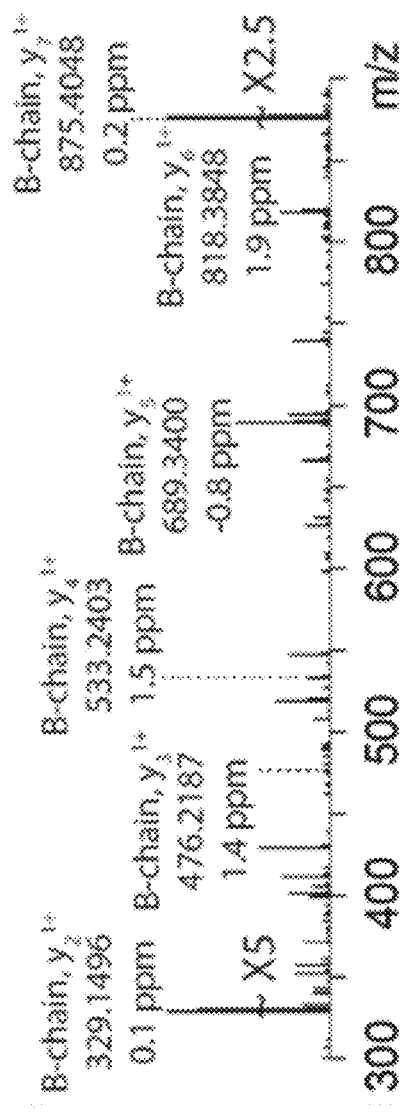
FIG. 34B is an MS/MS $y_2$-$y_7$ ion spectrum of the metabolite shown in FIG. 31F.
Figure 34C:
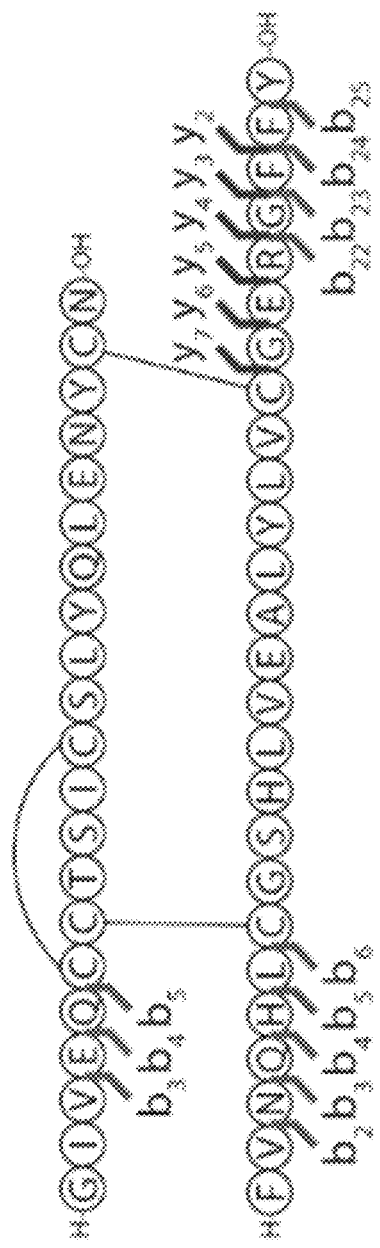
FIG. 34C is an MS/MS fragmentation map of the insulin detemir metabolite shown in FIG. 31F.

FIG. 34A is a metabolic cleavage map of the structure shown in FIG. 31F, a metabolite of the insulin detemir; FIG. 34B is an MS/MS $y_2$-$y_7$ ion spectrum generated to validate the structure of the metabolite shown in FIG. 31F. The MS/MS produced $y_2$-$y_7$ ion series is consistent with the structure set forth in FIG. 31F, not the structures shown in FIGS. 31C, 31D and 31F. FIG. 34C is an MS/MS fragmentation map of the insulin detemir metabolite shown in FIG. 31F. In FIG. 34C, a metabolic cleavage site, an isomeric cleavage site, a retaining MCU, a leaving MCU, $y_n$ ion and $b_n$ ion are denoted as follows:

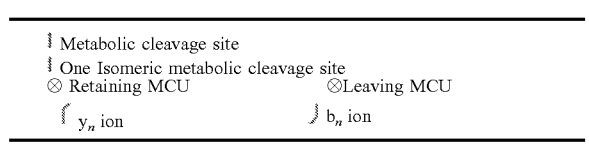

While the invention has been described in detail with reference to specific examples, it will be apparent to one skilled in the art that various modifications can be made within the scope of this invention. Thus, the scope of the invention should not be limited by the examples described herein, but by the claims presented below.

We claim:

1. A system for identifying substructures of a chosen molecule, the system comprising:
   a) a microprocessor;
   b) a memory;
   c) an application program, in the memory, comprising program instructions that, when executed by the microprocessor, will cause the microprocessor to
      (i) receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween,
      (ii) based on the chosen molecule data, create and store in the memory a minimum cleavable unit graph data structure for the chosen molecule, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule,
      (iii) based on the MCU graph data, generate and store in the memory a line graph data structure, the line graph data structure being populated with line graph data representing a line graph for the MCU graph, the line graph having a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge, (iv) execute a graph traversal algorithm against the line graph data in the line graph data structure to determine a plurality of induced connected subgraphs for the line graph, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule, (v) for each induced connected subgraph represented in the line graph data structure, create in a database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate an edge position of every LG edge in the induced connected subgraph relative to the LG vertices, and (vi) for each ICS record in the line graph data structure, calculate and store in the molecular weight field a total molecular weight for the induced connected subgraph of that ICS record based on the chosen molecule data for the chosen molecule and the vertex values and the edge values in the ICS record;

d) a user interface for communication with an end user; and e) program instructions in the user interface that, when executed by the microprocessor, will cause the microprocessor to (i) receive a query molecular weight from the end user, (ii) search the database based on the query molecular weight to identify an ICS record having a total molecular weight in the molecular weight field that matches the query molecular weight, and (iii) transmit the vertex values in the vertex data field and the edge values in the edge data field for the identified ICS record to the user interface for presentation on a display device operated by the end user.

2. The system according to claim 1, further comprising program instructions in the user interface that, when executed by the microprocessor, will cause the microprocessor to:

a) use the vertex values in the vertex data field, the edge values in the edge data field and the chosen molecule data to produce a graphical representation of an induced connected subgraph of the line graph; and b) transmit the graphical representation to the display device operated by the end user.

3. The system of claim 1, further comprising program instructions in the application program that, when executed by the microprocessor, causes the microprocessor to c) receive a specified tolerance for the molecular weight;

d) use the specified tolerance to calculate and define a range of molecular weights for the search of the database;

e) search the database based on the query molecular weight and the range to identify each ICS record in the database that has a total molecular weight in the molecular weight field that falls within the range of molecular weights; and f) for said each identified ICS record, transmit the vertex values in the vertex data field and the edge values in the edge data field to the user interface for presentation to the end user.

4. The system according to claim 1, wherein the chosen molecule data is received by parsing information stored in a linked list, or an array, or an adjacency matrix, or a graphic image file, or a chemical drawing file, or a spreadsheet file, or a text file, or a CSV file, or a .CDX file, or a .CDXML file, or a .MOL file, or a .SDM file, or a CAD file, or a binary data file.

5. The system according to claim 1, wherein the connected subset of the set of minimum cleavable units and bonds is a metabolite of the chosen molecule, or a catabolite of the chose molecule, or a gas phase fragmentation of the chosen molecule, or a degradant of the chosen molecule, or a substructure of the chosen molecule.

6. The system according to claim 1, wherein the graph traversal algorithm is a depth-first search algorithm, or a breadth-first search algorithm, or a reverse-search algorithm, or a tree-search algorithm, or a combination of two of more of the graph traversal algorithms recited herein.

7. The system according to claim 1, wherein:

a) the chosen molecule data includes elemental composition data representing (A) a set of elemental units in each minimum cleavable unit, (B) a set of elemental bonds connecting the set of elemental units in the minimum cleavable unit, (C) elemental molecular weights for each elemental unit, and (D) an MCU connectivity profile for the minimum cleavable unit, the MCU connectivity profile indicating relative positions of elemental units and elemental bonds in the minimum cleavable units and connections therebetween; and b) the ICS record created in the database further comprises an elemental unit field populated with one or more elemental unit identifiers; and c) the application program further includes program instructions that, when executed by the microprocessor, will cause the microprocessor to (i) receive a query elemental unit from the end user, (ii) search the database based on the query elemental unit to identify an ICS record having an elemental unit identifier in the elemental unit field that matches that matches the query elemental unit, and (iii) transmit the vertex values in the vertex data field and the edge values in the edge data field for the identified ICS record to the user interface for presentation on a display device operated by the end user.

8. A system for generating a database comprising substructures of a chosen molecule using a microprocessor, the system comprising:

a) a memory;

b) a microprocessor;

c) an input module in the memory that, when executed by the microprocessor, causes the microprocessor to receive and store chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the minimum cleavable units and the bonds in the chosen molecule, the connectivity profile indicating relative positions of minimum cleavable units and bonds and connections therebetween;

d) an MCU graph module in the memory that, when executed by the microprocessor, causes the microprocessor to create in the memory a minimum cleavable unit graph data structure for the chosen molecule based on the chosen molecule data, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule;

e) a line graph module in the memory that, when executed by the microprocessor, will cause the microprocessor to generate and store in the memory a line graph data structure populated with line graph data representing a line graph for the MCU graph, the line graph having a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge;

f) a graph traversal module in the memory that, when executed by the microprocessor, will cause the microprocessor to run a graph traversing algorithm against the line graph data in the line graph data structure to determine a plurality of induced connected subgraphs for the line graph, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule; and g) a subgraph database generator in the memory that, when executed by the microprocessor, will cause the microprocessor to
  (i) for each induced connected subgraph represented in the line graph data structure, create in the database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate an edge position of every LG edge in the induced connected subgraph relative to the LG vertices, and
  (ii) for each ICS record in the line graph data structure, calculate and store in the molecular weight field a total molecular weight for the induced connected subgraph of that ICS record based on the chosen molecule data for the chosen molecule and the vertex values and the edge values in the ICS record.

9. The system of claim 8, wherein the chosen molecule data is received by parsing information stored in a linked list, or an array, or an adjacency matrix, or a graphic image file, or a chemical drawing file, or a spreadsheet file, or a text file, or a CSV file, or a .CDX file, or a .CDXML file, or a .MOL file, or a .SDM file, or a CAD file, or a binary data file.

10. The system according to claim 8, wherein the connected subset of the set of minimum cleavable units and bonds is a metabolite of the chosen molecule, or a catabolite of the chose molecule, or a gas phase fragmentation of the chosen molecule, or a degradant of the chosen molecule, or a substructure of the chosen molecule.

11. The system according to claim 8, wherein the graph traversal algorithm is a depth-first search algorithm, or a breadth-first search algorithm, or a reverse-search algorithm, or a tree-search algorithm, or a combination of two of more of the graph traversal algorithms recited herein.

12. The system according to claim 8, further comprising:
  a) a user interface for communication with an end user;
  b) a search engine in the memory having program instructions that, when executed by the microprocessor, will cause the microprocessor to
    (i) receive a query molecular weight from the end user,
    (ii) search the database based on the query molecular weight to identify an ICS record having a total molecular weight in the molecular weight field that matches the query molecular weight, and
    (iii) transmit the vertex values in the vertex data field and the edge values in the edge data field for the identified ICS record to the user interface for presentation on a display device operated by the end user.

13. The system according to claim 8, further comprising program instructions in the user interface that, when executed by the microprocessor, will cause the microprocessor to:
  a) use the vertex values in the vertex data field, the edge values in the edge data field and the chosen molecule data to produce a graphical representation of an induced connected subgraph of the line graph; and
  b) transmit the graphical representation to a display a device operated by the end user.

14. The system of claim 8, further comprising program instructions in an application program that, when executed by the microprocessor, causes the microprocessor to
  a) receive a specified tolerance for the molecular weight;
  b) use the specified tolerance to calculate and define a range of molecular weights for the search of the database;
  c) search the database based on a query molecular weight and the range to identify each ICS record in the database that has a total molecular weight in the molecular weight field that falls within the range of molecular weights; and
  d) for said each identified ICS record, transmit the vertex values in the vertex data field and the edge values in the edge data field to a user interface for presentation to the end user.

15. The system according to claim 8, wherein the graph traversal algorithm is a depth-first search, breadth-first search, a reverse-search, a tree-search, or a combination of two of more of the graph traversal algorithms recited herein.

16. A method for identifying substructures of a chosen molecule using a microprocessor and a memory device, the method comprising:
  a) with the microprocessor, receiving and storing in the memory device chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween;
  b) with the microprocessor, based on the chosen molecule data, creating and storing in the memory device a minimum cleavable unit graph data structure for the chosen molecule, the minimum cleavable unit graph data structure being populated with MCU graph data representing an MCU graph for the chosen molecule, the MCU graph having a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule;

c) with the microprocessor, based on the MCU graph data, generating and storing in the memory device a line graph data structure, the line graph data structure being populated with line graph data representing a line graph for the MCU graph, the line graph having a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge;

d) executing on the microprocessor a graph traversal algorithm against the line graph data in the line graph data structure to determine a plurality of induced connected subgraphs for the line graph, each induced connected subgraph comprising a connected subset of LG vertices and LG edges in the line graph, and a physical arrangement of said connected subset of LG vertices and LG edges, that together uniquely corresponds to a connected subset of the set of minimum cleavable units and bonds, and the relative positions of said connected subset of minimum cleavable units and bonds in the chosen molecule;

e) with the microprocessor, for each induced connected subgraph represented in the line graph data structure, creating in a database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate an edge position of every LG edge in the induced connected subgraph relative to the LG vertices; and f) with the microprocessor, for each ICS record in the line graph data structure, calculating and storing in the molecular weight field a total molecular weight for the induced connected subgraph of that ICS record based on the chosen molecule data for the chosen molecule and the vertex values and the edge values in the ICS record.

17. The method according to claim 16, wherein the graph traversal algorithm is a depth-first search, or a breadth-first search, or a reverse-search, or a tree-search, or a combination of two of more of the graph traversal algorithms recited herein.

18. The method according to claim 16, further comprising:
a) receiving a query molecular weight by the microprocessor;
b) with the microprocessor, searching the database based on the query molecular weight to identify an ICS record having in the molecular weight field a total molecular weight that matches the query molecular weight; and
c) transmitting a representation of the vertex values in the vertex data field and the edge values in the edge data field for the identified ICS record to a display device.

19. The method according to claim 18, further comprising:
a) with the microprocessor, producing a graphical representation of an induced connected subgraph of the line graph based on the connectivity profile of the chosen molecule, the vertex values in the vertex data field and the edge values in the edge data field; and
b) transmitting the graphical representation to the display device.

20. The method according to claim 16, wherein the connected subset of the set of minimum cleavable units and bonds is a metabolite of the chosen molecule, or a catabolite of the chose molecule, or a gas phase fragmentation of the chosen molecule, or a degradant of the chosen molecule, or a substructure of the chosen molecule.

21. An apparatus for creating and searching a database in a memory of a computer system using a microprocessor to identify chemical substructures of a chosen molecule, the apparatus comprising:
a) an input module stored in the memory;
b) a database generating module stored in the memory; and
c) a search engine stored in the memory;
d) wherein the input module comprises program instructions that, when executed by the microprocessor, causes the microprocessor to receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween;
e) wherein the database generating module comprises program instructions that, when executed by the microprocessor, causes the microprocessor to
(i) based on the chosen molecule data, create and store in the memory a V2V adjacency matrix for the chosen molecule, the V2V adjacency matrix comprising a plurality of V2V vectors, wherein the plurality of V2V vectors is populated with a set of V2V values selected to identify, for each pair of vertices in the chosen molecule, whether said pair of vertices are connected to each other by a bond in the chosen molecule;
(ii) generate and store in the memory an edge-to-vertex (E2V) adjacency matrix for the chosen molecule based on the V2V adjacency matrix, the E2V adjacency matrix comprising a plurality of E2V vectors, wherein the plurality of E2V vectors is populated with a set of E2V values selected to identify, for each edge-vertex pair in the V2V adjacency matrix, whether an edge and a vertex of said each edge-vertex pair are directly connected to each other in the chosen molecule, and
(iii) generate and store in the memory an edge-to-edge (E2E) adjacency matrix based on data in the E2V adjacency matrix, the E2E adjacency matrix comprising a plurality of E2E vectors, wherein the plurality of E2E vectors is populated with a set of E2E values selected to identify, for each pair of edges in the chosen molecule, whether said each pair of edges are directly connected to each other by a vertex in the chosen molecule; and
(iv) execute a graph traversing algorithm against the E2V values in the E2V adjacency matrix and the E2E values in the E2E adjacency matrix to determine every induced connected subgraph of the E2E graph, a vertex position for every vertex said every induced connected subgraph, and an edge position for every edge in said every induced connected subgraph, (v) for said every induced connected subgraph of the E2E graph, creating in the database an ICS record comprising a molecular weight field, a vertex data field and an edge data field, wherein the vertex data field is populated with vertex values configured to indicate the vertex position for said every vertex in the induced connected subgraph, and the edge data field is populated with edge values configured to indicate the edge position for said every edge in the induced connected subgraph, and (vi) use the connectivity profile, the set of molecular weights for the elements of the chosen molecule, and the ICS record for every induced connected subgraph to calculate and store in the molecular weight field of each ICS record a total molecular weight for the induced connected subgraph of that ICS record; and f) wherein the search engine comprises program instructions that, when executed by the microprocessor, causes the microprocessor to
  (i) receive a specified molecular weight,
  (ii) search the database to find at least one ICS record in which the total molecular weight in the molecular weight field is equivalent to the specified molecular weight, and
  (iii) transmit the vertex values of the vertex data field and the edge values of the edge data field for said at least one ICS record to a display device.

22. The apparatus of claim 21, further comprising a visualizer module, stored in the memory, comprising program instructions that, when executed by the microprocessor, will cause the microprocessor to retrieve and use the connectivity profile, a list of elements, the vertex values in the vertex data field and the edge values in the edge data field of said at least one ICS record to generate and display on the display device a graphical representation of the induced connected subgraph for said at least one ICS record.

23. The apparatus of claim 22, wherein the graphical representation comprises:
  a) a chemical structure diagram, or
  b) an MCU graph diagram, or
  c) a vertex to vertex (V2V) graph diagram, or
  d) an edge to edge (E2E) graph diagram, or
  e) an edge to vertex (E2V) graph diagram, or
  f) a line graph diagram, or
  g) a combination of two or more of the above-recited diagrams.

24. The apparatus of claim 21, wherein the graph traversing algorithm executed by the microprocessor under the control of the database generating module comprises:
  a) a depth-first search algorithm, or
  b) a breadth-first search algorithm, or
  c) a reverse-search algorithm, or
  d) a tree-search algorithm, or
  e) any combination of two or more of the graph traversal algorithms recited above.

25. The apparatus of claim 21, wherein the search engine further comprises program instructions that, when executed by the microprocessor, causes the microprocessor to
  a) receive a specified tolerance for the molecular weight;
  b) use the specified tolerance to calculate and define a range of molecular weights for the search of the database; and
  c) search the database to find the at least one ICS record in which the total molecular weight in the molecular weight field falls within the range of molecular weights.

26. The apparatus of claim 21, further comprising an MCU library, stored in the memory, comprising a set of MCU properties for the defined MCU, the set of MCU properties comprising:
  a) a list of constituents in the defined MCU, or
  b) a molecular weight for a constituent of the defined MCU, or
  c) a chemical structure for the defined MCU,
  d) a common name for the defined MCU, or
  e) any combination of two or more of the above-referenced MCU properties.

27. The apparatus of claim 21, wherein each of the induced connected subgraphs of the E2E graph has a connected set of edges and vertices, and a physical arrangement of said connected set of edges and vertices, that uniquely corresponds to a connected set of elements and a physical arrangement of said connected set of elements for a metabolite of the chosen molecule, or a catabolite of the chose molecule, or a gas phase fragmentation of the chosen molecule, or a degradant of the chosen molecule, or a substructure of the chosen molecule.

* * * * *

UNITED STATES PATENT AND TRADEMARK OFFICE
CERTIFICATE OF CORRECTION

| | | |
|---|---|---|
| PATENT NO. | : 11,854,664 B2 | Page 1 of 1 |
| APPLICATION NO. | : 16/973175 | |
| DATED | : December 26, 2023 | |
| INVENTOR(S) | : Fridman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this
First Day of July, 2025

Coke Morgan Stewart
*Acting Director of the United States Patent and Trademark Office*